(12) United States Patent
Kelley et al.

(10) Patent No.: US 12,285,424 B2
(45) Date of Patent: Apr. 29, 2025

(54) METHODS FOR TREATING NEUTROPENIA

(71) Applicant: X4 Pharmaceuticals, Inc., Boston, MA (US)

(72) Inventors: E. Lynne Kelley, Boston, MA (US); Sarah Cohen, Boston, MA (US)

(73) Assignee: X4 Pharmaceuticals, Inc., Boston, MA (US)

(*) Notice: Subject to any disclaimer, the term of this patent is extended or adjusted under 35 U.S.C. 154(b) by 0 days.

(21) Appl. No.: 17/941,509

(22) Filed: Sep. 9, 2022

(65) Prior Publication Data

US 2023/0014231 A1   Jan. 19, 2023

Related U.S. Application Data

(63) Continuation of application No. PCT/US2021/021713, filed on Mar. 10, 2021.

(60) Provisional application No. 62/987,707, filed on Mar. 10, 2020.

(51) Int. Cl.
*A61K 31/4709*   (2006.01)
*A61K 9/00*   (2006.01)
*A61P 7/00*   (2006.01)

(52) U.S. Cl.
CPC ........ *A61K 31/4709* (2013.01); *A61K 9/0019* (2013.01); *A61P 7/00* (2018.01)

(58) Field of Classification Search
CPC ... A61K 31/4709; A61K 9/0019; A61P 37/04; A61P 7/00; A61P 7/06; Y02A 50/30
See application file for complete search history.

(56) References Cited

U.S. PATENT DOCUMENTS

| | | | |
|---|---|---|---|
| 4,933,447 A | 6/1990 | Koono et al. | |
| 5,021,409 A | 6/1991 | Murrer et al. | |
| 5,235,056 A | 8/1993 | Cunkle et al. | |
| 5,563,151 A | 10/1996 | Bowles et al. | |
| 5,582,823 A | 12/1996 | Souza | |
| 5,583,131 A | 12/1996 | Bridger et al. | |
| 5,698,546 A | 12/1997 | Bridger et al. | |
| 5,817,807 A | 10/1998 | Bridger et al. | |
| 5,932,749 A | 8/1999 | Li et al. | |
| 6,001,826 A | 12/1999 | Murrer et al. | |
| 6,245,799 B1 | 6/2001 | Asselin et al. | |
| 6,268,354 B1 | 7/2001 | Nishimura et al. | |
| 6,365,583 B1 | 4/2002 | MacFarland et al. | |
| 6,506,770 B1 | 1/2003 | Bridger et al. | |
| 6,552,065 B2 | 4/2003 | Remiszewski et al. | |
| 6,635,278 B1 | 10/2003 | Dahl et al. | |
| 6,683,192 B2 | 1/2004 | Baxter et al. | |
| 6,734,191 B2 | 5/2004 | Bridger et al. | |
| 6,734,194 B2 | 5/2004 | End et al. | |
| 6,794,379 B2 | 9/2004 | Medina et al. | |
| 6,825,351 B2 | 11/2004 | McEachern et al. | |
| 6,835,731 B2 | 12/2004 | Bridger et al. | |
| 6,864,265 B2 | 3/2005 | Bridger et al. | |
| 6,878,714 B2 | 4/2005 | Askew et al. | |
| 6,987,102 B2 | 1/2006 | Bridger et al. | |
| 7,053,215 B2 | 5/2006 | Medina et al. | |
| 7,091,217 B2 | 8/2006 | Bridger et al. | |
| 7,135,570 B2 | 11/2006 | McEachern et al. | |
| 7,169,750 B2 | 1/2007 | Bridger et al. | |
| 7,291,631 B2 | 11/2007 | Bridger et al. | |
| 7,332,605 B2 | 2/2008 | Crawford et al. | |
| 7,354,932 B2 | 4/2008 | Bridger et al. | |
| 7,354,934 B2 | 4/2008 | Bridger et al. | |
| 7,452,994 B2 | 11/2008 | McEachern et al. | |
| 7,491,544 B2 | 2/2009 | Canary et al. | |
| 7,501,518 B2 | 3/2009 | Chen et al. | |
| 7,550,484 B2 | 6/2009 | Bridger et al. | |
| 7,592,351 B2 | 9/2009 | Sundermann et al. | |
| 7,723,525 B2 | 5/2010 | Crawford et al. | |
| 7,863,293 B2 | 1/2011 | Bridger et al. | |
| 7,897,590 B2 | 3/2011 | Bridger et al. | |
| 7,935,692 B2 | 5/2011 | Bridger et al. | |
| 8,168,783 B2 | 5/2012 | Kokubo et al. | |
| 8,178,123 B2 | 5/2012 | Pauletti et al. | |
| 8,778,967 B2 | 7/2014 | Bridger et al. | |
| 8,889,159 B2 | 11/2014 | Cleary et al. | |
| 8,906,682 B2 | 12/2014 | June et al. | |
| 9,119,790 B2 | 9/2015 | Crowley et al. | |
| 9,155,723 B2 | 10/2015 | Jain et al. | |
| 9,267,934 B2 | 2/2016 | Singh et al. | |
| 9,314,468 B2 | 4/2016 | Clark et al. | |

(Continued)

FOREIGN PATENT DOCUMENTS

EP   0434385 A2   6/1991
WO   WO-1997009976 A2   3/1997

(Continued)

OTHER PUBLICATIONS

Dr. Jean Donadieu, published on Oct. 2014 (Year: 2017).*
Dale et al (Curr Opin Hematol. Jan. 2017; 24(1): 46-53) (Year: 2017).*
"Common Terminology Criteria for Adverse Events (CTCAE), Version 4.0," U.S. Department of Health and Human Services, National Institutes of Health, National Cancer Institute, NIH Publication No. 09-5410, May 28, 2009, revised Jun. 2010 (196 pages).
"Nivolumab," Drugbank. Accessed Nov. 29, 2018: http://www.drugbank.ca/drugs/DB09035.
"Pembrolizumab," Drugbank Accession No. DB09037. Accessed Jan. 18, 2016: http://www.drugbank.ca/drugs/DB09037.
"SciFinder®," Search Results, American Chemical Society (ACS). 2015; 39 pages.

(Continued)

*Primary Examiner* — Jean P Cornet
(74) *Attorney, Agent, or Firm* — Dechert LLP; Joseph W. Arico; Matthew C. Stevens

(57) ABSTRACT

The present invention relates to methods of treating patients with neutropenia, such as severe, chronic neutropenia, or a related disorder, in which mavorixafor, or a pharmaceutically acceptable salt thereof, is administered to such patients. In some cases, the methods have the advantage of reducing or eliminating the need for administration of G-CSF, which is frequently associated with severe bone pain.

8 Claims, 9 Drawing Sheets

(56) References Cited

U.S. PATENT DOCUMENTS

| | | |
|---|---|---|
| 10,548,889 B1 | 2/2020 | Brands |
| 10,610,527 B2 | 4/2020 | Arbeit et al. |
| 10,953,003 B2 | 3/2021 | Ragan et al. |
| 11,045,461 B2 | 6/2021 | Brands |
| 11,219,621 B2 | 1/2022 | Arbeit et al. |
| 2003/0220341 A1 | 11/2003 | Bridger et al. |
| 2003/0232808 A1 | 12/2003 | Kobayashi et al. |
| 2007/0043012 A1 | 2/2007 | Bridger |
| 2007/0123538 A1 | 5/2007 | Dunkle et al. |
| 2007/0167459 A1 | 7/2007 | Habashita et al. |
| 2007/0232615 A1 | 10/2007 | Gudmundsson et al. |
| 2007/0259040 A1 | 11/2007 | Cherukuri |
| 2008/0045537 A1 | 2/2008 | Gudmundsson et al. |
| 2008/0058353 A1 | 3/2008 | Banks |
| 2008/0096861 A1 | 4/2008 | Gudmundsson et al. |
| 2008/0167341 A1 | 7/2008 | Bridger et al. |
| 2008/0171740 A1 | 7/2008 | Gudmundsson et al. |
| 2009/0203533 A1 | 8/2009 | Munnes et al. |
| 2009/0247570 A1 | 10/2009 | Mayer |
| 2009/0325877 A1 | 12/2009 | Grunt et al. |
| 2010/0002272 A1 | 1/2010 | Sato et al. |
| 2010/0022724 A1 | 1/2010 | Jacobsen et al. |
| 2010/0028299 A1 | 2/2010 | Einav et al. |
| 2010/0143301 A1 | 6/2010 | Desai et al. |
| 2011/0206607 A1 | 8/2011 | Olsson et al. |
| 2011/0293521 A1 | 12/2011 | Hyde et al. |
| 2012/0041028 A1 | 2/2012 | Cooper et al. |
| 2012/0141471 A1 | 6/2012 | Salvino et al. |
| 2013/0216531 A1 | 8/2013 | Jain et al. |
| 2014/0170677 A1 | 6/2014 | Klinguer-Hamour et al. |
| 2014/0275260 A1 | 9/2014 | Kawale et al. |
| 2015/0004239 A1 | 1/2015 | Cullen et al. |
| 2015/0030561 A1 | 1/2015 | Dale et al. |
| 2015/0037328 A1 | 2/2015 | Liu et al. |
| 2015/0216843 A1 | 8/2015 | Fearon |
| 2015/0246019 A1 | 9/2015 | Bridger et al. |
| 2015/0301058 A1 | 10/2015 | Schettini et al. |
| 2015/0352208 A1 | 12/2015 | Fearon |
| 2016/0030536 A1 | 2/2016 | Weiner et al. |
| 2016/0089385 A1 | 3/2016 | Sherman et al. |
| 2016/0222465 A1 | 8/2016 | Treon et al. |
| 2016/0228413 A1 | 8/2016 | Bridger et al. |
| 2017/0090658 A1 | 3/2017 | Park et al. |
| 2017/0137401 A1 | 5/2017 | Cox et al. |
| 2017/0166591 A1 | 6/2017 | Ojima et al. |
| 2017/0234879 A1 | 8/2017 | Klinguer-Hamour et al. |
| 2017/0305951 A1 | 10/2017 | Magnani et al. |
| 2017/0333436 A1 | 11/2017 | Treon et al. |
| 2018/0228894 A1 | 8/2018 | Fearon |
| 2018/0369167 A1 | 12/2018 | Arbeit et al. |
| 2018/0369229 A1 | 12/2018 | Ragan et al. |
| 2019/0030023 A1 | 1/2019 | Arbeit et al. |
| 2019/0083485 A1 | 3/2019 | Arbeit et al. |
| 2019/0160051 A1 | 5/2019 | Arbeit |
| 2020/0123150 A1 | 4/2020 | Bourque et al. |
| 2020/0268739 A1 | 8/2020 | Arbeit et al. |
| 2021/0025895 A1 | 1/2021 | Wang et al. |

FOREIGN PATENT DOCUMENTS

| | | | |
|---|---|---|---|
| WO | WO-1999004794 A1 | 2/1999 | |
| WO | WO-1999031264 A1 | 6/1999 | |
| WO | WO-2000002870 A1 | 1/2000 | |
| WO | WO-2000022599 A1 | 4/2000 | |
| WO | WO-2000045814 A1 | 8/2000 | |
| WO | WO-2000056729 A1 | 9/2000 | |
| WO | WO-2001042241 A1 | 6/2001 | |
| WO | WO-2002022600 A2 | 3/2002 | |
| WO | WO-2002034745 A1 | 5/2002 | |
| WO | WO-2002076948 A1 | 10/2002 | |
| WO | WO-2003011277 A3 | 2/2003 | |
| WO | WO-2003055876 A1 | 7/2003 | |
| WO | WO-2004019973 A1 | 3/2004 | |
| WO | WO-2004093817 A2 | 11/2004 | |
| WO | WO-2004106493 A2 | 12/2004 | |
| WO | WO-2006026703 A2 | 3/2006 | |
| WO | WO-2006036816 A2 | 4/2006 | |
| WO | WO-2006096444 A2 | 9/2006 | |
| WO | WO-2006138259 A2 | 12/2006 | |
| WO | WO-2007008539 A2 | 1/2007 | |
| WO | WO-2007027999 A2 | 3/2007 | |
| WO | WO-2007087548 A2 | 8/2007 | |
| WO | WO-2009026251 A1 | 2/2009 | |
| WO | WO-2009117706 A2 | 9/2009 | |
| WO | WO-2010086185 A1 | 8/2010 | |
| WO | WO-2011147026 A2 | 12/2011 | |
| WO | WO-2012049277 A1 | 4/2012 | |
| WO | WO-2012075362 A2 | 6/2012 | |
| WO | WO-2012094703 A1 | 7/2012 | |
| WO | WO-2015030853 A1 | 3/2015 | |
| WO | WO-2015038887 A1 | 3/2015 | |
| WO | WO-2015069770 A1 | 5/2015 | |
| WO | WO-2015134605 A1 | 9/2015 | |
| WO | WO-2015143012 A1 | 9/2015 | |
| WO | WO-2015200341 A1 | 12/2015 | |
| WO | WO-2016008976 A1 | 1/2016 | |
| WO | WO-2016094377 A1 | 6/2016 | |
| WO | WO-2016146261 A1 | 9/2016 | |
| WO | WO-2016201425 A1 | 12/2016 | |
| WO | WO-2017048702 A1 | 3/2017 | |
| WO | WO-2017106328 A1 | 6/2017 | |
| WO | WO-2017106332 A1 | 6/2017 | |
| WO | WO-2017112894 A1 * | 6/2017 | ........... A61K 31/395 |
| WO | WO-2017127811 A1 | 7/2017 | |
| WO | WO-2007087549 A2 | 8/2017 | |
| WO | WO-2017177230 A1 | 10/2017 | |
| WO | WO-2017181073 A1 | 10/2017 | |
| WO | WO-2018237158 A1 | 12/2018 | |
| WO | WO-2019094392 A1 | 5/2019 | |
| WO | WO-2019200223 A1 | 10/2019 | |
| WO | WO-2021127496 A1 | 6/2021 | |
| WO | WO-2021183650 A1 | 9/2021 | |

OTHER PUBLICATIONS

"SciFinder®," Search Results, American Chemical Society (ACS). 2015; 9 pages.

"Therapeutics," Encyclopedia Britannica Online. Accessed Nov. 6, 2018: https://www.britannica.com/science/therapeutics.

Abi-Younes et al., "The stromal cell-derived factor-1 chemokine is a potent platelet agonist highly expressed in atherosclerotic plaques," Circ Res. Feb. 4, 2000;86(2):131-8.

Acharyya et al., "A CXCL1 paracrine network links cancer chemoresistance and metastasis," Cell. Jul. 6, 2012; 150(1):165-78.

Aeglea Biotherapeutics, "A Multiple Dose, Dose Escalation Trial of AEB1102 in Patients With Advanced Solid Tumors," ClinicalTrials.gov: NCT02561234, First Posted: Sep. 28, 2015, Last Update: Mar. 22, 2019, https://clinicaltrials.gov/ct2/show/study/NCT02561234. Date Accessed, Mar. 25, 2019 (6 pages).

Aeglea Biotherapeutics, "A Multiple Dose, Dose Escalation Trial of AEB1102 in Patients With AML or MDS," ClinicalTrials.gov: NCT02732184, First Posted: Apr. 8, 2016, Last Update: Oct. 17, 2018, https://clinicaltrials.gov/ct2/show/study/NCT02732184. Date Accessed, Mar. 25, 2019 (6 pages).

Agenus Inc., "AGEN-1884, an Anti-CTLA-4 Antibody, in Advanced Solid Cancers," ClinicalTrials.gov: NCT02694822, First Posted: Mar. 1, 2016, Last Update: Jun. 27, 2017, https://clinicaltrials.gov/ct2/show/study/NCT02694822. Date Accessed, Mar. 25, 2019 (7 pages).

Aileron Therapeutics, "ALRN-6924 in Patients With Advanced Solid Tumors or Lymphomas," ClinicalTrials.gov: NCT02264613, First Posted: Oct. 15, 2014, Last Update: Jun. 27, 2017, https://clinicaltrials.gov/ct2/show/study/NCT02264613. Date Accessed, Mar. 25, 2019 (7 pages).

Aileron Therapeutics, "Safety Study of ALRN-6924 in Patients With Acute Myeloid Leukemia or Advanced Myelodysplastic Syndrome," ClinicalTrials.gov: NCT02909972, First Posted: Sep. 21, 2016, Last Update: Jun. 27, 2017, https://clinicaltrials.gov/ct2/show/study/NCT02909972. Date Accessed, Mar. 25, 2019 (7 pages).

(56) References Cited

OTHER PUBLICATIONS

Aiuti et al., "The chemokine SDF-1 is a chemoattractant for human CD34+ hematopoietic progenitor cells and provides a new mechanism to explain the mobilization of CD34+ progenitors to peripheral blood," J Exp Med. Jan. 6, 1997;185(1):111-20.
ALX Oncology Inc., "A Study of ALX148 in Patients With Advanced Solid Tumors and Lymphoma," ClinicalTrials.gov: NCT03013218, First Posted: Jan. 6, 2017, Last Update: Aug. 8, 2018, https://clinicaltrials.gov/ct2/show/study/NCT03013218. Date Accessed, Mar. 18, 2019 (6 pages).
Ami and Ohrui, "Lipase-catalyzed Kinetic Resolution of (±)-trans- and cis-2-Azidocycloalkanols," Biosci Biotechnol Biochem. 1999;63(12):2150-6.
An et al., "Solution phase combinatorial chemistry. Discovery of 13- and 15-membered polyazapyridinocyclophane libraries with antibacterial activity," Tetrahedron. 1998;54:3999-4012.
Andtbacka et al., "X4P-001, an Orally Bioavailable CXCR4 Antagonist, Increases T Cell Infiltration in Human Metastatic Melanoma," The Society for Immunotherapy of Cancer Annual Meeting. Nov. 8-12, 2017.
Anormed, "X4P 001," Drug Profile. Accessed Apr. 1, 2019: http://adisinsight.springer.com/drugs/800017499.
Arenberg et al., "The role of CXC chemokines in the regulation of angiogenesis in non-small cell lung cancer," J Leukoc Biol. Nov. 1997;62(5):554-62.
Ayers et al., "IFN-g-related mRNA profile predicts clinical response to PD-1 blockade," J Clin Invest. Aug. 1, 2017;127(8):2930-2940.
Azijli et al., "New developments in the treatment of metastatic melanoma: immune checkpoint inhibitors and targeted therapies," Anticancer Res. Apr. 2014;34(4):1493-506.
Baggiolini, "Chemokines and leukocyte traffic," Nature. Apr. 9, 1998;392(6676):565-8.
Bai et al., "Novel anti-inflammatory agents targeting CXCR4: Design, synthesis, biological evaluation and preliminary pharmacokinetic study", Eur J. Med Chem. Aug. 2017, vol. 136 pp. 360-371.
Bainton et al., "The development of neutrophilic polymorphonuclear leukocytes in human bone marrow." J Exp Med. Oct. 1, 1971, 134(4):907-34.
Balabanian et al., "Proper desensitization of CXCR4 is required for lymphocyte development and peripheral compartmentalization in mice," Blood. Jun. 14, 2012;119(24):5722-30.
Balabanian et al., "WHIM syndromes with different genetic anomalies are accounted for by impaired CXCR4 desensitization to CXCL12," Blood. Mar. 15, 2005;105(6): 2449-57.
Banka and Newman, "A clinical and molecular review of ubiquitous glucose-6-phosphatase deficiency caused by G6PC3 mutations." Orphanet J Rare Dis., 2013, 8:84.
Banka et al., "Variability of bone marrow morphology in G6PC3 mutations: is there a genotype-phenotype correlation or age-dependent relationship?" Am J Hematol. 2011, 86:235-7.
Banka, "G6PC3 deficiency: synonym: ubiquitous glucose-6-phosphatase deficiency." GeneReviews [internet] 2015; Adam et al., editors. Seattle WA: University of Washington, Seattle; 1993-2019.
Bayer, "Phase I Study of BAY1436032 in IDH1-mutant Advanced Solid Tumors," ClinicalTrials.gov: NCT02746081, First Posted: Apr. 21, 2016, Last Update: Mar. 19, 2019, https://clinicaltrials.gov/ct2/show/study/NCT02746081. Date Accessed, Mar. 25, 2019 (8 pages).
Beaussant-Cohen et al., "Description and outcome of a cohort of 8 patients with WHIM syndrome from the French Severe Chronic Neutropenia Registry," Orphanet Journal of Rare Diseases, vol. 7, No. 71, Jun. 14, 2012.
Berge et al., "Pharmaceutical salts," J Pharm Sci. Jan. 1977;66(1):1-19.
Blaak et al., "In vivo HIV-1 infection of CD45RA(+)CD4(+) T cells is established primarily by syncytium-inducing variants and correlates with the rate of CD4(+) T cell decline," Proc Natl Acad Sci U S A. Feb. 1, 2000;97(3):1269-74.

Blanco et al., "The CXCR4 antagonist AMD3100 efficiently inhibits cell-surface-expressed human immunodeficiency virus type 1 envelope-induced apoptosis," Antimicrob Agents Chemother. Jan. 2000;44(1):51-6.
Bleul et al., "B lymphocyte chemotaxis regulated in association with microanatomic localization, differentiation state, and B cell receptor engagement," J Exp Med. Mar. 2, 1998;187(5):753-62.
Bohinjec, "Myelokathexis: chronic neutropenia with hyperplastic bone marrow and hypersegmented neutrophils in two siblings," Blut. Mar. 1981;42(3):191-6.
Boutsikou et al., "Tumour necrosis factor, interferon-gamma and interleukins as predictive markers of antiprogrammed cell-death protein-1 treatment in advanced non-small cell lung cancer: a pragmatic approach in clinical practice," Therapeutic Advances in Medical Oncology, vol. 10, 2018 (pp. 1-8).
Boztug et al., "A syndrome with congenital neutropenia and mutations in G6PC3." N Engl J Med., 2009. 360:32-43.
Bristol-Myers Squibb, "A Phase I Open Label Study of the Safety and Tolerability of Elotuzumab (BMS-901608) Administered in Combination With Either Lirilumab (BMS-986015) or Urelumab (BMS-663513) in Subjects With Multiple Myeloma," ClinicalTrials.gov: NCT02252263, First Posted: Sep. 30, 2014, Last Update: Nov. 1, 2017, https://clinicaltrials.gov/ct2/show/study/NCT02252263. Date Accessed, Mar. 18, 2019 (7 pages).
Bristol-Myers Squibb, "An Investigational Immuno-therapy Study of Experimental Medication BMS-986178 by Itself or in Combination With Nivolumab and/or Ipilimumab in Patients With Solid Cancers That Are Advanced or Have Spread," ClinicalTrials.gov: NCT02737475, First Posted: Apr. 14, 2016, Last Update: Jan. 31, 2019, https://clinicaltrials.gov/ct2/show/study/NCT02737475. Date Accessed, Mar. 18, 2019 (11 pages).
Bristol-Myers Squibb, "An Investigational Immuno-therapy Study of Experimental Medication BMS-986179 Given Alone and in Combination With Nivolumab," ClinicalTrials.gov: NCT02754141, First Posted: Apr. 28, 2016, Last Update: Feb. 1, 2019, https://clinicaltrials.gov/ct2/show/study/NCT02754141. Date Accessed, Mar. 18, 2019 (8 pages).
Bristol-Myers Squibb, "An Investigational Immuno-Therapy Study to Determine the Safety and Effectiveness of Nivolumab and Daratumumab in Patients With Multiple Myeloma," ClinicalTrials.gov: NCT01592370, First Posted: May 7, 2012, Last Update: Jan. 15, 2019, https://clinicaltrials.gov/ct2/show/study/NCT01592370. Date Accessed, Mar. 18, 2019 (9 pages).
Bristol-Myers Squibb, "An Investigational Immuno-therapy Study to Evaluate the Safety and Effectiveness of Experimental Medication BMS-986207 by Itself and in Combination With Nivolumab in Solid Cancers That Are Advanced or Have Spread," ClinicalTrials.gov: NCT02913313, First Posted: Sep. 23, 2016, Last Update: Jan. 31, 2019, https://clinicaltrials.gov/ct2/show/study/NCT02913313. Date Accessed, Mar. 25, 2019 (9 pages).
Bristol-Myers Squibb, "An Investigational Immuno-therapy Study to Investigate the Safety and Effectiveness of Nivolumab, and Nivolumab Combination Therapy in Virus-associated Tumors (CheckMate358)," ClinicalTrials.gov: NCT02488759, First Posted: Jul. 2, 2015, Last Update: Oct. 19, 2018, https://clinicaltrials.gov/ct2/show/study/NCT02488759. Date Accessed Nov. 29, 2018 (7 pages).
Bristol-Myers Squibb, "Safety and Efficacy Study of Ulocuplumab and Nivolumab in Subjects With Solid Tumors (CXCessoR4)," ClinicalTrials.gov: NCT02472977, First Posted: Jun. 16, 2015, Last Update: Nov. 1, 2018, https://clinicaltrials.gov/ct2/show/study/NCT02472977. Date Accessed, Aug. 20, 2019 (7 pages).
Broxmeyer et al., "Effects of in vivo treatment with PIXY321 (GM-CSF/IL-3 fusion protein) on proliferation kinetics of bone marrow and blood myeloid progenitor cells in patients with sarcoma," Exp Hematol. Apr. 1995;23(4):335-40.
Broxmeyer et al., "Rapid mobilization of murine and human hematopoietic stem and progenitor cells with AMD3100, a CXCR4 antagonist." J Exp Med. 2005, 201(8):1307-18.
Broxmeyer, "A WHIM satisfactorily addressed," Blood. Apr. 1, 20140;123(15):2286-8.

(56) References Cited

OTHER PUBLICATIONS

Burger and Kipps, Burger et al. "CXCR4: a key receptor in the crosstalk between tumor cells and their microenvironment," Blood. Mar. 1, 2006;107(5):1761-7.

Burger et al., "Chronic lymphocytic leukemia B cells express functional CXCR4 chemokine receptors that mediate spontaneous migration beneath bone marrow stromal cells," Blood. Dec. 1, 1999;94(11):3658-67.

Canadian Cancer Trials Group, "Reolysin Combined With Docetaxel and Prednisone or Docetaxel and Prednisone Alone in Metastatic Castration Resistant Prostate Cancer," ClinicalTrials.gov: NCT01619813, First Posted: Jun. 14, 2012, Last Update: Jan. 23, 2019, https://clinicaltrials.gov/ct2/show/study/NCT01619813. Date Accessed, Mar. 25, 2019 (8 pages).

Canadian Cancer Trials Group, "Reolysin in Combination With FOLFOX6 and Bevacizumab or FOLFOX6 and Bevacizumab Alone in Metastatic Colorectal Cancer," ClinicalTrials.gov: NCT01622543 First Posted: Jun. 19, 2012, Last Update: Feb. 1, 2018, https://clinicaltrials.gov/ct2/show/study/NCT01622543. Date Accessed, Mar. 25, 2019 (8 pages).

Cao et al., "Effect of low-dose ritonavir on the pharmacokinetics of the CXCR4 antagonist AMD070 in healthy volunteers," Antimicrob Agents Chemother. May 2008;52(5):1630-4.

Cao et al., "The WHIM-like CXCR4(S338X) somatic mutation activates AKT and ERK, and promotes resistance to ibrutinib and other agents used in the treatment of Waldenstrom's Macroglobulinemia," Leukemia. Jan. 2015;29(1):169-76.

Castells et al., "Implication of tumor microenvironment in chemoresistance: tumor-associated stromal cells protect tumor cells from cell death," Int J Mol Sci. 2012;13(8):9545-71.

Catalano et al., "Synthesis of a novel tricyclic 1,2,3,4,4a,5,6,10b-octahydro-1,10-phenanthroline ring system and CXCR4 antagonists with potent activity against HIV-1," Bioorg Med Chem Lett. Apr. 1, 2010;20(7):2186-90.

Celgene, "A Safety and Efficacy Study of Oral AG-120 Plus Subcutaneous Azacitidine and Oral AG-221 Plus Subcutaneous Azacitidine in Subjects With Newly Diagnosed Acute Myeloid Leukemia (AML)," ClinicalTrials.gov: NCT02677922, First Posted: Feb. 9, 2016, Last Update: Feb. 21, 2019, https://clinicaltrials.gov/ct2/show/study/NCT02677922. Date Accessed, Mar. 20, 2019 (11 pages).

Celgene, "A Study of CC-90002 in Subjects With Acute Myeloid Leukemia (AML) and High-risk Myelodysplastic Syndrome (MDS)," ClinicalTrials.gov: NCT02641002, First Posted: Dec. 29, 2015, Last Update: Oct. 18, 2018, https://clinicaltrials.gov/ct2/show/study/NCT02641002. Date Accessed, Mar. 18, 2019 (7 pages).

Celgene, "An Efficacy and Safety Study of AG-221 (CC-90007) Versus Conventional Care Regimens in Older Subjects With Late Stage Acute Myeloid Leukemia Harboring an Isocitrate Dehydrogenase 2 Mutation (IDHENTIFY)," ClinicalTrials.gov: NCT02577406, First Posted: Oct. 16, 2015, Last Update: Feb. 21, 2019, https://clinicaltrials.gov/ct2/show/study/NCT02577406. Date Accessed, Mar. 25, 2019 (12 pages).

Celldex Therapeutics, "A Dose Escalation and Cohort Expansion Study of Anti-CD27 (Varlilumab) and Anti-PD-1 (Nivolumab) in Advanced Refractory Solid Tumors," ClinicalTrials.gov: NCT02335918, First Posted: Jan. 12, 2015, Last Update: Jan. 7, 2019, https://clinicaltrials.gov/ct2/show/study/NCT02335918. Date Accessed, Mar. 18, 2019 (9 pages).

Celldex Therapeutics, "A Study of CDX-1127 (Varlilumab) in Patients With Select Solid Tumor Types or Hematologic Cancers," ClinicalTrials.gov: NCT01460134, First Posted: Oct. 26, 2011, Last Update: Jan. 31, 2018, https://clinicaltrials.gov/ct2/show/study/NCT01460134. Date Accessed, Mar. 18, 2019 (9 pages).

Center for Biologics Evaluation and Research and Center for Drug Evaluation and Research "Q3C—Tables and List: Guidance for Industry," FDA Guidance Document. Aug. 2018;rev4.

Centre Leon Berard, "Evaluation of Safety and Activity of an Anti-PDL1 Antibody (DURVALUMAB) Combined With CSF-1R TKI (PEXIDARTINIB) in Patients With Metastatic/Advanced Pancreatic or Colorectal Cancers (MEDIPLEX)," ClinicalTrials.gov: NCT02777710, First Posted: May 19, 2016, Last Update: Jan. 17, 2019, https://clinicaltrials.gov/ct2/show/study/NCT02777710. Date Accessed, Mar. 18, 2019 (10 pages).

Chen et al., "CXCR4 inhibition in tumor microenvironment facilitates anti-programmed death receptor-1 immunotherapy in sorafenib-treated hepatocellular carcinoma in mice," Hepatology. May 2015;61(5):1591-602.

Chinook Therapeutics, Inc. (formerly Aduro Biotech, Inc.), "Safety and Efficacy of MIW815 (ADU-S100) +/- Ipilimumab in Patients With Advanced/Metastatic Solid Tumors or Lymphomas," ClinicalTrials.gov Identifier: NCT02675439. Accessed Apr. 13, 2022: https://clinicaltrials.gov/ct2/show/study/NCT02675439.

Chou and Mansfield, "Glucose-6-phosphate transporter: the key to glycogen storage disease type Ib." 2003, In: Broer and Wagner, editors. Membrane Transporter Diseases. New York: Springer; 191-205.

Chou et al., "Neutropenia in type 1b glycogen storage disease.", Curr Opin Hematol. 2010, 17:36-42.

Choueiri and Motzer, "Systemic Therapy for Metastatic Renal-Cell Carcinoma," N Engl J Med. Jan. 26, 2017;376(4):354-366.

Choueiri et al., "Combination Therapy with the CXCR4 Inhibitor X4P-001 and Nivolumab Demonstrates Preliminary Anti-tumor Activity in RCC Patients that are Unresponsive to Nivolumab Alone," ESMO Congress, Munich Germany. Oct. 19-23, 2018;poster.

Clark, "Rationale for targeted therapies and potential role of pazopanib in advanced renal cell carcinoma," Biologics. Jun. 26, 2010;4:187-97.

Cold Genesys, Inc., "Safety and Efficacy of CG0070 Oncolytic Virus Regimen for High Grade NMIBC After BCG Failure (BOND2)," ClinicalTrials.gov: NCT02365818, First Posted: Feb. 19, 2015, Last Update: Mar. 20, 2019, https://clinicaltrials.gov/ct2/show/study/NCT02365818. Date Accessed, Mar. 25, 2019 (9 pages).

Comba et al., "Catalytic Aziridination of Styrene with Copper Complexes of Substituted 3,7-Diazabicyclo[3.3.1]nonanones," Eur J Inorg Chem. 2003;9:1711-8.

Committee for Medicinal Products for Human Use (CHMP), "OPDIVO: International non-proprietaryname: nivolumab," European Medicines Agency (EMA) Assessment report. Apr. 23, 2015; EMA/CHMP/76688/2015.

Connolly et al., "Complexities of TGF-? targeted cancer therapy," Int J Biol Sci. 2012;8(7):964-78.

Connor and Ho, "Human immunodeficiency virus type 1 variants with increased replicative capacity develop during the asymptomatic stage before disease progression," J Virol. Jul. 1994;68(7):4400-8.

Courtney and Choueiri, "Optimizing recent advances in metastatic renal cell carcinoma," Curr Oncol Rep. May 2009;11(3):218-26.

Crawford et al., "AMD070, a CXCR4 Chemokine Receptor Antagonist: Practical Large-Scale Laboratory Synthesis," Org Process Res Dev. 2008;12(5):823-30.

Crispino and Horwitz, "GATA factor mutations in hematologic disease." Blood. 2017, 129:2103-10.

Crump et al., "Solution structure and basis for functional activity of stromal cell-derived factor-1; dissociation of CXCR4 activation from binding and inhibition of HIV-1," EMBO J. Dec. 1, 1997;16(23):6996-7007.

Curran et al., "PD-1 and CTLA-4 combination blockade expands infiltrating T cells and reduces regulatory T and myeloid cells within B16 melanoma tumors" PNAS, Mar. 2, 2010, vol. 107, No. 9, pp. 4275-4280.

D'Alterio et al., "Differential role of CD133 and CXCR4 in renal cell carcinoma," Cell Cycle. Nov. 15, 2010;9(22):4492-4500.

D'Alterio et al., "Inhibition of stromal CXCR4 impairs development of lung metastases," Cancer Immunol Immunother. Oct. 2012;61(10):1713-20.

Dale and Bolyard, "An update on the diagnosis and treatment of chronic idiopathic neutropenia." Curr Opin Hematol. 2017. 24:46-53.

Dale et al. "Neutropenia in glycogen storage disease Ib: outcomes for patients treated with granulocyte colony-stimulating factor". Jan. 2019. Curr Opin Hematol. 26:16-21.

(56) References Cited

OTHER PUBLICATIONS

Dale et al., "A randomized controlled phase III trial of recombinant human granulocyte colony-stimulating factor (filgrastim) for treatment of severe chronic neutropenia." Blood, 1993, 81:2496-502.

Dale et al., "Effects of granulocyte-macrophage colony-stimulating factor (GM-CSF) on neutrophil kinetics and function in normal human volunteers," Am J Hematol. Jan. 1998;57(1):7-15.

Dale et al., "Results of a phase 2 trial of an oral CXCR4 antagonist, mavorixafor, for treatment of WHIM syndrome," Blood. Dec. 2, 20204;136(26):2994-3003.

Dale et al., "The CXCR4 antagonist plerixafor is a potential therapy for myelokathexis, WHIM syndrome," Blood. Nov. 3, 2011;118(18):4963-6.

Dale et al., "The Severe Chronic Neutropenia International Registry: 10-Year Follow-up Report," Support Cancer Ther. Jul. 1, 2006;3(4):220-31.

Dana-Farber Cancer Institute, "LY3022855 With BRAF/MEK Inhibition in Patients With Melanoma," ClinicalTrials.gov: NCT03101254, First Posted: Apr. 5, 2017, Last Update: Feb. 4, 2019, https://clinicaltrials.gov/ct2/show/study/NCT03101254. Date Accessed, Mar. 18, 2019 (9 pages).

Debnath et al., "Small molecule inhibitors of CXCR4," Theranostics. 2013;3(1):47-75.

DePrimo et al., "Circulating protein biomarkers of pharmacodynamic activity of sunitinib in patients with metastatic renal cell carcinoma: modulation of VEGF and VEGF-related proteins," J Transl Med. Jul. 2, 2007;5:32.

Doranz et al., "Chemokine receptors as fusion cofactors for human immunodeficiency virus type 1 (HIV-1)," Immunol Res. Feb. 1997;16(1):15-28.

Dotta et al., "Clinical and genetic features of Warts, Hypogammaglobulinemia, Infections and Myelokathexis (WHIM) syndrome," Curr Mol Med. Jun. 2011;11(4):317-25.

Dresch et al. "Kinetic studies of 51Cr and DF32P labelled granulocytes." Br J Haematol. Jan. 1975. 29(1):67-80.

Duda et al., "CXCL12 (SDF1alpha)-CXCR4/CXCR7 pathway inhibition: an emerging sensitizer for anticancer therapies?" Clin Cancer Res. Apr. 15, 2011;17(8):2074-80.

Dudley et al., "CD8+ enriched 'young' tumor infiltrating lymphocytes can mediate regression of metastatic melanoma," Clin Cancer Res. Dec. 1, 20105;16(24):6122-31.

Duha Fahham MSc et al., In vitro and in vivo therapeutic efficacy of CXCR4 antagonist BKT140 against human non-small cell lung cancer, "The journal of thoracic and cardiovascular surgery," 2012, vol. 144, No. 5.

Dörwald, "Side Reactions in Organic Synthesis: A Guide to Successful Synthesis Design," Wiley: VCH Verlag Gmbh & Co. 2005;IX, 1-15, 41.

Eash et al., "CXCR4 is a key regulator of neutrophil release from the bone marrow under basal and stress granulopoiesis conditions." Blood. 2009, 113:4711-19.

Egberink et al., "Bicyclams, selective antagonists of the human chemokine receptor CXCR4, potently inhibit feline immunodeficiency virus replication," J Virol. Aug. 1999;73(8):6346-52.

Eli Lilly and Company, "A Study of LY3022855 in Combination With Durvalumab or Tremelimumab in Participants With Advanced Solid Tumors," ClinicalTrials.gov: NCT02718911, First Posted: Mar. 24, 2016, Last Update: Jan. 15, 2019, https://clinicaltrials.gov/ct2/show/study/NCT02718911. Date Accessed, Mar. 18, 2019 (7 pages).

Eli Lilly and Company, "A Study of LY3321367 Alone or With LY3300054 in Participants With Advanced Relapsed/Refractory Solid Tumors," ClinicalTrials.gov: NCT03099109, First Posted: Apr. 4, 2017, Last Update: Mar. 5, 2019, https://clinicaltrials.gov/ct2/show/study/NCT03099109. Date Accessed, Mar. 25, 2019 (10 pages).

EMD Serono Research & Development Institute, Inc., "MSB0011359C (M7824) in Metastatic or Locally Advanced Solid Tumors," ClinicalTrials.gov: NCT02517398, First Posted: Aug. 7, 2015, Last Update: Nov. 19, 2018, https://clinicaltrials.gov/ct2/show/study/NCT02517398. Date Accessed, Mar. 25, 2019 (8 pages).

European Medicines Agency, "Background review for sodium laurilsulfate used as an excipient," Jul. 23, 2015; EMA/CHMP/351898/2014.

Facciabene et al., "Tumour hypoxia promotes tolerance and angiogenesis via CCL28 and T(reg) cells," Nature. Jul. 13, 2011;475(7355):226-30.

FDA, FDA Drug development and drug interactions: table of substrates, inhibitors and inducers. Updated Nov. 14, 2017. Available at fda.gov/drugs/drug-interactions-labeling/drug-development-and-drug-interactions-table-substrates-inhibitors-and-inducers. Accessed Jun. 22, 2019.

Fedyk et al., "Maturation decreases responsiveness of human bone marrow B lineage cells to stromal-derived factor 1 (SDF-1)," J Leukoc Biol. Oct. 1999;66(4):667-73.

Feig et al., "Targeting CXCL12 from FAP-expressing carcinoma-associated fibroblasts synergizes with anti-PD-L1 immunotherapy in pancreatic cancer," Proc Natl Acad Sci U S A. Dec. 10, 2013;110(50):20212-7.

Ferguson, "Antihistamine for G-CSF-Induced Bone Pain", Pract Pain Manag. ; 15(6). online at: practical painmanagement.com/treatments/pharmacological/non-opioids/antihistamine-g-csf-induced-bone-pain.

Finke et al., "MDSC as a mechanism of tumor escape from sunitinib mediated anti-angiogenic therapy," Int Immunopharmacol. Jul. 2011;11(7):856-61.

Forty Seven, Inc., "CAMELLIA: Anti-CD47 Antibody Therapy in Haematological Malignancies," ClinicalTrials.gov: NCT02678338, First Posted: Feb. 9, 2016, Last Update: Feb. 21, 2019, https://clinicaltrials.gov/ct2/show/study/NCT02678338. Date Accessed, Mar. 18, 2019 (5 pages).

Forty Seven, Inc., "Trial of Hu5F9-G4 in Combination With Rituximab in Relapsed/Refractory B-cell Non-Hodgkin's Lymphoma," ClinicalTrials.gov: NCT02953509, First Posted: Nov. 2, 2016, Last Update: Feb. 8, 2019, https://clinicaltrials.gov/ct2/show/study/NCT02953509. Date Accessed, Mar. 18, 2019 (8 pages).

Gacche, "Compensatory angiogenesis and tumor refractoriness," Oncogenesis. Jun. 1, 2015;4(6):e153.

Gale and McColl, "Chemokines: extracellular messengers for all occasions?" Bioessays. Jan. 1999;21(1):17-28.

Galsky et al., "A phase I trial of LY2510924, a CXCR4 peptide antagonist, in patients with advanced cancer," Clin Cancer Res. Jul. 1, 2014;20(13):3581-8.

Gao et al., "Intratumoral balance of regulatory and cytotoxic T cells is associated with prognosis of hepatocellular carcinoma after resection," J Clin Oncol. Jun. 20, 2007;25(18):2586-93.

Gassenmaier et al., "CXC chemokine receptor 4 is essential for maintenance of renal cell carcinoma-initiating cells and predicts metastasis," Stem Cells. Aug. 2013;31(8):1467-76.

Genelux Corporation, "GL-ONC1 Oncolytic Immunotherapy in Patients With Recurrent or Refractory Ovarian Cancer," ClinicalTrials.gov: NCT02759588, First Posted: May 3, 2016, Last Update: Nov. 8, 2018, https://clinicaltrials.gov/ct2/show/study/NCT02759588. Date Accessed, Mar. 25, 2019 (8 pages).

Genelux GmbH, "A Study of GL-ONC1, an Oncolytic Vaccinia Virus, in Patients With Advanced Peritoneal Carcinomatosis," ClinicalTrials.gov: NCT01443260, First Posted: Sep. 29, 2011, Last Update: Mar. 10, 2015, https://clinicaltrials.gov/ct2/show/study/NCT01443260. Date Accessed, Mar. 25, 2019 (6 pages).

Genzyme, a Sanofi Company, "Safety and Efficacy Study of GC1008 to Treat Renal Cell Carcinoma or Malignant Melanoma," ClinicalTrials.gov: NCT00356460, First Posted: Jul. 26, 2006, Last Update: Mar. 19, 2014, https://clinicaltrials.gov/ct2/show/study/NCT00356460. Date Accessed, Mar. 25, 2019 (10 pages).

Gilead Sciences, "Study of Magrolimab (Hu5F9-G4) in Combination With Cetuximab in Participants With Solid Tumors and Advanced Colorectal Cancer," ClinicalTrials.gov Identifier: NCT02953782. First Posted Nov. 3, 2016; Accessed Aug. 3, 2021: https://clinicaltrials.gov/ct2/show/study/NCT02953782.

Glaspy et al., "Peripheral blood progenitor cell mobilization using stem cell factor in combination with filgrastim in breast cancer patients," Blood. Oct. 15, 1997;90(8):2939-51.

(56) References Cited

OTHER PUBLICATIONS

Glassman and Balthasar, "Mechanistic considerations for the use of monoclonal antibodies for cancer therapy," Cancer Biol Med. Mar. 2014;11(1):20-33.
Glaxosmithkline, "Dose Escalation and Expansion Study of GSK3359609 in Subjects With Selected Advanced Solid Tumors (INDUCE-1)," ClinicalTrials.gov: NCT02723955, First Posted: Mar. 31, 2016, Last Update: Feb. 25, 2019, https://clinicaltrials.gov/ct2/show/study/NCT02723955. Date Accessed, Mar. 18, 2019 (25 pages).
Glaxosmithkline, "GSK3174998 Alone or With Pembrolizumab in Subjects With Advanced Solid Tumors (ENGAGE-1)," ClinicalTrials.gov: NCT02528357, First Posted: Aug. 19, 2015, Last Update: Jun. 1, 2018, https://clinicaltrials.gov/ct2/show/study/NCT02528357. Date Accessed, Mar. 18, 2019 (11 pages).
Goldman et al., "Hyperglycemia associated with targeted oncologic treatment: mechanisms and management." Oncologist. Jul. 29, 2016. 21:1326-36.
Gonzalo et al., "Critical involvement of the chemotactic axis CXCR4/stromal cell-derived factor-1 alpha in the inflammatory component of allergic airway disease," J Immunol. Jul. 1, 2000;165(1):499-508.
Gravina et al., "The novel CXCR4 antagonist, PRX177561, reduces tumor cell proliferation and accelerates cancer stem cell differentiation in glioblastoma preclinical models," Tumour Biol. Jun. 2017;39(6):1010428317695528.
Greenberg et al., "The Chronic Idiopathic Neutropenia Syndrome: Correlation of Clinical Features With In Vitro Parameters of Granulocytopoiesis", Blood, Jun. 1, 1980, 55(6):915-921.
Gudmundsson et al., "Amine substituted N-(1H-benzimidazol-2ylmethyl)-5,6,7,8-tetrahydro-8-quinolinamines as CXCR4 antagonists with potent activity against HIV-1," Bioorg Med Chem Lett. Sep. 1, 2009;19(17):5048-52.
Gulino et al., "Altered leukocyte response to CXCL12 in patients with warts hypogammaglobulinemia, infections, myelokathexis (WHIM) syndrome," Blood. Jul. 15, 2004;104(2):444-52.
H. Lee Moffitt Cancer Center and Research Institute, "Combining PD-1 Blockade, CD137 Agonism and Adoptive Cell Therapy for Metastatic Melanoma," ClinicalTrials.gov: NCT02652455, First Posted: Jan. 11, 2016, Last Update: Dec. 4, 2018, https://clinicaltrials.gov/ct2/show/study/NCT02652455. Date Accessed, Mar. 18, 2019 (9 pages).
Hainsworth et al., "A Randomized, Open-Label Phase 2 Study of the CXCR4 Inhibitor LY2510924 in Combination with Sunitinib Versus Sunitinib Alone in Patients with Metastatic Renal Cell Carcinoma (RCC)," Target Oncol. Oct. 2016;11(5):643-653.
Hamid et al., "Safety and tumor responses with lambrolizumab (anti-PD-1) in melanoma," N Engl J Med. Jul. 11, 2013;369(2):134-44.
Hayee et al. "G6PC3 mutations are associated with a major defect of glycosylation: a novel mechanism for neutrophil dysfunction." Glycobiology, 2011, 21(7):914-24.
Hendrix et al., "Pharmacokinetics and safety of AMD-3100, a novel antagonist of the CXCR-4 chemokine receptor, in human volunteers," Antimicrob Agents Chemother. Jun. 2000;44(6):1667-73.
Hendrix et al., "Safety, pharmacokinetics, and antiviral activity of AMD3100, a selective CXCR4 receptor inhibitor, in HIV-1 infection," J Acquir Immune Defic Syndr. Oct. 1, 2004;37(2):1253-62.
Hernandez et al., "Mutations in the chemokine receptor gene CXCR4 are associated with WHIM syndrome, a combined immunodeficiency disease," Nat Genet. May 2003;34(1):70-4.
Herr et al., "Detection and quantification of blood-derived CD8+ T lymphocytes secreting tumor necrosis factor alpha in response to HLA-A2.1-binding melanoma and viral peptide antigens," J Immunol Methods. May 27, 1996;191(2):131-42.
Herr et al., "The use of computer-assisted video image analysis for the quantification of CD8+ T lymphocytes producing tumor necrosis factor alpha spots in response to peptide antigens," J Immunol Methods. Apr. 25, 1997;203(2):141-52.
Hesselgesser et al., "CD-4-independent association between HIV-1 gp120 and CXCR4: functional chemokine receptors are expressed in human neurons," Current Biology, vol. 7, No. 2, Jan. 21, 1997 (pp. 112-121).
Hesselgesser et al., "Neuronal apoptosis inducted by HIV-1 gp120 and chemokine SDF-1? is mediated by the chemokine receptor CXCR4," Current Biology, vol. 8, No. 10, Apr. 27, 1998 (pp. 595-598).
Hickstein "HSCT for GATA2 deficiency across the pond." Blood. 2018, 131:1272-74.
Highfill et al., "Disruption of CXCR2-mediated MDSC tumor trafficking enhances anti-PD1 efficacy," Sci Transl Med. May 21, 2014;6(237):237ra67.
Hsu et al., "GATA2 deficiency." Curr. Opin. Allergy Clin. Immunol., Feb. 2015, 15(1):104-9.
Hughes et al., "HIF-2? downregulation in the absence of functional VHL is not sufficient for renal cell differentiation", Cancer Cell Int. Jun. 28, 2007;7:13.
Husain et al., "Tumor-derived lactate modifies antitumor immune response: effect on myeloid-derived suppressor cells and NK cells," J Immunol. Aug. 1, 2013;191(3):1486-95.
Immutep Australia Pty. Ltd., "Phase 1 Study of IMP321 (Eftilagimod Alpha) Adjuvant to Anti-PD-1 Therapy in Unresectable or Metastatic Melanoma (TACTI-mel)," ClinicalTrials.gov: NCT02676869, First Posted: Feb. 8, 2016, Last Update: Jan. 11, 2019, https://clinicaltrials.gov/ct2/show/study/NCT02676869. Date Accessed, Mar. 25, 2019 (6 pages).
Immutep S.A., "IMP321 (Eftilagimod Alpha) as Adjunctive to a Standard Chemotherapy Paclitaxel Metastatic Breast Carcinoma," ClinicalTrials.gov: NCT02614833, First Posted: Nov. 25, 2015, Last Update: Mar. 18, 2019, https://clinicaltrials.gov/ct2/show/study/NCT02614833. Date Accessed, Mar. 25, 2019 (9 pages).
Immutep S.A., "IMP321 Plus First-line Paclitaxel in Metastatic Breast Carcinoma," ClinicalTrials.gov: NCT00349934, First Posted: Jul. 10, 2006, Last Update: Jan. 7, 2010, https://clinicaltrials.gov/ct2/show/study/NCT00349934. Date Accessed, Mar. 25, 2019 (7 pages).
Incyte Biosciences International Sàrl, "An Open-Label, Dose-Escalation, Safety Study of INCAGN01876 in Subjects With Advanced or Metastatic Solid Tumors," ClinicalTrials.gov: NCT02697591, First Posted: Mar. 3, 2016, Last Update: Oct. 31, 2018, https://clinicaltrials.gov/ct2/show/study/NCT02697591. Date Accessed, Mar. 18, 2019 (6 pages).
Incyte Biosciences International Sàrl, "Phase 1/2 Study Exploring the Safety, Tolerability, and Efficacy of INCAGN01876 Combined With Immune Therapies in Advanced or Metastatic Malignancies," ClinicalTrials.gov: NCT03126110, First Posted: Apr. 24, 2017, Last Update: Dec. 10, 2018, https://clinicaltrials.gov/ct2/show/study/NCT03126110. Date Accessed, Mar. 18, 2019 (7 pages).
Innate Pharma, "Combination Study of IPH2201 With Ibrutinib in Patients With Relapsed, Refractory or Previously Untreated Chronic Lymphocytic Leukemia," ClinicalTrials.gov: NCT02557516, First Posted: Sep. 23, 2015, Last Update: Apr. 24, 2018, https://clinicaltrials.gov/ct2/show/study/NCT02557516. Date Accessed, Mar. 20, 2019 (6 pages).
Innate Pharma, "Efficacy Study of Anti-KIR Monoclonal Antibody as Maintenance Treatment in Acute Myeloid Leukemia (EFFIKIR) (EFFIKIR)," ClinicalTrials.gov: NCT01687387, First Posted: Sep. 18, 2012, Last Update: Feb. 8, 2019, https://clinicaltrials.gov/ct2/show/study/NCT01687387. Date Accessed, Mar. 18, 2019 (9 pages).
Innate Pharma, "Study of IPH4102 in Patients With Relapsed/Refractory Cutaneous T-cell Lymphomas (CTCL)," ClinicalTrials.gov: NCT02593045, First Posted: Oct. 30, 2015, Last Update: Feb. 12, 2019, https://clinicaltrials.gov/ct2/show/study/NCT02593045. Date Accessed, Mar. 18, 2019 (6 pages).
Innate Pharma, "Study of Monalizumab and Cetuximab in Patients With Recurrent or Metastatic Squamous Cell Carcinoma of the Head and Neck," ClinicalTrials.gov: NCT02643550, First Posted: Dec. 31, 2015, Last Update: Sep. 13, 2018, https://clinicaltrials.gov/ct2/show/study/NCT02643550. Date Accessed, Mar. 20, 2019 (9 pages).
Innate Pharma, "Study on the Anti-tumor Activity, Safety and Pharmacology of IPH2101 in Patients With Smoldering Multiple

(56) References Cited

OTHER PUBLICATIONS

Myeloma (KIRMONO)," ClinicalTrials.gov: NCT01222286, First Posted: Oct. 18, 2010, Last Update: May 9, 2014, https://clinicaltrials.gov/ct2/show/study/NCT01222286. Date Accessed, Mar. 18, 2019 (7 pages).

Innate Pharma, "Study on the Safety, Anti-tumor Activity and Pharmacology of IPH2101 Combined With Lenalidomide in Patients With Multiple Myeloma Experiencing a First or Second Relapse (KIRIMID)," ClinicalTrials.gov: NCT01217203, First Posted: Oct. 8, 2010, Last Update: Feb. 28, 2014, https://clinicaltrials.gov/ct2/show/study/NCT01217203. Date Accessed, Mar. 18, 2019 (7 pages).

International Search Report from PCT/US2004/015977, dated Jun. 22, 2005.

Ishii et al., "Expression of stromal cell-derived factor-1/pre-B cell growth-stimulating factor receptor, CXC chemokine receptor 4, on CD34+ human bone marrow cells is a phenotypic alteration for committed lymphoid progenitors," J Immunol. Oct. 1, 1999;163(7):3612-20.

Iwakura et al., "AMD-3100, a CXCR4 Antagonist, Augments Incorporation of Bone Marrow-Derived Eendothelial Progenitor Cells into Sites of Myocardial Neovascularization," Abstract # 1127, Poster Board #-Session: 293I , Blood, vol. 100, No. 11, Nov. 16, 2002 (pp. 293A-294A).

Jackson et al., "Regeneration of ischemic cardiac muscle and vascular endothelium by adult stem cells," J Clin Invest. Jun. 2001; 107(11):1395-402.

Jacobson et al., "PET of Tumor CXCR4 Expression with 4-18F-T140", Nuclear Med., Nov. 2010, vol. 51, No. 11, pp. 1796-1804.

Jennerex Biotherapeutics, "A Study of Recombinant Vaccinia Virus to Treat Malignant Melanoma," ClinicalTrials.gov: NCT00429312, First Posted: Jan. 31, 2007, Last Update: Jan. 15, 2015, https://clinicaltrials.gov/ct2/show/study/NCT00429312. Date Accessed, Mar. 25, 2019 (7 pages).

Jones et al., "CXCR chemokine receptor engagement modifies integrin dependent adhesion of renal carcinoma cells", Experimental Cell Research, 2007, vol. 313, p. 4051-4065.

Jounce Therapeutics, Inc., "JTX-2011 Alone and in Combination With Anti-PD-1 or Anti-CTLA-4 in Subjects With Advanced and/or Refractory Solid Tumors (ICONIC)," ClinicalTrials.gov: NCT02904226, First Posted: Sep. 16, 2016, Last Update: Jun. 28, 2018, https://clinicaltrials.gov/ct2/show/study/NCT02904226. Date Accessed, Mar. 18, 2019 (11 pages).

Kashyap et al., "Ulocuplumab (BMS-936564 / MDX1338): a fully human anti-CXCR4 antibody induces cell death in chronic lymphocytic leukemia mediated through a reactive oxygen species-dependent pathway," Oncotarget. Jan. 19, 2016;7(3):2809-22.

Kawai and Malech, "WHIM syndrome: congenital immune deficiency disease," Curr Opin Hematol. Jan. 2009; 16(1):20-6.

Kawai et al., "Enhanced function with decreased internalization of carboxy-terminus truncated CXCR4 responsible for WHIM syndrome," Exp Hematol. Apr. 2005;33(4):460-8.

Kawai et al., "WHIM syndrome myelokathexis reproduced in the NOD/SCID mouse xenotransplant model engrafted with healthy human stem cells transduced with C-terminus-truncated CXCR4," Blood. Jan. 1, 2007;109(1):78-84.

Kim et al., "CXCR4 signaling regulates metastasis of chemoresistant melanoma cells by a lymphatic metastatic niche," Cancer Res. Dec. 15, 2010;70(24):10411-21.

Kim et al., "G-CSF down-regulation of CXCR3 expression identified as a mechanism for mobilization of myeloid cells." Blood. 2006, 108:812-20.

Kim et al., "Neutrophil stress and apoptosis underlie myeloid dysfunction in glycogen storage disease type Ib." Blood. 2008, 111(12):5704-11.

King et al., "Rapid mobilization of murine hematopoietic stem cells with enhanced engraftment properties and evaluation of hematopoietic progenitor cell mobilization in rhesus monkeys by a single injection of SB-251353, a specific truncated form of the human CXC chemokine GRObeta," Blood. Mar. 15, 2001;97(6):1534-42.

Kirkland et al., "Quantitation of mafosfamide-resistant pre-colony-forming units in allogeneic bone marrow transplantation: relationship with rate of engraftment and evidence for long-lasting reduction in stem cell numbers," Blood. May 1, 1996;87(9):3963-9.

Kirshner et al. "Prevention of Pegfilgrastim-Induced Bone Pain: A Phase III Double-Blind Placebo-Controlled Randomized Clinical Trial of the University of Rochester Cancer Center Clinical Community Oncology Program Research Base", J. Clin Oncol. Jun. 1, 2012. 30(16):1974-79.

Kocher et al., "Neovascularization of ischemic myocardium by human bone-marrow-derived angioblasts prevents cardiomyocyte apoptosis, reduces remodeling and improves cardiac function," Nat Med. Apr. 2001;7(4):430-6.

Kyle and Linman, "Chronic Idiopathic Neutropenia—A Newly Recognized Entity?", N Engl J Med. Nov. 7, 1968;279(19):1015-9.

Lagane et al., "CXCR4 dimerization and beta-arrestin-mediated signaling account for the enhanced chemotaxis to CXCL12 in WHIM syndrome," Blood. Jul. 1, 2008;112(1):34-44.

Lambertini et al. "The five "Ws" for bone pain due to the administration of granulocyte-colony stimulating factors (G-CSFs)", Crit. Rev. Oncol. Hematol. Jan. 2014. 89(1):112-128.

Langan et al., "Liver directed therapy for renal cell carcinoma," J Cancer. 2012;3:184-90.

Lapidot and Kollet, "The essential roles of the chemokine SDF-1 and its receptor CXCR4 in human stem cell homing and repopulation of transplanted immune-deficient NOD/SCID and NOD/SCID/B2m(null) mice," Leukemia. Oct. 2002;16(10):1992-2003.

Lapidot and Petit, "Current understanding of stem cell mobilization: the roles of chemokines, proteolytic enzymes, adhesion molecules, cytokines, and stromal cells," Exp Hematol. Sep. 2002;30(9):973-81.

Lataillade et al., "Chemokine SDF-1 enhances circulating CD34(+) cell proliferation in synergy with cytokines: possible role in progenitor survival," Blood. Feb. 1, 2000;95(3):756-68.

Leap Therapeutics, Inc., "Phase 1 Open-label Study of TRX518 Monotherapy and TRX518 in Combination With Gemcitabine, Pembrolizumab, or Nivolumab," ClinicalTrials.gov: NCT02628574, First Posted: Dec. 11, 2015, Last Update: Jan. 17, 2018, https://clinicaltrials.gov/ct2/show/study/NCT02628574. Date Accessed, Mar. 18, 2019 (8 pages).

Leap Therapeutics, Inc., "Trial of TRX518 (Anti-GITR mAb) in Stage III or IV Malignant Melanoma or Other Solid Tumors (TRX518-001)," ClinicalTrials.gov: NCT01239134, First Posted: Nov. 11, 2010, Last Update: Aug. 14, 2018, https://clinicaltrials.gov/ct2/show/study/NCT01239134. Date Accessed, Mar. 18, 2019 (8 pages).

Lee et al., "Coreceptor/chemokine receptor expression on human hematopoietic cells: biological implications for human immunodeficiency virus-type 1 infection," Blood. Feb. 15, 1999;93(4):1145-56.

Levesque et al., "Disruption of the CXCR4/CXCR12 chemotactic interaction during hematopoietic stem cell mobilization induced by G-CSF or cyclophosphamide." J Clin Invest. 2003, 111:187-96.

Li et al., "Design, synthesis, and structure-activity-relationship of a novel series of CXCR4 antagonists," Eur J Med Chem. Apr. 10, 2018;149:30-44.

Link. "Neutrophil homeostasis: a new role for stromal cell-derived factor-1." Immunol Res. 2005, 32:169-78.

Liu et al., "Homozygous defect in HIV-1 coreceptor accounts for resistance of some multiply-exposed individuals to HIV-1 infection," Cell. Aug. 9, 1996;86(3):367-77.

Lord et al., "Mobilization of early hematopoietic progenitor cells with BB-10010: a genetically engineered variant of human macrophage inflammatory protein-1 alpha," Blood. Jun. 15, 1995;85(12):3412-5.

Lord et al., "Myeloid cell kinetics in mice treated with recombinant interleukin-3, granulocyte colony-stimulating factor (GSF), or granulocyte-macrophage CSF in vivo." Blood. 1991, 77:2154-9.

Ludwig Institute for Cancer Research, "A Phase 1/2 Study of Motolimod (VTX-2337) and MEDI4736 in Subjects With Recurrent, Platinum-Resistant Ovarian Cancer for Whom Pegylated Liposomal Doxorubicin (PLD) is Indicated," ClinicalTrials.gov: NCT02431559,

(56) References Cited

OTHER PUBLICATIONS

First Posted: May 1, 2015, Last Update: Aug. 7, 2018, https://clinicaltrials.gov/ct2/show/study/NCT02431559. Date Accessed, Mar. 25, 2019 (9 pages).
Ludwig Institute for Cancer Research, "A Phase 1/2 Study to Investigate the Safety, Biologic and Anti-tumor Activity of ONCOS-102 in Combination With Durvalumab in Subjects With Advanced Peritoneal Malignancies," ClinicalTrials.gov: NCT02963831, First Posted: Nov. 15, 2016, Last Update: Mar. 18, 2019, https://clinicaltrials.gov/ct2/show/study/NCT02963831. Date Accessed, Mar. 25, 2019 (8 pages).
Lukacs et al., "AMD3100, a CxCR4 antagonist, attenuates allergic lung inflammation and airway hyperreactivity," Am J Pathol. Apr. 2002;160(4):1353-60.
Lundqvist et al., "31st Annual Meeting and Associated Programs of the Society for Immunotherapy of Cancer (SITC 2016): part one," J Immunother Cancer. Nov. 16, 2016;4(suppl 1):82.
Lycera Corp., "Study of LYC-55716 in Adult Subjects With Locally Advanced or Metastatic Cancer," ClinicalTrials.gov: NCT02929862, First Posted: Oct. 11, 2016, Last Update: May 7, 2018, https://clinicaltrials.gov/ct2/show/study/NCT02929862. Date Accessed, Mar. 25, 2019 (6 pages).
M.D. Anderson Cancer Center, "Lirilumab and Azacitidine in Treating Patients With Refractory or Relapsed Acute Myeloid Leukemia," ClinicalTrials.gov: NCT02399917, First Posted: Mar. 26, 2015, Last Update: Nov. 30, 2018, https://clinicaltrials.gov/ct2/show/study/NCT02399917. Date Accessed, Mar. 18, 2019 (8 pages).
M.D. Anderson Cancer Center, "Lirilumab and Nivolumab With 5-Azacitidine in Patients With Myelodysplastic Syndromes (MDS)," ClinicalTrials.gov: NCT02599649, First Posted: Nov. 6, 2015, Last Update: Feb. 1, 2019, https://clinicaltrials.gov/ct2/show/study/NCT02599649. Date Accessed, Mar. 18, 2019 (8 pages).
M.D. Anderson Cancer Center, "Lirilumab With Rituximab for Relapsed, Refractory or High-risk Untreated Chronic Lymphocytic Leukemia (CLL) Patients," ClinicalTrials.gov: NCT02481297, First Posted: Jun. 25, 2015, Last Update: Jul. 3, 2018, https://clinicaltrials.gov/ct2/show/study/NCT02481297. Date Accessed, Mar. 18, 2019 (7 pages).
M.D. Anderson Cancer Center, "Nivolumab and HPV-16 Vaccination in Patients With HPV-16 Positive Incurable Solid Tumors," ClinicalTrials.gov: NCT02426892, First Posted: Apr. 27, 2015, Last Update: Aug. 6, 2018, https://clinicaltrials.gov/ct2/show/NCT02426892. Date Accessed Nov. 29, 2018 (8 pages).
Ma et al., "The chemokine receptor CXCR4 is required for the retention of B lineage and granulocytic precursors within the bone marrow microenvironment," Immunity. Apr. 1999;10(4):463-71.
Maciejewski-Duval et al., "Altered chemotactic response to CXCL12 in patients carrying GATA2 mutations," J Leukoc Biol. Jun. 2016;99(6):1065-76.
Maekawa and Ishii, "Chemokine/receptor dynamics in the regulation of hematopoiesis," Intern Med. Feb. 2000;39(2):90-100.
Malkov et al., "Multiplexed measurements of gene signatures in different analytes using the Nanostring nCounter™ Assay System", BMC Research Notes; 2009, vol. 2, No. 80 accessed Nov. 2, 2017, https://bmcresnotes.biomedcentral.com/articles/10.1186/1756-0500-2-80.
Mardiana et al., "A Multifunctional Role for Adjuvant Anti-4-1BB Therapy in Augmenting Antitumor Response by Chimeric Antigen Receptor T Cells" Cancer Res. Mar. 2017, vol. 77, No. 6, pp. 1296-1309.
Matthys et al., "AMD3100, a potent and specific antagonist of the stromal cell-derived factor-1 chemokine receptor CXCR4, inhibits autoimmune joint inflammation in IFN-gamma receptor-deficient mice," J Immunol. Oct. 15, 2001;167(8):4686-92.
Maximilian Diehn, "SABR-ATAC: A Trial of TGF-beta Inhibition and Stereotactic Ablative Radiotherapy for Early Stage Non-small Cell Lung Cancer," ClinicalTrials.gov: NCT02581787, First Posted: Oct. 21, 2015, Last Update: Feb. 5, 2019, https://clinicaltrials.gov/ct2/show/study/NCT02581787. Date Accessed, Mar. 25, 2019 (7 pages).

McCormick et al., "Impaired recruitment of Grk6 and beta-Arrestin 2 causes delayed internalization and desensitization of a WHIM syndrome-associated CXCR4 mutant receptor," PLoS One. Dec. 1, 2009;4(12):e8102.
McDermott et al., "A phase 1 clinical trial of long-term, low-dose treatment of WHIM syndrome with the CXCR4 antagonist plerixafor," Blood. Apr. 10, 2014;123(15):2308-16.
McDermott et al., "Safety and efficacy of the oral CXCR4 inhibitor X4P-001 + axitinib in advanced renal cell carcinoma patients: An analysis of subgroup responses by prior treatment," Ann Oncol. Oct. 2019;30(suppl 5):v482-3(1186PD).
McDermott et al., "The CXCR4 antagonist plerixafor corrects panleukopenia in patients with WHIM syndrome, "Blood. Nov. 3, 2011;118(18):4957-62.
McDermott et al., "Severe congenital neutropenia resulting from G6PC3 deficiency with increased neutrophil CXCR4 expression and myelokathexis," Blood. Oct. 14, 2010;116(15):2793-802.
McDermott, D. "Whim Syndrome," National Organization for Rare Disorders, 2013, 2016, https://rarediseases.org/rare-diseases/whim-syndrome. Date Accessed Sep. 27, 2018.
McMahon, "VEGF receptor signaling in tumor angiogenesis," Oncologist. 2000;5 Suppl 1:3-10.
MedImmune LLC, "A Phase 1 Study of MEDI0562 in Adult Subjects With Selected Advanced Solid Tumors," ClinicalTrials.gov: NCT02318394, First Posted: Dec. 17, 2014, Last Update: Jan. 29, 2018, https://clinicaltrials.gov/ct2/show/study/NCT02318394. Date Accessed, Mar. 18, 2019 (7 pages).
MedImmune LLC, "A Study in Adult Subjects With Select Advanced Solid Tumors," ClinicalTrials.gov: NCT02583165, First Posted: Oct. 22, 2015, Last Update: Jan. 8, 2019, https://clinicaltrials.gov/ct2/show/study/NCT02583165. Date Accessed, Mar. 18, 2019 (7 pages).
MedImmune LLC, "A Study to Evaluate MEDI0562 in Combination With Immune Therapeutic Agents in Adult Subjects With Advanced Solid Tumors," ClinicalTrials.gov: NCT02705482, First Posted: Mar. 10, 2016, Last Update: Feb. 19, 2019, https://clinicaltrials.gov/ct2/show/study/NCT02705482. Date Accessed, Mar. 18, 2019 (10 pages).
MedImmune LLC, "MEDI9447 Alone and in Combination With MEDI4736 in Adult Subjects With Select Advanced Solid Tumors," ClinicalTrials.gov: NCT02503774, First Posted: Jul. 21, 2015, Last Update: Mar. 11, 2019, https://clinicaltrials.gov/ct2/show/study/NCT02503774. Date Accessed, Mar. 18, 2019 (8 pages).
Melis et al., "Involvement of endocrine system in a patient affected by Glycogen storage disease 1b: speculation on the role of autoimmunity" Italian J. Pediatrics. Mar. 19, 2014, 40:30.
Merck KGAA, Darmstadt, Germany, "MSB0011359C (M7824) in Subjects With Metastatic or Locally Advanced Solid Tumors," ; ClinicalTrials.gov: NCT02699515, First Posted: Mar. 4, 2016, Last Update: Sep. 12, 2018, https://clinicaltrials.gov/ct2/show/study/NCT02699515. Date Accessed, Mar. 25, 2019 (8 pages).
Merck Sharp & Dohme Corp., "Study of MK-1454 Alone or in Combination With Pembrolizumab in Participants With Advanced/Metastatic Solid Tumors or Lymphomas (MK-1454-001)," ClinicalTrials.gov: NCT03010176, First Posted: Jan. 4, 2017, Last Update: Mar. 15, 2019, https://clinicaltrials.gov/ct2/show/study/NCT03010176. Date Accessed, Mar. 18, 2019 (11 pages).
Merck Sharp & Dohme Corp., "Study of MK-4166 and MK-4166 in Combination With Pembrolizumab (MK-3475) in Participants With Advanced Solid Tumors (MK-4166-001)," ClinicalTrials.gov: NCT02132754, First Posted: May 7, 2014, Last Update: Sep. 24, 2018, https://clinicaltrials.gov/ct2/show/study/NCT02132754. Date Accessed, Mar. 18, 2019 (6 pages).
Michael et al., "Exclusive and persistent use of the entry coreceptor CXCR4 by human immunodeficiency virus type 1 from a subject homozygous for CCR5 delta32," J Virol. Jul. 1998;72(7):6040-7.
Miller et al., "Novel N-substituted benzimidazole CXCR4 antagonists as potential anti-HIV agents," Bioorg Med Chem Lett. Apr. 1, 2010;20(7):2125-8.
Miller et al., "Synthesis and SAR of novel isoquinoline CXCR4 antagonists with potent anti-HIV activity," Bioorg Med Chem Lett. May 15, 2010;20(10):3026-30.

(56) References Cited

OTHER PUBLICATIONS

Moch and Lukamowicz-Rajska. "miR-30c-2-3p and miR-30a-3p: New Pieces of the Jigsaw Puzzle in HIF2? Regulation", Cancer Discov (2014) 4 (1): 22-24.
Montane et al., "Prevention of murine autoimmune diabetes by CCL22-mediated Treg recruitment to the pancreatic islets," J Clin Invest. Aug. 2011;121(8):3024-8.
Morimoto et al., "Enhancement of the CXCL12/CXCR4 axis due to acquisition of gemcitabine resistance in pancreatic cancer: effect of CXCR4 antagonists," BMC Cancer. May 12, 2016;16:305.
Mosi et al., "The molecular pharmacology of AMD11070: an orally bioavailable CXCR4 HIV entry inhibitor," Biochem Pharmacol. Feb. 15, 2012;83(4):472-9.
Moskovits et al., "p53 Attenuates cancer cell migration and invasion through repression of SDF-1/CXCL12 expression in stromal fibroblasts," Cancer Res. Nov. 15, 2006;66(22):10671-6.
Motzer et al., "Nivolumab for Metastatic Renal Cell Carcinoma: Results of a Randomized Phase II Trial," J Clin Oncol. May 1, 2015;33(13):1430-7.
Motzer et al., "Nivolumab versus Everolimus in Advanced Renal-Cell Carcinoma," N Engl J Med. Nov. 5, 2015;373(19):1803-13.
Moyle et al., "Proof of activity with AMD11070, an orally bioavailable inhibitor of CXCR4-tropic HIV type 1," Clin Infect Dis. Mar. 15, 2009;48(6):798-805.
Mukhtar et al., "Targeting microtubules by natural agents for cancer therapy," Mol Cancer Ther. Feb. 2014;13(2):275-84.
Murdoch and Finn, "Chemokine receptors and their role in inflammation and infectious diseases," Blood. May 15, 2000;95(10):3032-43.
Nagaraj et al., "Altered recognition of antigen is a mechanism of CD8+ T cell tolerance in cancer," Nat Med. Jul. 2007;13(7):828-35.
Nagase et al., "Expression of CXCR4 in eosinophils: functional analyses and cytokine-mediated regulation," J Immunol. Jun. 1, 2000;164(11):5935-43.
Nanki and Lipsky, "Cutting edge: stromal cell-derived factor-1 is a costimulator for CD4+ T cell activation," J Immunol. May 15, 2000;164(10):5010-4.
Nash, "Allogeneic HSCT for autoimmune diseases: conventional conditioning regimens," Bone Marrow Transplant. Aug. 2003;32 Suppl 1:S77-80.
National Cancer Institute (NCI), "A Phase I Study of Intravenous Recombinant Human IL-15 in Adults With Refractory Metastatic Malignant Melanoma and Metastatic Renal Cell Cancer," ClinicalTrials. gov: NCT01021059, First Posted: Nov. 26, 2009, Last Update: Feb. 26, 2019, https://clinicaltrials.gov/ct2/show/study/NCT01021059. Date Accessed, Mar. 20, 2019 (9 pages).
National Cancer Institute (NCI), "Anti-ICOS Monoclonal Antibody MEDI-570 in Treating Patients With Relapsed or Refractory Peripheral T-cell Lymphoma Follicular Variant or Angioimmunoblastic T-cell Lymphoma," ClinicalTrials.gov: NCT02520791, First Posted: Aug. 13, 2015, Last Update: Feb. 6, 2019, https://clinicaltrials.gov/ct2/show/study/NCT02520791. Date Accessed, Mar. 18, 2019 (13 pages).
National Cancer Institute (NCI), "Part 2 of Phase 1 Study of GC1008 to Treat Advanced Melanoma (Part 2 Will Only Accept and Treat Patients With Advanced Malignant Melanoma)," ClinicalTrials. gov: NCT00923169, First Posted: Jun. 18, 2009, Last Update: Mar. 12, 2019, https://clinicaltrials.gov/ct2/show/study/NCT00923169. Date Accessed, Mar. 25, 2019 (8 pages).
National Cancer Institute (NCI), "Subcutaneous Recombinant Human IL-15 (s.c. rhIL-15) and Alemtuzumab for People With Refractory or Relapsed Chronic and Acute Adult T-cell Leukemia (ATL)," ClinicalTrials.gov: NCT02689453, First Posted: Feb. 24, 2016, Last Update: Mar. 20, 2019, https://clinicaltrials.gov/ct2/show/study/NCT02689453. Date Accessed, Mar. 20, 2019 (9 pages).
National Cancer Institute (NCI), "Trametinib and Navitoclax in Treating Patients With Advanced or Metastatic Solid Tumors," ClinicalTrials.gov: NCT02079740, First Posted: Mar. 6, 2014, Last Update: Feb. 6, 2019, https://clinicaltrials.gov/ct2/show/study/NCT02079740. Date Accessed, Mar. 25, 2019 (12 pages).
National Cancer Institute (NCI), "Use of IL-15 After Chemotherapy and Lymphocyte Transfer in Metastatic Melanoma," ClinicalTrials. gov: NCT01369888, First Posted: Jun. 9, 2011, Last Update: Jan. 27, 2015, https://clinicaltrials.gov/ct2/show/study/NCT01369888. Date Accessed, Mar. 20, 2019 (9 pages).
National Cancer Institute, "Nivolumab and Ipilimumab in Treating Patients With HIV Associated Relapsed or Refractory Classical Hodgkin Lymphoma or Solid Tumors That Are Metastatic or Cannot Be Removed by Surgery," ClinicalTrials.gov: NCT02408861, First Posted: Apr. 6, 2016, Last Update: Jun. 12, 2018, https://clinicaltrials.gov/ct2/show/study/NCT02408861. Date Accessed, Nov. 29, 2018 (13 pages).
National Cancer Institute, "Nivolumab in Treating Patients With HTLV-Associated T-Cell Leukemia/Lymphoma," ClinicalTrials. gov: NCT02631746, First Posted: Dec. 16, 2015, Last Update: Aug. 28, 2018, https://clinicaltrials.gov/ct2/show/study/NCT02631746. Date Accessed, Nov. 29, 2018 (9 pages).
Neumedicines Inc., "NM-IL-12 (rHuIL?12) In Relapsed/Refractory Diffuse Large B-Cell Lymphoma (DLBCL) Undergoing Salvage Chemotherapy," ClinicalTrials.gov: NCT02544724, First Posted: Sep. 9, 2015, Last Update: Aug. 3, 2016, https://clinicaltrials.gov/ct2/show/study/NCT02544724. Date Accessed, Mar. 20, 2019 (8 pages).
Neumedicines Inc., "NM-IL-12 in Cutaneous T-Cell Lymphoma (CTCL) Undergoing Total Skin Electron Beam Therapy (TSEBT)," ClinicalTrials.gov: NCT02542124, First Posted: Sep. 4, 2015, Last Update: Nov. 16, 2018, https://clinicaltrials.gov/ct2/show/study/NCT02542124. Date Accessed, Mar. 20, 2019 (8 pages).
Neves et al., "Ligand-guided optimization of CXCR4 homology models for virtual screening using a multiple chemotype approach," J Comput Aided Mol Des. Dec. 2010;24(12):1023-33.
Nicholas Butowski, "A Study of Varlilumab and IMA950 Vaccine Plus Poly-ICLC in Patients With WHO Grade II Low-Grade Glioma (LGG)," ClinicalTrials.gov: NCT02924038, First Posted: Oct. 5, 2016, Last Update: Mar. 6, 2019, https://clinicaltrials.gov/ct2/show/study/NCT02924038. Date Accessed, Mar. 18, 2019 (9 pages).
Novartis Pharmaceuticals, "A Phase I/Ib Study of NIZ985 in Combination With PDR001 in Adults With Metastatic Cancers," ClinicalTrials.gov: NCT02452268, First Posted: May 22, 2015, Last Update: Oct. 2, 2018, https://clinicaltrials.gov/ct2/show/study/NCT02452268. Date Accessed, Mar. 20, 2019 (7 pages).
Novartis Pharmaceuticals, "Phase I/Ib Study of GWN323 Alone and in Combination With PDR001 in Patients With Advanced Malignancies and Lymphomas," ClinicalTrials.gov: NCT02740270, First Posted: Apr. 15, 2016, Last Update: Feb. 18, 2019, https://clinicaltrials.gov/ct2/show/study/NCT02740270. Date Accessed, Mar. 28, 2019 (6 pages).
Novartis Pharmaceuticals, "Phase I/Ib Study of NIS793 in Combination With PDR001 in Patients With Advanced Malignancies.," ClinicalTrials.gov: NCT02947165, First Posted: Oct. 27, 2016, Last Update: Nov. 6, 2018, https://clinicaltrials.gov/ct2/show/study/NCT02947165. Date Accessed, Mar. 25, 2019 (9 pages).
Novartis Pharmaceuticals, "Phase I/II Study of BLZ945 Single Agent or BLZ945 in Combination With PDR001 in Advanced Solid Tumors," ClinicalTrials.gov: NCT02829723, First Posted: Jul. 12, 2016, Last Update: Jul. 12, 2018, https://clinicaltrials.gov/ct2/show/study/NCT02829723. Date Accessed, Mar. 18, 2019 (7 pages).
Novartis Pharmaceuticals, "Safety and Efficacy of MBG453 as Single Agent and in Combination With PDR001 in Patients With Advanced Malignancies," ClinicalTrials.gov: NCT02608268, First Posted: Nov. 18, 2015, Last Update: Oct. 2, 2018, https://clinicaltrials.gov/ct2/show/study/NCT02608268. Date Accessed, Mar. 25, 2019 (10 pages).
Novartis Pharmaceuticals, "Study of the Safety and Efficacy of MIW815 With PDR001 to Patients With Advanced/Metastatic Solid Tumors or Lymphomas," ClinicalTrials.gov: NCT03172936, First Posted: Jun. 1, 2017, Last Update: Feb. 18, 2019, https://clinicaltrials.gov/ct2/show/study/NCT03172936. Date Accessed, Mar. 18, 2019 (9 pages).
Nyunt et al., "Pharmacokinetic effect of AMD070, an Oral CXCR4 antagonist, on CYP3A4 and CYP2D6 substrates midazolam and dextromethorphan in healthy volunteers," J Acquir Immune Defic Syndr. Apr. 15, 2008;47(5):559-65.

(56) References Cited

OTHER PUBLICATIONS

O'Boyle et al., "Inhibition of CXCR4-CXCL12 chemotaxis in melanoma by AMD11070," Br J Cancer. Apr. 30, 2013;108(8):1634-40.
Ohagen et al., "Apoptosis induced by infection of primary brain cultures with diverse human immunodeficiency virus type 1 isolates: evidence for a role of the envelope," J Virol. Feb. 1999;73(2):897-906.
Okazaki et al., "A rheostat for immune responses: the unique properties of PD-1 and their advantages for clinical application," Nat Immunol. Dec. 2013;14(12):1212-8.
Oncolytics Biotech, "A Study of REOLYSIN® in Combination With Gemcitabine in Patients With Advanced Pancreatic Adenocarcinoma," ClinicalTrials.gov: NCT00998322, First Posted: Oct. 20, 2009, Last Update: Apr. 10, 2015, https://clinicaltrials.gov/ct2/show/study/NCT00998322. Date Accessed, Mar. 25, 2019 (6 pages).
Oncolytics Biotech, "Efficacy Study of REOLYSIN® in Combination With Paclitaxel and Carboplatin in Platinum-Refractory Head and Neck Cancers," ClinicalTrials.gov: NCT01166542, First Posted: Jul. 21, 2010, Last Update: Nov. 5, 2014, https://clinicaltrials.gov/ct2/show/study/NCT01166542. Date Accessed, Mar. 25, 2019 (7 pages).
Oncolytics Biotech, "Phase 2 Study of REOLYSIN® in Combination With Paclitaxel and Carboplatin for Non-Small Cell Lung Cancer With KRAS or EGFR Activation," ClinicalTrials.gov: NCT00861627, First Posted: Mar. 13, 2009, Last Update: Dec. 2, 2015, https://clinicaltrials.gov/ct2/show/study/NCT00861627. Date Accessed, Mar. 25, 2019 (7 pages).
OncoMed Pharmaceuticals, Inc., "A Study of OMP-313M32 in Subjects With Locally Advanced or Metastatic Solid Tumors," ClinicalTrials.gov: NCT03119428, First Posted: Apr. 18, 2017, Last Update: Dec. 7, 2018, https://clinicaltrials.gov/ct2/show/study/NCT03119428. Date Accessed, Mar. 25, 2019 (7 pages).
Panka et al., "Effects of HDM2 antagonism on sunitinib resistance, p53 activation, SDF-1 induction, and tumor infiltration by CD11b+/Gr-1+ myeloid derived suppressor cells," Mol Cancer. Mar. 5, 2013;12:17.
Panka et al., "MDSC trafficking and function in RCC by CXCR4 in the presence of a VEGF-R antagonist is dependent on HIF-2(alpha) expression," Eur J Cancer. 2016;69(1):S105.
Parameswaran et al., "Combination of drug therapy in acute lymphoblastic leukemia with a CXCR4 antagonist," Leukemia. Aug. 2011;25(8):1314-23.
Patnaik et al., "Phase I Study of Pembrolizumab (MK-3475; Anti-PD-1 Monoclonal Antibody) in Patients with Advanced Solid Tumors," Clin Cancer Res. Oct. 1, 2015;21(19):4286-93.
PCT International Preliminary Examination Report from PCT/US2002/041407, dated Jul. 17, 2003.
PCT International Preliminary Report on Patentability from PCT/US2004/015977, dated Apr. 1, 2006.
PCT International Search Report and Written Opinion from PCT/US2016/066634, dated Jan. 26, 2017.
PCT International Search Report and Written Opinion from PCT/US2016/066639, dated Jan. 20, 2017.
PCT International Search Report and Written Opinion from PCT/US2016/068394, dated Feb. 8, 2017.
PCT International Search Report and Written Opinion from PCT/US2017/014578, dated Mar. 21, 2017.
PCT International Search Report and Written Opinion from PCT/US2017/026819, dated Jun. 14, 2017.
PCT International Search Report and Written Opinion from PCT/US2018/038776, dated Oct. 29, 2018.
PCT International Search Report and Written Opinion from PCT/US2018/059482, dated Dec. 11, 2018.
PCT International Search Report and Written Opinion from PCT/US2019/027169, dated Jun. 20, 2019.
PCT International Search Report and Written Opinion from PCT/US2019/049065, dated Feb. 9, 2019.
PCT International Search Report from PCT/US2002/029372, dated Jul. 20, 2004.
PCT International Search Report from PCT/US2004/011328, dated Sep. 28, 2004.
PCT International Search Report from PCT/US2004/012627, dated Nov. 10, 2004.
PCT International Search Report from PCT/US2005/034491, dated Jan. 11, 2006.
PCT International Search Report from PCT/US2005/034950, dated May 10, 2006.
PCT International Search Report from PCT/US2005/08268, dated May 13, 2005.
Peled et al., "The chemokine SDF-1 activates the integrins LFA-1, VLA-4, and VLA-5 on immature human CD34(+) cells: role in transendothelial/stromal migration and engraftment of NOD/SCID mice," Blood. Jun. 1, 2000;95(11):3289-96.
Pfizer, "A Study of Avelumab in Combination With Other Cancer Immunotherapies in Advanced Malignancies (JAVELIN Medley)," ClinicalTrials.gov: NCT02554812, First Posted: Sep. 18, 2015, Last Update: Mar. 13, 2019, https://clinicaltrials.gov/ct2/show/study/NCT02554812. Date Accessed, Mar. 18, 2019 (13 pages).
Pfizer, "Avelumab in Combination Regimens That Include an Immune Agonist, Epigenetic Modulator, CD20 Antagonist and/or Conventional Chemotherapy in Patients With Relapsed or Refractory Diffuse Large B-cell Lymphoma (R/R DLBCL) (Javelin DLBCL)," ClinicalTrials.gov: NCT02951156, First Posted: Nov. 1, 2016, Last Update: Jan. 29, 2019, https://clinicaltrials.gov/ct2/show/study/NCT02951156. Date Accessed, Mar. 18, 2019 (11 pages).
Pike et al., "Nutrition: An Integrated Approach," Third Edition, John Wiley & Sons, 1984 (pp. 538-539).
Pillay et al., "In vivo labeling with 2H2O reveals a human neutrophil lifespan of 5.4 days." Blood. Jul. 29, 2010, 116(4):625-7.
Plexxikon, "A Combination Clinical Study of PLX3397 and Pembrolizumab to Treat Advanced Melanoma and Other Solid Tumors," ClinicalTrials.gov: NCT02452424, First Posted: May 22, 2015, Last Update: Nov. 15, 2018, https://clinicaltrials.gov/ct2/show/study/NCT02452424. Date Accessed, Mar. 18, 2019 (9 pages).
Ponath, "Chemokine receptor antagonists: novel therapeutics for inflammation and AIDS," Expert Opin Investig Drugs. 1998;7(1):1-18.
Portella et al., "Preclinical development of a novel class of CXCR4 antagonist impairing solid tumors growth and metastases," PLoS One. Sep. 13, 2013;8(9):e74548.
Providence Health & Services, "Anti-OX40 Antibody (MEDI6469) in Patients With Metastatic Colorectal Cancer," ClinicalTrials.gov: NCT02559024, First Posted: Sep. 24, 2015, Last Update: Oct. 10, 2018, https://clinicaltrials.gov/ct2/show/study/NCT02559024. Date Accessed, Mar. 18, 2019 (6 pages).
Providence Health & Services, "Anti-OX40 Antibody in Head and Neck Cancer Patients," ClinicalTrials.gov: NCT02274155, First Posted: Oct. 24, 2014, Last Update: Nov. 26, 2018, https://clinicaltrials.gov/ct2/show/study/NCT02274155. Date Accessed, Mar. 18, 2019 (6 pages).
Providence Health & Services, "Anti-OX40, Cyclophosphamide (CTX) and Radiation in Patients With Progressive Metastatic Prostate Cancer," ClinicalTrials.gov: NCT01303705, First Posted: Feb. 25, 2011, Last Update: Aug. 29, 2018, https://clinicaltrials.gov/ct2/show/study/NCT01303705. Date Accessed, Mar. 18, 2019 (10 pages).
Providence Health & Services, "Stereotactic Body Radiation and Monoclonal Antibody to OX40 (MEDI6469) in Breast Cancer Patients With Metastatic Lesions (OX40 Breast)," ClinicalTrials.gov Identifier: NCT01862900. First Posted May 27, 2013; Accessed Mar. 18, 2019: https://clinicaltrials.gov/ct2/show/study/NCT01862900.
PsiOxus Therapeutics Ltd, "Phase I / Dose Expansion Study of Enadenotucirev in Ovarian Cancer Patients (OCTAVE)," ClinicalTrials.gov: NCT02028117, First Posted: Jan. 6, 2014, Last Update: Feb. 26, 2019, https://clinicaltrials.gov/ct2/show/study/NCT02028117. Date Accessed, Mar. 25, 2019 (8 pages).
PsiOxus Therapeutics Ltd, "Phase I Study of Enadenotucirev and PD-1 Inhibitor in Subjects With Metastatic or Advanced Epithelial Tumors (SPICE)," ClinicalTrials.gov: PsiOxus Therapeutics Ltd,

(56) References Cited

OTHER PUBLICATIONS

First Posted: Dec. 21, 2015, Last Update: Mar. 4, 2019, https://clinicaltrials.gov/ct2/show/study/NCT02636036. Date Accessed, Mar. 25, 2019 (9 pages).
PubChem Open Chemistry Database, Compound Summary for CID 10890081, created Oct. 25, 2006 (14 pages).
PubChem Open Chemistry Database, Compound Summary for CID 12087079, created Feb. 7, 2007 (14 pages).
PubChem Open Chemistry Database, Compound Summary for CID 19046926, created Dec. 4, 2017 (11 pages).
PubChem Open Chemistry Database, Compound Summary for CID 70962830, created Mar. 21, 2013 (12 pages).
PubChem Open Chemistry Database, Compound Summary for SID 219642471, created Oct. 21, 2014 (3 pages).
Raman and Vaena, "Immunotherapy in Metastatic Renal Cell Carcinoma: A Comprehensive Review," Biomed Res Int. 2015;2015:367354.
Rana et al., "Role of CCR5 in infection of primary macrophages and lymphocytes by macrophage-tropic strains of human immunodeficiency virus: resistance to patient-derived and prototype isolates resulting from the delta ccr5 mutation," J Virol. Apr. 1997;71(4):3219-27.
Ratajczak et al., "The pleiotropic effects of the SDF-1-CXCR4 axis in organogenesis, regeneration and tumorigenesis," Leukemia. Nov. 2006;20(11):1915-24.
Reagen-Shaw et al., "Dose translation from animal to human studies revisited," FASEB J. Mar. 2008;22(3):659-61.
Reetz and Dreisbach, "Highly Efficient Lipase-Catalyzed Kinetic Resolution of Chiral Amines," Chimia. 1994;48(12):570.
Regeneron Pharmaceuticals, "An Exploratory Tumor Biopsy-driven Study to Understand the Relationship Between Biomarkers and Clinical Response in Melanoma Patients Receiving REGN2810 (Anti-PD-1)," ClinicalTrials.gov: NCT03002376, First Posted: Dec. 23, 2016, Last Update: Jan. 11, 2019, https://clinicaltrials.gov/ct2/show/study/NCT03002376. Date Accessed, Mar. 25, 2019 (6 pages).
Regeneron Pharmaceuticals, "PD-1 in Patients With Advanced Basal Cell Carcinoma Who Experienced Progression of Disease on Hedgehog Pathway Inhibitor Therapy, or Were Intolerant of Prior Hedgehog Pathway Inhibitor Therapy," ClinicalTrials.gov: NCT03132636, First Posted: Apr. 28, 2017, Last Update: Oct. 2, 2018, https://clinicaltrials.gov/ct2/show/study/NCT03132636. Date Accessed, Mar. 25, 2019 (6 pages).
Regeneron Pharmaceuticals, "Study of REGN 2810 Compared to Platinum-Based Chemotherapies in Participants With Metastatic Non-Small Cell Lung Cancer (NSCLC)," ClinicalTrials.gov: NCT03088540, First Posted: Mar. 23, 2017, Last Update: Nov. 5, 2018, https://clinicaltrials.gov/ct2/show/study/NCT03088540. Date Accessed, Mar. 25, 2019 (9 pages).
Regeneron Pharmaceuticals, "Study of REGN2810 and REGN1979 in Patients With Lymphoma," ClinicalTrials.gov: NCT02651662, First Posted: Jan. 11, 2016, Last Update: Sep. 11, 2018, https://clinicaltrials.gov/ct2/show/study/NCT02651662. Date Accessed, Mar. 25, 2019 (7 pages).
Regeneron Pharmaceuticals, "Study of REGN2810 in Patients With Advanced Cutaneous Squamous Cell Carcinoma," ClinicalTrials.gov: NCT02760498, First Posted: May 3, 2016, Last Update: Jan. 14, 2019, https://clinicaltrials.gov/ct2/show/study/NCT02760498. Date Accessed, Mar. 25, 2019 (6 pages).
Regeneron Pharmaceuticals, "Study of REGN3767 (Anti-LAG-3) With or Without REGN2810 (Anti-PD1) in Advanced Cancers," ClinicalTrials.gov: NCT03005782, First Posted: Dec. 29, 2016, Last Update: Jun. 18, 2018, https://clinicaltrials.gov/ct2/show/study/NCT03005782. Date Accessed, Mar. 25, 2019 (7 pages).
Righi et al., "CXCL12/CXCR4 blockade induces multimodal antitumor effects that prolong survival in an immunocompetent mouse model of ovarian cancer," Cancer Res. Aug. 15, 2011;71(16):5522-5534.
Rini et al., "Comparative effectiveness of axitinib versus sorafenib in advanced renal cell carcinoma (AXIS): a randomised phase 3 trial," Lancet. Dec. 3, 2011;378(9807):1931-9.

Rini et al., "Resistance to targeted therapy in renal-cell carcinoma", The Lancet, Oct. 2009, vol. 10, pp. 992-1000.
Robert et al., "Pembrolizumab versus Ipilimumab in Advanced Melanoma," N Engl J Med. Jun. 25, 2015;372(26):2521-32.
Robert Lowsky, "A Phase I/II Study of Intratumoral Injection of SD-101," ClinicalTrials.gov: NCT02254772, First Posted: Oct. 2, 2014, Last Update: Sep. 29, 2017, https://clinicaltrials.gov/ct2/show/study/NCT02254772. Date Accessed, Mar. 25, 2019 (9 pages).
Roe et al. "Inflammatory bowel disease in glycogen storage disease type Ib", J Pediatr. Jul. 1986;109(1):55-9.
Salcedo et al., "Vascular endothelial growth factor and basic fibroblast growth factor induce expression of CXCR4 on human endothelial cells: In vivo neovascularization induced by stromal-derived factor-1 alpha," Am J Pathol. Apr. 1999;154(4):1125-35.
Sato et al., "Intraepithelial CD8+ tumor-infiltrating lymphocytes and a high CD8+/regulatory T cell ratio are associated with favorable prognosis in ovarian cancer", PNAS, Dec. 20, 2005, vol. 102, No. 51, pp. 18538-18543.
Saxena et al., "Efficacy and Mechanism of Action of CXCR4 Inhibition in B16 OVA Melanoma Model," The Society for Immunotherapy of Cancer Annual Meeting, National Harbor, Maryland, Nov. 8-12, 2017 (1 page).
Saxena et al., "Efficacy and Mechanism of Action of CXCR4 Inhibition in B16-OVA Melanoma Model," Journal for Immuno Therapy of Cancer, Abstract, vol. 5, Suppl. 2, 2017 (p. 356).
Scala et al., "Expression of CXCR4 predicts poor prognosis in patients with malignant melanoma," Clin Cancer Res. Mar. 1, 2005;11(5):1835-41.
Scala, "Molecular Pathways: Targeting the CXCR4-CXCL12 Axis—Untapped Potential in the Tumor Microenvironment," Clin Cancer Res. Oct. 1, 2015;21(19):4278-85.
Schlabach et al., "Cancer proliferation gene discovery through functional genomics," Science. Feb. 1, 2008;319(5863):620-4.
Schols et al., "Bicyclams, a class of potent anti-HIV agents, are targeted at the HIV coreceptor fusin/CXCR-4," Antiviral Res. Aug. 1997;35(3):147-56.
Schols et al., "Inhibition of T-tropic HIV strains by selective antagonization of the chemokine receptor CXCR4," J Exp Med. Oct. 20, 1997;186(8):1383-8.
Schramm et al., "Cytopathicity of Human Immunodeficiency Virus Type 2 (HIV-2) in Human Lymphoid Tissue Is Coreceptor Dependent and Comparable to That of HIV-1," Journal of Virology, 2000, 74(20);9594-9600.
Schuitemaker et al., "Biological phenotype of human immunodeficiency virus type 1 clones at different stages of infection: progression of disease is associated with a shift from monocytotropic to T-cell-tropic virus population," J Virol. Mar. 1992;66(3):1354-60.
Semerad et al. "G-CSF is an essential regulator of neutrophil trafficking from the bone marrow to the blood." Immunity. 2002, 17:413-23.
Sharma et al., "CD8 tumor-infiltrating lymphocytes are predictive of survival in muscle-invasive urothelial carcinoma," Proc Natl Acad Sci U S A. Mar. 6, 2007;104(10):3967-72.
Sharma et al., "Primary, Adaptive, and Acquired Resistance to Cancer Immunotherapy," Cell. Feb. 9, 2017;168(4):707-723.
Shen et al., "CXCR4-mediated Stat3 activation is essential for CXCL12-induced cell invasion in bladder cancer," Tumour Biol. Jun. 2013;34(3):1839-45.
Shojaei et al., "Tumor refractoriness to anti-VEGF treatment is mediated by CD11b+Gr1+ myeloid cells," Nat Biotechnol. Aug. 2007;25(8):911-20.
Shyamala et al., "Risk of tumor cell seeding through biopsy and aspiration cytology," J Int Soc Prev Community Dent. Jan.-Apr. 2014;4(1):5-11.
Sicre de Fontbrune et al. "Severe chronic primary neutropenia in adults: report on a series of 108 patients", Blood, Oct. 1, 2015, 126:1643-1650.
Sidney Kimmel Comprehensive Cancer Center at Johns Hopkins, "Anti-LAG-3 Alone & in Combination w/ Nivolumab Treating Patients w/ Recurrent GBM (Anti-CD137 Arm Closed Oct. 16, 2018)," ClinicalTrials.gov: NCT02658981, First Posted: Jan. 20, 2016, Last Update: Feb. 11, 2019, https://clinicaltrials.gov/ct2/show/study/NCT02658981. Date Accessed, Mar. 18, 2019 (13 pages).

(56) References Cited

OTHER PUBLICATIONS

Sidney Kimmel Comprehensive Cancer Center at Johns Hopkins, "Pilot Study With CY, Pembrolizumab, GVAX, and IMC-CS4 (LY3022855) in Patients With Borderline Resectable Adenocarcinoma of the Pancreas," ClinicalTrials.gov: NCT03153410, First Posted: May 15, 2017, Last Update: Mar. 19, 2019, https://clinicaltrials.gov/ct2/show/study/NCT03153410. Date Accessed, Mar. 18, 2019 (8 pages).

Sillajen, Inc., "Hepatocellular Carcinoma Study Comparing Vaccinia Virus Based Immunotherapy Plus Sorafenib vs Sorafenib Alone (PHOCUS)," ClinicalTrials.gov Identifier: NCT02562755. First Posted Sep. 29, 2015; Accessed Mar. 25, 2019: https://clinicaltrials.gov/ct2/show/study/NCT02562755.

Silva et al., "Profiling essential genes in human mammary cells by multiplex RNAi screening," Science. Feb. 1, 2008;319(5863):617-20.

Simmons et al., "CXCR4 as a functional coreceptor for human immunodeficiency virus type 1 infection of primary macrophages," J Virol. Oct. 1998;72(10):8453-7.

Simmons et al., "Primary, syncytium-inducing human immunodeficiency virus type 1 isolates are dual-tropic and most can use either Lestr or CCR5 as coreceptors for virus entry," J Virol. Dec. 1996;70(12):8355-60.

SK Chemicals Co., Ltd., "Study to Evaluate SID 530 Compared to Taxotere," ClinicalTrials.gov: NCT00931008, First Posted: Jul. 2, 2009, Last Update: Jan. 24, 2013, https://clinicaltrials.gov/ct2/show/study/NCT00931008. Date Accessed, Mar. 25, 2019 (6 pages).

Skerlj et al., "Discovery of novel small molecule orally bioavailable C-X-C chemokine receptor 4 antagonists that are potent inhibitors of T-tropic (X4) HIV-1 replication," J Med Chem. Apr. 22, 2010;53(8):3376-88.

Spranger et al., "Up-regulation of PD-L1, IDO, and T(regs) in the melanoma tumor microenvironment is driven by CD8(+) T cells," Sci Transl Med. Aug. 28, 2013;5(200):200ra116.

Stone et al., "Multiple-dose escalation study of the safety, pharmacokinetics, and biologic activity of oral AMD070, a selective CXCR4 receptor inhibitor, in human subjects," Antimicrob Agents Chemother. Jul. 2007;51(7):2351-8.

Sullivan and Flaherty, "Pembrolizumab for Treatment of Patients with Advanced or Unresectable Melanoma," Clin Cancer Res. Jul. 1, 2015;21(13):2892-7.

Supplementary European Search Report from EP 02775823.4, dated Dec. 14, 2004.

Supplementary European Search Report from EP 02805977.2, dated Apr. 16, 2008.

Supplementary European Search Report from EP 04752905.2, dated Mar. 12, 2010.

Supplementary European Search Report from EP04760161.2, dated Jun. 10, 2008.

Supplementary European Search Report from EP04814091.7, dated Mar. 10, 2008.

Suratt et al., "Role of the CXCR4/SDF-1 chemokine axis in circulating neutrophil homeostasis." Blood. Jul. 15, 2004;104(2):565-71.

Syndax Pharmaceuticals, "A Phase 2 Multi-Center Study of Entinostat (SNDX-275) in Patient With Relapsed or Refractory Hodgkin's Lymphoma," ClinicalTrials.gov: NCT00866333, First Posted: Mar. 20, 2009, Last Update: Jul. 1, 2016, https://clinicaltrials.gov/ct2/show/study/NCT00866333. Date Accessed, Mar. 20, 2019 (6 pages).

Tamamura et al., "Identification of a CXCR4 antagonist, a T140 analog, as an anti-rheumatoid arthritis agent," FEBS Lett. Jul. 2, 2004;569(1-3):99-104.

Targovax Oy, "A Pilot Study of Sequential ONCOS-102, an Engineered Oncolytic Adenovirus Expressing GMCSF, and Pembrolizumab in Patients With Advanced or Unresectable Melanoma Progressing After Programmed Cell Death Protein 1 (PD1) Blockade," ClinicalTrials.gov: NCT03003676, First Posted: Dec. 28, 2016, Last Update: Oct. 25, 2018, https://clinicaltrials.gov/ct2/show/study/NCT03003676. Date Accessed, Mar. 25, 2019 (8 pages).

Tarhini et al., "Immune monitoring of the circulation and the tumor microenvironment in patients with regionally advanced melanoma receiving neoadjuvant ipilimumab," PLoS One. Feb. 3, 2014;9(2):e87705.

Teasdale et al., "Risk Assessment of Genotoxic Impurities in New Chemical Entities: Strategies to Demonstrate Control," Org Process Res Dev. Jan. 14, 2013;17:221-30.

Tersmette et al., "Differential syncytium-inducing capacity of human immunodeficiency virus isolates: frequent detection of syncytium-inducing isolates in patients with acquired immunodeficiency syndrome (AIDS) and AIDS-related complex," J Virol. Jun. 1988;62(6):2026-32.

Tesaro, Inc., "A Phase 1 Study of TSR-022, an Anti-TIM-3 Monoclonal Antibody, in Patients With Advanced Solid Tumors (AMBER)," ClinicalTrials.gov: NCT02817633, First Posted: Jun. 29, 2016, Last Update: Mar. 19, 2019, https://clinicaltrials.gov/ct2/show/study/NCT02817633. Date Accessed, Mar. 25, 2019 (8 pages).

Therasse et al., "New guidelines to evaluate the response to treatment in solid tumors. European Organization for Research and Treatment of Cancer, National Cancer Institute of the United States, National Cancer Institute of Canada," J Natl Cancer Inst. Feb. 2, 2000;92(3):205-16.

Ting-Chou et al., "Quantitative analysis of dose-effect relationships: the combined effects of multiple drugs or enzyme inhibitors", Adv Enzyme Regul, 1984, vol. 22, pp. 27-55.

Tortorici et al., "Influence of mild and moderate hepatic impairment on axitinib pharmacokinetics," Invest New Drugs. Dec. 2011;29(6):1370-80.

Toyozawa et al., "Chemokine receptor CXCR4 is a novel marker for the progression of cutaneous malignant melanomas," Acta Histochem Cytochem. Oct. 31, 2012;45(5):293-9.

Trillium Therapeutics Inc., "A Trial of TTI-621 for Patients With Hematologic Malignancies and Selected Solid Tumors," ClinicalTrials.gov: NCT02663518, First Posted: Jan. 26, 2016, Last Update: Oct. 29, 2018, https://clinicaltrials.gov/ct2/show/study/NCT02663518. Date Accessed, Mar. 18, 2019 (9 pages).

Trillium Therapeutics Inc., "Trial of Intratumoral Injections of TTI-621 in Subjects With Relapsed and Refractory Solid Tumors and Mycosis Fungoides," ClinicalTrials.gov: NCT02890368, First Posted: Sep. 7, 2016, Last Update: Mar. 13, 2019, https://clinicaltrials.gov/ct2/show/study/NCT02890368. Date Accessed, Mar. 18, 2019 (9 pages).

Tu et al., "Curcumin induces the differentiation of myeloid-derived suppressor cells and inhibits their interaction with cancer cells and related tumor growth," Cancer Prev Res (Phila). Feb. 2012;5(2):205-15.

Tumeh et al., "PD-1 blockade induces responses by inhibiting adaptive immune resistance," Nature. Nov. 27, 2014;515(7528):568-71.

Tunstall, "Quantifying Immune Cell Distribution in the Tumor Microenviroment Using HALO Spatial Analysis Tools", Application Note, Jul. 2016, Indica Labs, accessed Nov. 1, 2017, https://thepathologist.com/fileadmin/issues/App_Notes/0016-010-halo-app-note.pdf.

Ueno et al., "Impaired monocyte function in glycogen storage disease type 1d." Eur J Pediatr. 1986, 145:312-14.

University of Southern California, "Axitinib With or Without Anti-OX40 Antibody PF-04518600 in Treating Patients With Metastatic Kidney Cancer," ClinicalTrials.gov: NCT03092856, First Posted: Mar. 28, 2017, Last Update: Aug. 13, 2018, https://clinicaltrials.gov/ct2/show/study/NCT03092856. Date Accessed, Mar. 18, 2019 (11 pages).

University of Texas Southwestern Medical Center, "Phase 2 Study of IDH305 in Low Grade Gliomas," ClinicalTrials.gov: NCT02987010, First Posted: Dec. 8, 2016, Last Update: Oct. 11, 2017, https://clinicaltrials.gov/ct2/show/study/NCT02987010. Date Accessed, Mar. 25, 2019 (7 pages).

Vaishampayan et al., "A phase 1/2 study evaluating the efficacy and safety of the oral CXCR4 inhibitor X4P-001 in combination with axitinib in patients with advanced renal cell carcinoma," J Clin Oncol. 2018;36(15 suppl):4510(abstract).

(56) References Cited

OTHER PUBLICATIONS

Vanharanta et al., "Epigenetic expansion of VHL-HIF signal output drives multiorgan metastasis in renal cancer," Nat Med. Jan. 2013;19(1):50-6.
Veiga-da-Cunha et al., "Failure to eliminate a phosphorylated glucose analog leads to neutropenia in patients with G6PT and G6PC#3 deficiencies." Proc Natl Acad Sci USA. Jan. 9, 2019. 116(4):1241-50.
VentiRx Pharmaceuticals Inc., "A Phase Ib Study of Neoadjuvant of Cetuximab Plus Motolimod and Cetuximab Plus Motolimod Plus Nivolumab," ClinicalTrials.gov: NCT02124850, First Posted: Apr. 28, 2014, Last Update: Jul. 22, 2016, https://clinicaltrials.gov/ct2/show/study/NCT02124850. Date Accessed, Mar. 25, 2019 (6 pages).
Vinh et al., "Autosomal dominant and sporadic monocytopenia with susceptibility to mycobacteria, fungi, papillomaviruses, and myelodysplasia." Blood. 2010, 115:1519-29.
Visser et al., "Granulocyte colony-stimulating factor in glycogen storage disease type 1b. Results of the European study on glycogen storage disease type 1." Eur J Pediatr. 2002, 161(Suppl 1):S83-7.
Visser et al., "Neutropenia, neutrophil dysfunction, and inflammatory bowel disease in glycogen storage disease type Ib: results of the European Study on Glycogen Storage Disease type I." J Pediatr. Aug. 2000, 137(2):187-91.
Waggott et al., "NanoStringNorm: an extensible R package for the pre-processing of NanoString mRNA and miRNA data", Bioinformatics, 2012, vol. 28, pp. 1546-1548.
Wang et al., "In vitro characterization of the anti-PD-1 antibody nivolumab, BMS-936558, and in vivo toxicology in non-human primates," Cancer Immunol Res. Sep. 2014;2(9):846-56.
Ward and Dale, "Genetic and molecular diagnosis of severe congenital neutropenia," Curr Opin Hematol. Jan. 2009; 16(1):9-13.
Wong et al., "Comparison of the potential multiple binding modes of bicyclam, monocylam, and noncyclam small-molecule CXC chemokine receptor 4 inhibitors," Mol Pharmacol. Dec. 2008;74(6):1485-95.
World Medical Association, "WMA Declaration of Helsinki—Ethical Principles for Medical Research Involving Human Subjects," Policy. Amended Oct. 2013; http://www.wma.net/en/30publications/10policies/b3/.
X4 Pharmaceuticals, "Addition of X4P-001 to Nivolumab Treatment in Patients With Renal Cell Carcinoma", ClinicalTrails.gov Identifier: NCT02923531. First submitted Feb. 8, 2017, Lastest version submitted Jul. 24, 2019, https://clinicaltrials.gov/ct2/history/NCT02923531?V_4=View#StudyPageTop.
X4 Pharmaceuticals, "NCT02823405: X4P-001 and Prembrolizumab in Patents With Advanced Melanoma (X4P-001-MELA)," Jul. 6, 2016, https://clinicaltrials.gov/ct2/show/NCT02823405>Date Accessed Oct. 5, 2018 (7 pages).
X4 Pharmaceuticals, "X4 Pharmaceuticals announces new data for lead candidate X4P-001 in renal cell carcinoma at EORTC-NCI-AACR Molecular Targets and Cancer Therapeutic Symposium", Nov. 30, 206, Cambridge Mass, https://www.x4pharma.com/news/x4-pharmaceuticals-announces-new-data-lead-candidate-x4p-001-renal-cell-carcinoma-eortc-nci-aacr-molecular-targets-cancer-therapeutics-symposium/.
X4 Pharmaceuticals, "X4 Pharmaceuticals Initiates Phase 1b Clinical Trial of Mavorixafor for the Treatment of Severe Congenital Neutropenia," Bloomgerb Business Press Release. Nov. 5, 2019; https://www.bloomberg.com/press-releases/2019-11-05/x4-pharmaceuticals-initiates-phase-1b-clinical-trial-of-mavorixafor-for-the-treatment-of-severe-congenital-neutropenia.
X4 Pharmceuticals, "Trial of X4P-001 in Patients With Advanced Renal Cell Carcinoma," ClinicalTrials.gov Identifier: NCT02667886. First Posted Jan. 29, 2016; Accessed Mar. 17, 2021: https://clinicaltrials.gov/ct2/show/NCT02667886.
Xiaoli Wei, Cancer immunotherapy : research advances, "Journal of International Pharmaceutical Research," 2014, vol. 41, No. 1, pp. 57-62.

Yamazaki et al., "Cytokine biomarkers to predict antitumor responses to nivolumab suggested in a phase 2 study for advanced melanoma," Cancer Sci. May 2017;108(5):1022-1031.
Yu et al."CXCL12/CXCR4 promotes inflammation-driven colorectal cancer progression through activation of RhoA signaling by sponging miR-133a-3p", J Exp Clin Cancer Res., Jan. 24, 2019, 38(1):32, doi: 10.1186/s13046-018-1014-x.
ZagZag et al., "Stromal cell-derived factor-1alpha and CXCR4 expression in hemangioblastoma and clear cell-renal cell carcinoma: von Hippel-Lindau loss-of-function induces expression of a ligand and its receptor," Cancer Res. Jul. 1, 20055;65(14):6178-88.
Zea et al., "Arginase-producing myeloid suppressor cells in renal cell carcinoma patients: a mechanism of tumor evasion," Cancer Res. Apr. 15, 2005;65(8):3044-8.
Zhang and Moore, "Will multiple coreceptors need to be targeted by inhibitors of human immunodeficiency virus type 1 entry?," J Virol. Apr. 1999;73(4):3443-8.
Zhang et al., "Chemokine coreceptor usage by diverse primary isolates of human immunodeficiency virus type 1," J Virol. Nov. 1998;72(11):9307-12.
Zhang et al., "Preferential involvement of CX chemokine receptor 4 and CX chemokine ligand 12 in T-cell migration toward melanoma cells," Cancer Biol Ther. Oct. 2006;5(10):1304-12.
Zhang et al., "Targeting primary acute myeloid leukemia with a new CXCR4 antagonist IgG1 antibody (PF-06747143)," Sci Rep. Aug. 4, 2017;7:7305.
Zhao et al., "TNF signaling drives myeloid-derived suppressor cell accumulation," J Clin Invest. Nov. 2012;122(11):4094-104.
Zlotnik and Yoshie, "Chemokines: a new classification system and their role in immunity," Immunity. Feb. 2000;12(2):121-7.
Zou et al., "PD-L1 (B7-H1) and PD-1 pathway blockade for cancer therapy: Mechanisms, response biomarkers, and combinations," Sci Transl Med. Mar. 2, 2016;8(328):328rv4.
Zuelzer, "'Myelokathexis'—A New Form of Chronic Granulocytopenia. Report of a case," N Engl J Med. Apr. 2, 1964;270:699-704.
Parker, "Glucose-6-phosphate translocase as a target for the design of antidiabetic agents", Drugs Fut. 2001. 26(7):687-693.
PCT International Search Report and Written Opinion from PCT/US2020/066099 dated Mar. 23, 2021.
PCT International Search Report and Written Opinion from PCT/US2021/021713 dated May 18, 2021.
PCT International Search Report and Written Opinion from PCT/US2023/016451 dated Aug. 4, 2023.
PCT International Search Report and Written Opinion from PCT/US2023/68229 dated Oct. 19, 2023.
Furze and Rankin, "Neutrophil mobilization and clearance in the bone marrow", Immunology. Nov. 2008;125(3):281-8.
Dancey et al., "Neutrophil kinetics in man", J Clin Invest. Sep. 1976;58(3):705-15.
Connelly and Walkovich, "Diagnosis and therapeutic decision-making for the neutropenic patient", Hematol Am Soc Hematol Educ Program. Dec. 10, 2021;2021(1):492-503.
Skokowa et al., "Severe congenital neutropenias", Nat Rev Dis Primers. Jun. 8, 2018:3:17032.
Horwitz et al., "ELANE mutations in cyclic and severe congenital neutropenia: genetics and pathophysiology", Hematol Oncol Clin North Am. Feb. 2013;27(1):19-41.
Tran et al., "CRISPR-Cas9-Mediated ELANE Mutation Correction in Hematopoietic Stem and Progenitor Cells to Treat Severe Congenital Neutropenia", Mol Ther. Dec. 2, 2020;28(12):2621-2634.
PCT International Search Report and Written Opinion from PCT/US2023/68230 dated Oct. 27, 2023.
X4 Pharmaceuticals, "X4 Pharmaceuticals Announces Positive Interim Clinical Data from Ongoing Six-Month Phase 2 Trial of Mavorixafor in Chronic Neutropenia (CN) and Initiation of Pivotal Phase 3 CN Trial." Available online Jun. 27, 2024; downloaded Sep. 2, 2024. <https://investors.x4pharma.com/news-releases/news-release-details/x4-pharmaceuticals-announces-positive-interim-clinical-data>.
X4 Pharmaceuticals, "Mavorixafor in Chronic Neutropenia: Interim data from ongoing Phase 2 clinical trial." Available online Jun. 27, 2024; downloaded Sep. 2, 2024. <https://investors.x4pharma.com/static-files/81905390-b822-4b68-bfe0-64001619cd41>.

(56) References Cited

OTHER PUBLICATIONS

Anonymous: "History of Changes for Study: NCT04154488: A Study of Mavorixafor in Participants With Severe Congenital Neutropenia and Chronic Neutropenia Disorders", ClinicalTrials. gov archive, Nov. 4, 2019, pp. 1-8, <https://classic.clinicaltrials.gov/ct2/history/NCT04154488?_View#StudyPageTop>, retrieved Feb. 19, 2024.

Dale et al., "Phase 2 Study of X4P-001: A Targeted Oral Therapy for Patients with WHIM Syndrome", 23rd Congress of the European Hematology Association (EHA), Jun. 14, 2018, <https://www.x4pharma.com/wp-content/uploads/2022/11/EHA18_WHIM_POSTER_Final.pdf>.

Dale et al., "Determiniation of Phase 3 Dose for X4P-001 in Patients with WHIM Syndrome", Blood, vol. 132, No. Supplement 1, Nov. 29, 2018, pp. 1102.

\* cited by examiner

METHODS FOR TREATING NEUTROPENIA

CROSS-REFERENCE TO RELATED APPLICATIONS

This application is a continuation of International Application No. PCT/US2021/021713, filed Mar. 10, 2021, which claims the benefit under 35 U.S.C. 119(e) of U.S. Provisional Application No. 62/987,707, filed Mar. 10, 2020, the contents of each of which is hereby incorporated by reference in its entirety.

FIELD OF THE INVENTION

The present invention relates to methods for treating neutropenia, such as severe chronic idiopathic neutropenia, including certain genetically defined congenital forms of neutropenia, using a compound that inhibits CXC Receptor type 4 (CXCR4), optionally in combination with a standard of care treatment such as G-CSF.

BACKGROUND OF THE INVENTION

Neutropenia is a condition characterized by an abnormally low concentration of neutrophils circulating in the blood, and defined by an absolute neutrophil count (ANC) below 1500 cells/μL. Severe neutropenia (ANC<500 cells/μL) is a risk factor for susceptibility to bacterial infection. Neutrophils make up the majority of circulating white blood cells and play an important role in the body's defenses against bacterial or fungal pathogenic infections and in shaping the host response to infection. In addition, neutrophils participate in immune system homeostasis. Neutropenia can be divided into congenital (i.e., present at birth) and acquired. Additionally, neutropenia can be "acute" (transient, or temporary, often as a response to specific events that deplete the body of neutrophils, such as radiation or chemotherapy), or "chronic" (a long-term or long-lasting effect that may be due to the presence of genetic abnormalities).

Acute or transient neutropenia can be caused by infectious agents, such as the typhoid-causing bacterium *Salmonella enterica*; and cytomegalovirus, as well as chemical agents, including propylthiouracil; levamisole; penicillamine; clozapine; valproic acid; and cancer chemotherapy.

Chronic neutropenia can be caused by genetic abnormalities (congenital neutropenia). Mutations in ELANE are the most common cause of congenital neutropenia. Other examples of genes that can be responsible for genetic causes of neutropenia include HAX1, G6PC3, WAS, SBDS, and others. In addition, some enzyme deficiencies can be associated with neutropenia such as glycogen storage disease 1b. Other causes of neutropenia include mitochondrial diseases, such as Pearson syndrome. Some autoimmune diseases, such as systemic lupus erythematosus ("SLE" or "lupus") may be associated with neutropenia. Aplastic anemia, due to bone marrow failure, is associated with thrombocytopenia, anemia and neutropenia; Evans syndrome is characterized by autoimmune hemolytic anemia (AIHA) and immune thrombocytopenia (ITP) and/or immune neutropenia; and Felty's syndrome is characterized by rheumatoid arthritis, splenomegaly and neutropenia. Chronic neutropenia may also be the result of nutritional deficiencies, such as abnormally low levels of copper or Vitamin B12; or chronic infections, such as with human immunodeficiency virus (HIV), the agent that causes AID syndrome.

Neutropenia may be asymptomatic and often is only diagnosed fortuitously. Today, the standard treatment for severe neutropenia is administration of granulocyte colony-stimulating factor (G-CSF). Historically, neutropenia has been treated in a host of manners, including splenectomy, corticosteroids, androgens, and immunosuppressive and immune-modulating therapies. Currently, however, these treatments are generally not recommended except in cases where treatment with G-CSF is not effective. Dale et al. (2017) Curr. Opin. Hematol. 24:46-53; Sicre de Fontbrune et al. (2015) Blood 126:1643-1650. Other treatments for neutropenia can include bone marrow transportation and/or treatment with cord blood stem cells.

Thus, there remains a need for more effective treatments of neutropenia and associated diseases. The present invention addresses this need and provides other related advantages.

SUMMARY OF THE INVENTION

In one aspect, the present invention provides a method of treating neutropenia, comprising administering to a patient in need thereof an effective amount of mavorixafor or a pharmaceutically acceptable salt or composition thereof, optionally in combination with a standard of care treatment. In some embodiments, the standard of care treatment is G-CSF or GM-CSF.

In another aspect, the present invention provides a method for treating a patient with neutropenia at risk of infections, comprising administering to the patient an effective amount of mavorixafor or a pharmaceutically acceptable salt or composition thereof.

In another aspect, the present invention provides a method for reducing the dosage of G-CSF for treating severe chronic neutropenia (SCN) in a patient in need thereof, comprising administering to the patient an effective amount of mavorixafor or a pharmaceutically acceptable salt or composition thereof.

In some embodiments, the patient has an absolute neutrophil count (ANC) less than about 500 cells/μL.

In some embodiments, patients with neutropenia, such as patients with SCN or CIN, or a related disease, are treated with an effective amount of mavorixafor, or a pharmaceutically acceptable salt or composition thereof, either as a single agent (monotherapy), or in combination with other treatments for neutropenia (combination therapy). In some embodiments, the combination therapy comprises treatment with an effective amount of granulocyte colony-stimulating factor (G-CSF), granulocyte-macrophage colony-stimulating factor (GM-CSF), a variant of G-CSF or GM-CSF (e.g., a pegylated version), bone marrow transplantation, treatment with cord blood stem cells, or a combination thereof.

In some embodiments, the neutropenia is chronic idiopathic neutropenia (CIN), severe chronic neutropenia (SCN), or autoimmune neutropenia (AIN). In some embodiments, the patient has a genetic abnormality selected from GSD1b, G6PC3 deficiency, GATA2 deficiency, or a genetically-defined condition with or without myeloid maturation arrest at the myelocyte/promyelocyte stage.

In some embodiments, G-CSF is co-administered to the patient at a starting dosage of about 6 mcg/kg as a twice daily subcutaneous injection (for a patient having congenital neutropenia); or about 5 mcg/kg as a single daily subcutaneous injection (for a patient having idiopathic or cyclic neutropenia). In some embodiments, the patient is already receiving G-CSF and continues chronic dosing at a dosage sufficient to maintain clinical benefits, such as daily administration in the amount of about 6 mcg/kg (for patients having congenital neutropenia); about 2.1 mcg/kg (for patients having cyclic neutropenia); or about 1.2 mcg/kg (for patients having idiopathic neutropenia).

In another aspect, the present invention provides a method for treating neutropenia, comprising administering to a patient in need thereof an effective amount of mavorixafor, or a pharmaceutically acceptable salt or composition thereof, in combination with an effective amount of G-CSF or GM-CSF, or a variant thereof, wherein the effective amount of G-CSF or GM-CSF, or a variant thereof is less than the approved dosage as a monotherapy for a similar patient being treated with the G-CSF or GM-CSF, or a variant thereof.

In certain embodiments, the dosage of G-CSF that is administered to the patient is reduced by at least about 25% relative to the patient's previous dose before beginning treatment with mavorixafor or a pharmaceutically acceptable salt or composition thereof. In certain embodiments, the dosage of G-CSF that is administered to the patient is reduced by at least about 50%, 75%, or 95% relative to the patient's previous dose before beginning treatment with mavorixafor or a pharmaceutically acceptable salt or composition thereof.

In certain embodiments, the dosage of G-CSF or GM-CSF, or variant thereof, that is administered to the patient is reduced by at least about 10%, 15%, 20%, 25%, 30%, 35%, 40%, 50%, 55%, 60%, 65%, 70%, 75%, 80%, 85%, 90%, or 95%. In certain embodiments, the frequency of dosage of G-CSF or GM-CSF, or variant thereof is reduced, for example, reduced in frequency by at least 25%, 50%, 75%, or 90%.

In some embodiments, a disclosed method features a decrease in the incidence of bone pain in the patient, or across a representative group of patients. In some embodiments, a disclosed method features a decrease in the incidence of flu-like symptoms in the patient, or across a representative group of patients. In some embodiments, a disclosed method features a decrease in the incidence of a myeloid malignancy, such as such as myelodysplasia (MDS) or acute myeloid leukemia (AML), in the patient, or across a representative group of patients.

In some embodiments, the patient has previously been treated with G-CSF. In some embodiments, the patient has previously been treated with G-CSF or GM-CSF, or a variant thereof.

In some embodiments, the patient has not previously been treated with G-CSF prior to commencing treatment with mavorixafor, or a pharmaceutically acceptable salt or composition thereof. In some embodiments, the patient has not previously been treated with G-CSF or GM-CSF, or a variant thereof.

In some embodiments, treatment with G-CSF is completely discontinued (while maintaining effective treatment of the patient's neutropenia) after commencing treatment with mavorixafor, or a pharmaceutically acceptable salt thereof. In some embodiments, treatment with G-CSF or GM-CSF, or a variant thereof, is completely discontinued (while maintaining effective treatment of the patient's neutropenia) after commencing treatment with mavorixafor, or a pharmaceutically acceptable salt thereof.

In some embodiments, the patient has idiopathic neutropenia. In some embodiments, the patient has severe idiopathic neutropenia. In some embodiments, the patient has chronic neutropenia. In some embodiments, the patient has SCN, CIN, or AIN. In some embodiments, the patient has undergone genetic testing but no diagnosis of a genetic abnormality has been made. In some embodiments, the genetic testing was inconclusive. In some embodiments, the genetic testing revealed no known genetic abnormality, or a genetic abnormality not associated with neutropenia. In some embodiments, the patient has neutropenia not due to a genetic abnormality and due to one or more of an infectious, inflammatory, autoimmune, or malignant cause. In some embodiments, the malignant cause is a cancer.

In some embodiments, the patient has severe congenital neutropenia, suspected aplastic anemia, B-cell immunodeficiency, juvenile myelodysplastic syndrome (MDS), chronic myelomonocytic leukemia, a severe Epstein-Barr virus infection or Epstein-Barr-associated cancers, B-cell acute lymphoblastic leukemia, or unexplained bone marrow failure. In some embodiments, the patient is at an elevated risk of one or more of the foregoing.

In some embodiments, the patient does not have a genetic abnormality associated with WHIM syndrome (a gain-of-function mutation in the CXCR4 gene). In some embodiments, the patient has undergone genetic testing and a genetic abnormality other than one associated with WHIM syndrome has been diagnosed. WHIM-associated genetic abnormalities typically include a gain-of-function mutation in the CXCR4 gene. In some embodiments, the patient has a congenital neutropenia. In some embodiments, the patient has a genetic abnormality selected from GSD1b, G6PC3 deficiency, GATA2 deficiency, a genetically-defined condition with myeloid maturation arrest at the myelocyte/promyelocyte stage, a genetically-defined condition without myeloid maturation arrest at the myelocyte/promyelocyte stage, or an undefined genetic abnormality.

In some embodiments, a provided method further comprises the step of obtaining a biological sample from the patient and measuring the amount of a disease-related biomarker. In some embodiments, the biological sample is a blood sample. In certain embodiments, the disease-related biomarker is selected from the group consisting of CXCR4, SDF-1α/CXCL12; and GRK3 (G protein coupled receptor kinase 3).

In certain embodiments, after commencement of administration of mavorixafor, the dosage of G-CSF administered to the patient is reduced, while maintaining absolute neutrophil counts (ANC) equal to or higher than 500 cells/μL. In certain embodiments, the dosage of G-CSF or GM-CSF, or variant thereof, that is administered to the patient is reduced by about 10%, 15%, 20%, 25%, 30%, 35%, 40%, 50%, 55%, 60%, 65%, 70%, 75%, 80%, 85%, 90%, or 95%. In certain embodiments, administration of G-CSF or GM-CSF, or variant thereof, is eliminated, or administered only in the event of a crisis, for example, if ANC levels drop below 500 cells/μL.

In some embodiments, the daily dose of mavorixafor, or a pharmaceutically acceptable salt or composition thereof, is from about 100 mg to about 800 mg. In some embodiments, the daily dose is about 200 mg to about 600 mg, such as about 400 mg. In some embodiments, the daily dose is administered in divided doses twice per day. In some embodiments, the daily dose is administered once per day. In some embodiments, the mavorixafor, or a pharmaceutically acceptable salt or composition thereof, is administered in a fasted state.

BRIEF DESCRIPTION OF THE FIGURES

In FIG. 1, ALC=absolute lymphocyte count; ANC=absolute neutrophil count; AUCabs=non threshold-adjusted area under the plasma concentration curve; AUClast=area under the plasma concentration curve to the last measurable concentration. Units: cells·hr/μL. Panel A: ANC. Panel B: ALC. Symbols: bold solid line: median; cross: mean; box: 25th to 75th percentiles; whiskers: 1.5× interquartile range; dashed line: threshold; dotted line: baseline threshold, calculated by using the geometric mean baseline ANC across all subjects, multiplied by the 24 hr dosing interval.

DETAILED DESCRIPTION OF CERTAIN EMBODIMENTS OF THE INVENTION

Figure 1:
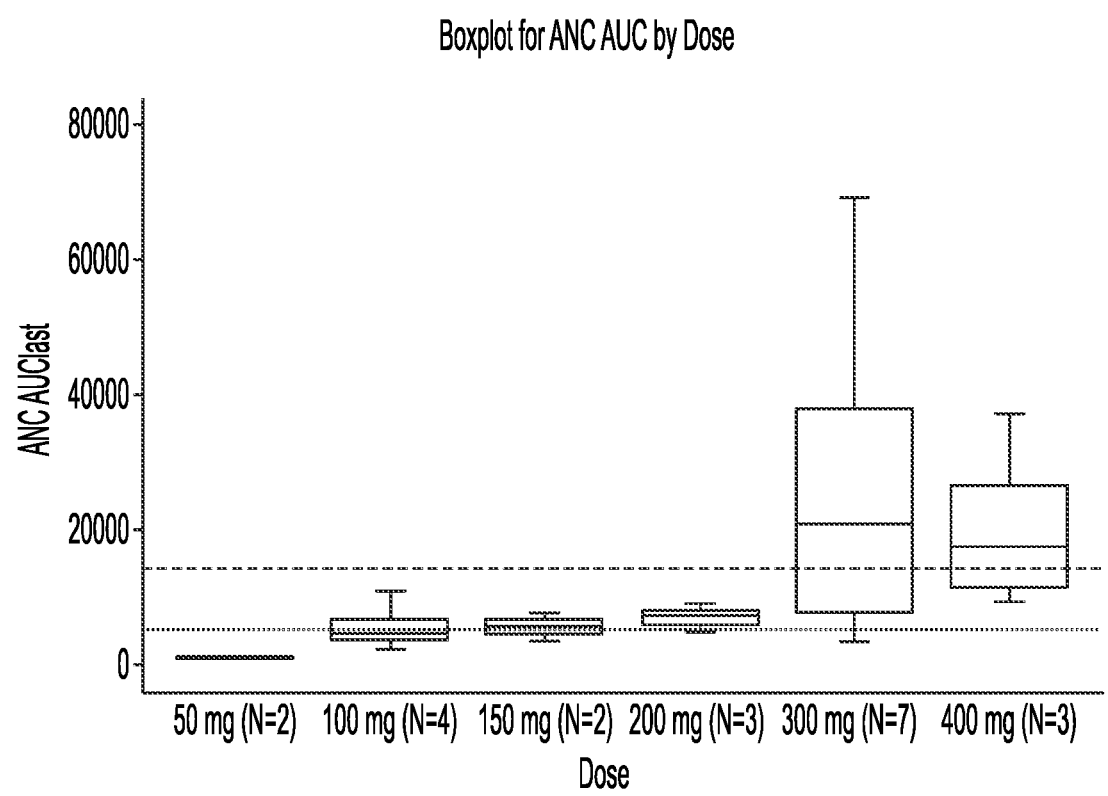
FIG. 1 illustrates a boxplot for the area under the curve (AUC) for absolute neutrophil count ($AUC_{ANC}$) in patients receiving mavorixafor.
Figure 2:
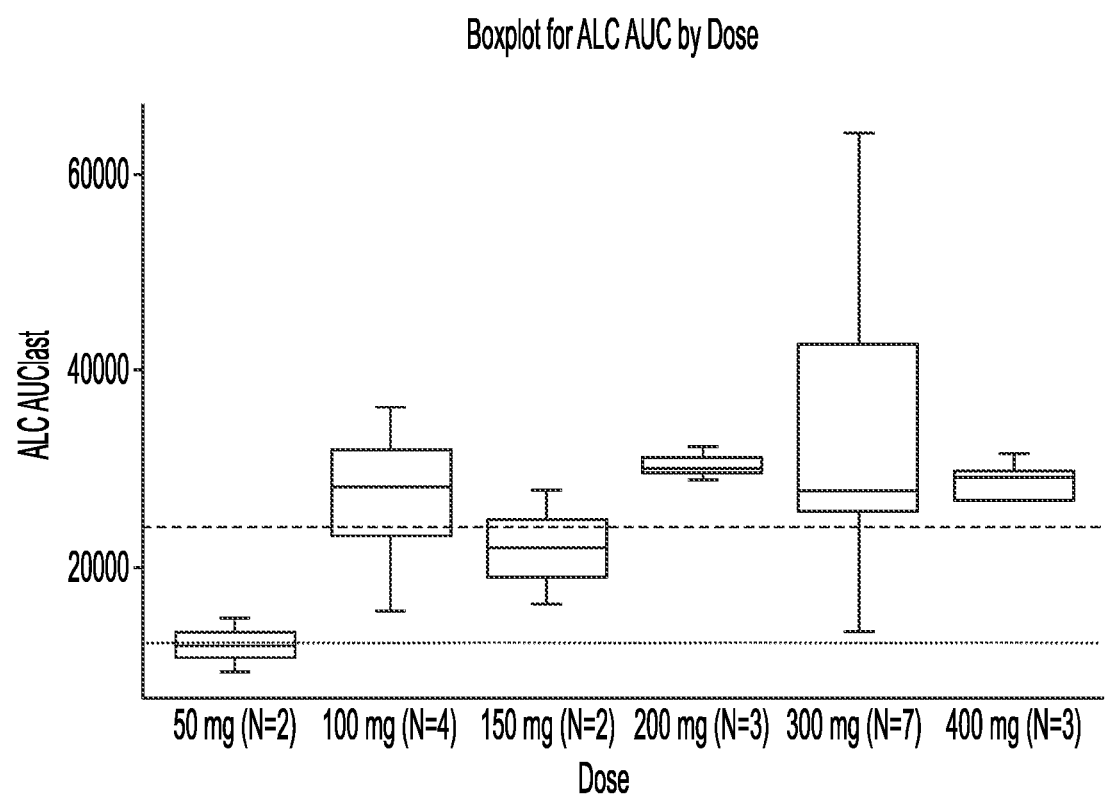
FIG. 2 illustrates a boxplot for the area under the curve (AUC) for absolute lymphocyte count ($AUC_{ALC}$) in patients receiving mavorixafor. The same abbreviations are used as in FIG. 1.

It has now been found that CXCR4 inhibitors such as mavorixafor (X4P-001) are useful for treating neutropenia, such as severe chronic idiopathic neutropenia, including certain genetically defined congenital forms of neutropenia, optionally in combination with a standard of care treatment such as G-CSF.

As used herein, the term "neutropenia" means that a patient has an absolute neutrophil count (ANC) that is at or below about 1000 cells per μL. As used herein, "severe neutropenia" means that the patient has an ANC that is at or below 500 cells/μL.

As used herein, the term "chronic neutropenia" is defined as neutropenia lasting for a period of at least three (3) months. The term "idiopathic" as applied herein to neutropenia means that the neutropenia is not attributable to drugs, or to a specific identified genetic, infectious, inflammatory, autoimmune or malignant cause.

As used herein, the "congenital neutropenia" condition includes patients who exhibit neutropenia (or severe neutropenia) due to a genetically defined mutation such as glycogen storage disease type 1b (GSD1b) due to mutations in SLC37A4, glucose-6-phosphatase catalytic subunit 3 (G6PC3) deficiency due to mutations in G6PC3; or GATA-binding protein 2 (GATA2) deficiency due to mutations in GATA2. Other genetically-defined conditions without myeloid maturation arrest at the myelocyte/promyelocyte stage are also included in this definition.

Neutropenias Such as Chronic Idiopathic Neutropenia (CIN), Severe Chronic Neutropenia (SCN), and Autoimmune Neutropenia (AIN)

Chronic neutropenia is defined as neutropenia lasting for at least 3 months. The term "idiopathic" indicates that the neutropenia is not attributable to drugs or an identified genetic, infectious, inflammatory, autoimmune, or malignant causes. Thus, the diagnosis of chronic idiopathic neutropenia (CIN) is one made by exclusion of other causes. Finally, the neutropenia is "severe" when the absolute neutrophil count (ANC) is below 500 cells/μL. There is also overlap of patients with the diagnosis of CIN and "autoimmune neutropenia" (AIN) because it is difficult to accurately detect circulating antibodies directed toward antigens present on the surface of neutrophils, and clinical interpretation of the anti-neutrophil antibody test result is also difficult. (Dale, Current Opin Hematol, 2018). The estimated adult prevalence of severe chronic idiopathic neutropenia is approximately 5 per million (Dale and Bolyard (2017) Curr. Opin. Hematol. 24:46-53). There is a female predominance of CIN (Kyle and Linman (1968) N. Engl. J. Med. 279:1015-1019). Distinct pathophysiologic mechanisms have been found, including decreased production, enhanced peripheral removal, and excessive margination of neutrophils (Greenberg et al. (1980) Blood 55:915-921). Neutrophil counts <500 cells/μL are associated with a higher risk of infections. In one study, the bone marrow was analyzed in approximately one third of a series of patients and results were normal in 34% of patients; late maturation arrest was seen in 31% of the patients; granulocytic hypoplasia was observed in 15% of the patients; and 20% of the patients had increased cellularity (Sicre de Fontbrune 2015). A randomized, controlled trial of G-CSF for treatment of severe chronic neutropenia, including 42 patients with CIN, established G-CSF as an effective therapy for this condition (Dale (1993) Blood 81:2496-2502).

In some embodiments, treatment of particular sub-populations of patients with mavorixafor, or a pharmaceutically acceptable salt thereof, is particularly effective.

In some embodiments, the patient is male. In some embodiments, the patient is female.

In some embodiments, the patient is less than 50 years old. In some embodiments, the patient is at least 50 years old.

In some embodiments, the patient has previously been treated with G-CSF.

In some embodiments, the mavorixafor, or a pharmaceutically acceptable salt thereof, and the G-CSF, or another granulocyte-colony stimulating factor treatment such as those described herein, act synergistically. Synergism includes, for example, more effective treatment of the disease than with either agent alone; or a lower dose of one or both agents providing effective treatment for the disease than would be the case if either agent were used alone.

In some embodiments, the patient has not previously been treated with G-CSF prior to commencing treatment with mavorixafor, or a pharmaceutically acceptable salt thereof.

In some embodiments, the patient is currently being treated with G-CSF. In some embodiments, the dose and/or frequency of administration of G-CSF (while maintaining effectiveness of the treatment regimen) is/are reduced after treatment with mavorixafor, or a pharmaceutically acceptable salt thereof, is commenced. In some embodiments, treatment with G-CSF is completely discontinued (while maintaining effective treatment of the patient's neutropenia) after commencing treatment with mavorixafor, or a pharmaceutically acceptable salt thereof.

In some embodiments, the patient has idiopathic neutropenia. In some embodiments, the patient has severe idiopathic neutropenia. In some embodiments, the patient has chronic neutropenia. In some embodiments, the patient has SCN, CIN, or AIN. In some embodiments, the patient has undergone genetic testing but no diagnosis of a genetic abnormality has been made. In some embodiments, the genetic testing was inconclusive. In some embodiments, the genetic testing revealed no known genetic abnormality, or a genetic abnormality not associated with neutropenia. In some embodiments, the patient has neutropenia not due to a genetic abnormality and due to one or more of an infectious, inflammatory, autoimmune, or malignant cause. In some embodiments, the malignant cause is a cancer.

In some embodiments, the patient has severe congenital neutropenia, suspected aplastic anemia, B-cell immunodeficiency, juvenile myelodysplastic syndrome (MDS), chronic myelomonocytic leukemia, a severe Epstein-Barr virus infection or Epstein-Barr-associated cancers, B-cell acute lymphoblastic leukemia, or unexplained bone marrow failure.

In some embodiments, the patient has undergone genetic testing and a genetic abnormality other than one associated with WHIM syndrome has been diagnosed. In some embodiments, the patient has a congenital neutropenia. In some embodiments, the patient has a genetic abnormality selected from GSD1b, G6PC3 deficiency, GATA2 deficiency, a genetically-defined condition without myeloid maturation arrest at the myelocyte/promyelocyte stage, or an undefined genetic abnormality.

Glycogen Storage Disease 1b

Glycogen storage disease type 1b (GSD1b) is an autosomal recessive disorder with an incidence of 2 per million (Chou and Mansfield (2003) in: Broer and Wagner, eds. *Membrane Transporter Diseases. New York: Springer;* 191-205). It is caused by homozygous or compound heterozygous mutations in the SLC37A4 gene coding for the ubiquitously expressed glucose 6-phosphate (G6P) transporter (G6PT). The G6PT enzyme is a transmembrane protein providing a selective channel between the endoplasmic reticulum lumen and the cytosol. The G6PT translocates G6P from the cytoplasm into the lumen of the endoplasmic reticulum in glucose-6-phosphatase (G6Pase)-α or by a ubiquitously expressed G6Pase-β. In neutrophils and macrophages, the G6PT/G6Pase-βcomplex preserves energy homeostasis and functionality (Chou et al. (2010) Curr. Opin. Hematol. 17:36-42). Specifically, the enzyme is made up of 3 separate transporting subunits referred to as G6PT1 (subunit 1), G6PT2 (subunit 2), and G6PT3 (subunit 3). Subunit 1, G6PT1, transports G6P from the cytosol into the lumen of the endoplasmic reticulum where it is hydrolyzed by the catalytic subunit of G6Pase. After hydrolysis, glucose and inorganic phosphate are transported back into the cytosol by G6PT2 and G6PT3, respectively (Parker (2001) Drugs Fut. 26:687). The absence of a functional G6PT1 enzyme causes the disease GSD1b.

Because neutrophil function is linked to the regulation of glucose and G6P metabolism by the G6PT/G6Pase-βcomplex, most of GSD1b patients present with neutropenia, neutrophil dysfunction, and recurrent infections in the context of a broader metabolic disorder also characterized by hypoglycemia, excessive glycogen accumulation in the liver and kidney, and abnormal metabolic serum profiles. Up to 77% of neutropenic patients also develop inflammatory bowel disease (IBD).

A collaborative European study showed that 54 of a cohort of 57 GSD1b patients had neutropenia. Of these, 64% were first neutropenic before the age of 1 year, and a further 18% became neutropenic between the ages of 6 to 9 years (Visser et al. (2000) J Pediatr. 137:187-91). Neutrophils from GSD1b patients exhibit impaired mobility, chemotaxis, and calcium mobilization, as well as diminished respiratory burst and phagocytotic activities. Human GSD1b neutrophils have been found to show signs of apoptosis with increased caspase activity, condensed nuclei, and perinuclear clustering of mitochondria to which the proapoptotic BCL2 member BCL2 associated X had translocated already (Kim et al. (2008) Blood. 111:5704-11). G-CSF added to in vitro cultures did not rescue the GSD1b neutrophils from apoptosis as occurred with G-CSF (Ueno et al. (1986) Eur J Pediatr. 145:312-14; Roe et al. (1986) J Pediatr 109:55-9). In patients, the bone marrow aspirations show hypercellularity due to myeloid hyperplasia and resulting from an arrest of myeloid maturation.

Neutropenia and/or neutrophil dysfunctions predispose GSD1b patients to frequent bacterial infections, aphthous stomatitis and inflammatory bowel disease. (Melis et al. (2014) Italian J. Pediatrics 40:30). Splenomegaly is the dose-limiting adverse event (AE) in GSD1b patients treated with G-CSF, leading to pain and early satiety. While clinical observations and records attest to reduced frequency of infectious events, fever and recurrent infections remain a significant problem despite G-CSF treatment. In one study, the majority of patients being treated with G-CSF developed myelodysplasia (MDS) or acute myeloid leukemia (AML). (Dale et al. (2019) Curr Opin Hematol. 26:16-21; Visser et al. (2000); Visser et al. (2002) Eur J Pediatr. 161 (Suppl 1):S83-7). Without wishing to be bound by theory, it is believed that the development of AML in GSD1b patients may be linked to chronic G-CSF use or to the natural course of the disease or a combination of both (Chou et al. (2010) Curr Opin Hematol. 17:36-42).

G6PC3 Deficiency

The G6PC3 gene encodes the ubiquitously expressed G6PC3. In 2009, Boztug showed that effective function of G6PC3 underlies a severe congenital neutropenia syndrome associated with cardiac and urogenital malformations (Boztug et al. (2009) N Engl J Med. 360:32-43).

As of 2013, 57 patients with G6PC3 deficiency have been described in the literature (Banka and Newman (2013) Orphanet J Rare Dis. 8:84). There have been 91 cases reported globally with an estimated incidence of 0.4 in 1,000,000 births and primarily of Turkish, Pakistani, and French descent. G6PC3 deficiency usually presents in the first few months of life with recurrent bacterial infections and ANC counts ranging from 120 to 550 cells/µL (McDermott et al. (2010) Blood. 116:2793-802). The first serious infection can occur at any age, ranging from immediately after birth to adulthood (Banka (2015, in Gene Reviews, Adam et al, editors. University of Washington, Seattle; 1993-2019). Reported common bacterial infections are respiratory tract infections, otitis media, stomatitis, urinary tract infections, pyelonephritis, skin abscesses, cellulitis, and sepsis. G6PC3 deficiency varies in its severity and associated clinical features. It may present as non-syndromic, with isolated severe congenital neutropenia or, more frequently, syndromic, with cardiovascular and/or urogenital features. A subset of those with syndromic disease present a severe form (Dursun syndrome), due to the additional involvement of myeloid cells, characterized by primary pulmonary hypertension in the newborn period and minor dysmorphic features (Banka 2015). While it is estimated that nearly 10% of G6CP3 deficiency is the non-syndromic form, this could be an underestimate due to ascertainment bias (i.e., selection of more severe phenotypes for testing of G6PC3 in previous studies) (Banka 2013). It is also possible that some patients who initially present with the non-syndromic form may develop features of the classic form later in life (Banka 2015). While bone marrow analysis may show maturation arrest in the myeloid lineage, other G6PC3 deficiency patients may have hyper- or normo-cellular marrows (McDermott 2010; Banka et al. (2011) Am J Hematol. 86:235-7).

GATA2 Deficiency

GATA2 deficiency is an autosomal dominant bone marrow failure disorder with systemic features caused by heterozygous germline mutation in 1 of 2 copies of the GATA2 gene encoding the GATA2 protein. Germline GATA2 mutations have been detected among patients presenting with severe congenital neutropenia, suspected aplastic anemia, B-cell immunodeficiency, juvenile myelodysplastic syndrome (MDS), chronic myelomonocytic leukemia, severe Epstein-Barr virus infections and Epstein-Barr-associated cancers, B-cell acute lymphoblastic leukemia, and other unexplained cases of bone marrow failure (Crispino and Horwitz (2017) Blood. 129:2103-10). In 2017 and 2018, 457 cases of GATA2 deficiency were reported globally. Patients presented with varying ANC levels of 1100 to 8460 cells/µL (Maciejewski-Duval et al. (2016) J Leukoc Bio. 99:1065-76) and often low lymphocyte levels from 112 to 1987 cells/µL (Vinh et al. (2010) Blood. 115:1519-29) or 490 to 2900× $10^6$/mL (Maciejewski-Duval 2016). The bone marrow of patients with GATA2 deficiency has been reported to range from a hypocellular marrow with normal cytogenetics to hypercellular marrow with unfavorable cytogenetics to overt AML with 85% monoblasts (Hickstein (2018) Blood. 131: 1272-74). The GATA 2 deficiency phenotype ranges from immunodeficiency to aplastic anemia to MDS to leukemia (Hickstein 2018).

The diagnosis is further challenging because of the observation that while germline mutations in GATA2 are responsible for GATA2 deficiency, acquired mutations are seen in MDS, AML, and in blast crisis transformation of chronic myeloid leukemia. In fact, GATA2 deficiency is currently the most common hereditary cause of MDS in children and adolescents. The natural history of GATA2 deficiency is highly variable, even in individuals with identical mutations. Infectious complications are common in GATA2 deficiency and result from the selective cellular deficiency profile, namely deficiency of monocytes, natural killer cells, and B lymphocytes. Hematologic manifestations of GATA2 deficiency are mainly progressive cytopenias, with a possible progression from a normocellular marrow to hypocellular MDS or AML.

Approximately half of patients with GATA2 deficiency receive allogeneic hematopoietic stem cell transplant (Hickstein 2018), and allogeneic stem cell transplantation is the only curative therapy for GATA2 deficiency. There are no clear guidelines regarding the monitoring schedule or the ideal prophylaxis for asymptomatic GATA2 patients. However, proposals include monitoring peripheral blood counts every 3 to 6 months and bone marrow biopsy with cytogenetics every 1 to 2 years and to transplant before the development of severe end organ damage or leukemia (Hsu et al. (2015) Curr. Opin. Allergy Clin. Immunol. 15:104-9).

Mavorixafor may prove a useful bridge to transplant because of the potential to improve both the neutropenia and the lymphopenia in these patients.

Combination of G-CSF and CXCR4 Inhibition for Treatment of Chronic Neutropenia

Granulocyte colony-stimulating factor is currently the standard of care for severe chronic neutropenia (SCN). Indeed, in patients diagnosed with chronic neutropenia, particularly those with severe neutropenia with ANC<500 cells/µL, daily (or multiple times a week) injections of G-CSF are commonly given to increase the ANC and reduce the risk of infections. The efficacy of G-CSF in this indication was proven by a placebo-controlled clinical trial that demonstrated G-CSF safety and efficacy in reducing the risk of infection in patients with SCN of various etiologies (Dale et al. (1993) Blood. 81:2496-502).

For treatment of severe, chronic neutropenia, Neupogen® (filgrastim or G-CSF) is indicated at a starting dosage 6 mcg/kg as a twice daily subcutaneous injection (congenital neutropenia); or 5 mcg/kg as a single daily subcutaneous injection (idiopathic or cyclic neutropenia). It is further indicated that the starting dosage by followed by chronic daily administration in order to maintain clinical benefits. The indicated chronic daily administration is in the amount of 6 mcg/kg (congenital neutropenia); 2.1 mcg/kg (cyclic neutropenia); and 1.2 mcg/kg (idiopathic neutropenia). Neulasta® (pegfilgrastim or pegylated G-CSF) is not presently approved for treatment of severe, chronic neutropenia other than in patients receiving myelosuppressive chemotherapy or radiation. It is available in a 6 mg/0.6 mL single-dose prefilled syringe, which may be administered once per chemotherapy cycle, or in two doses of 6 mg each, one week apart, for subjects who have been exposed to radiation levels in excess of 2 gray (Gy). Neulasta® is also available for use with the "on-body injector" or OBI, which is co-packaged with a prefilled syringe, and which administers the Neulasta® dose over a period of approximately 45 minutes, beginning approximately 27 hours after the OBI is applied to the subject's skin.

Bone pain experienced with administration of G-CSF has commonly been treated with acetaminophen and nonsteroidal anti-inflammatory agents as first line therapy, while antihistamines, such as loratidine (10 mg oral); or combinations of famotidine and loratadine; opioids; and dose reduction of G-CSFs are considered as second line therapy (Lambertini et al. (2014) Crit. Rev. Oncol. Hematol. 89:112-128).

Without wishing to be bound by theory, it is believed that G-CSF's effect on the bone marrow release of neutrophils is mediated in part by interfering with CXCL12 availability at the level of the CXCR4 receptor, with minimal effects on other hematopoietic cell types.

Granulocyte-colony stimulating factor treatment induces a decrease in CXCL12 expression in the bone marrow (Semerad et al. (2002) Immunity. 17:413-23; Levesque et al. (2003) J Clin Invest. 111:187-96), and G-CSF leads to decreased surface expression of CXCR4 on neutrophils (Kim et al. (2006) Blood. 108:812-20). In fact, G-CSF does not stimulate neutrophil release from the bone marrow in the absence of CXCR4 signals (Eash et al. (2009) Blood. 113:4711-19).

Without wishing to be bound by any particular theory, it is believed that certain patient populations having neutropenia could be treated effectively with a combination of specific CXCR4 inhibitors, such as mavorixafor, and G-CSF; or with a CXCR4 inhibitor, such as mavorixafor, alone. It is further believed that such treatment produces a significant increase in patient baseline ANC. It is also believed that subjects with neutropenia (or severe neutropenia) who are currently treated with G-CSF, including those subjects who experience bone pain or other serious adverse effects of receiving G-CSF, could be treated with a CXCR4 inhibitor, such as mavorixafor, and that treatment with CXCR4 inhibitor allows for a reduction in the dosage and/or frequency of treatment with G-CSF, or even elimination of the need for treatment with G-CSF, while still maintaining an ANC above a minimum threshold (e.g., ANC of at least 500/μL) to prevent infections and other manifestations of neutropenia (e.g., oral ulcers).

Combination with Mavorixafor

In some embodiments of the present invention, mavorixafor is administered orally (PO) to the patient at a dose regimen of about 400 mg once daily (QD).

In some embodiments, the dosage of CXCR4 inhibitor is a well-tolerated dose that achieves a satisfactory therapeutic result, without causing any severe or treatment-limiting toxicities.

As used herein, the term "well-tolerated" in reference to a dose of mavorixafor or other CXCR4 inhibitor means a dose that can be given to a patient without the patient experiencing any treatment-limiting toxicities. As used herein, "treatment-limiting toxicities" (TLTs) means that the patient experiences one or more of the toxicities in Table 1:

TABLE 1

| Treatment-Limiting Toxicities | |
|---|---|
| Toxicity | Treatment-Limiting Toxicity Criteria |
| Hematology | Grade 4 neutropenia lasting more than 7 consecutive days |
| | Grade 3 or 4 neutropenia with fever (temperature of >38.5° C.) |
| | Grade 4 thrombocytopenia, or Grade 3 thrombocytopenia with bleeding |
| | Grade 4 anemia |
| | Grade 4 lymphopenia |
| Non-Hematology Events | Any ≥Grade 3 clinical events or laboratory events, except for the events described below, which are TLTs only if they meet the criteria below. |
| Gastrointestinal | Grade 3 or 4 nausea, vomiting, or diarrhea lasting ≥48 hours despite optimal medical management |
| Hepatobiliary | ≥Grade 2 total bilirubin elevation with ≥ Grade 2 ALT/AST elevation |
| | ≥Grade 3 ALT/AST elevation lasting ≥5 days or Grade 4 ALT/AST elevation |

TABLE 1-continued

| Treatment-Limiting Toxicities | |
|---|---|
| Toxicity | Treatment-Limiting Toxicity Criteria |
| Pneumonitis | Grade 2 pneumonitis lasting >7 days despite optimal treatment |
| Hypertension | Grade 3 hypertension lasting >7 days despite optimal treatment |
| Infection | Grade 3 infection or fever in the absence of neutropenia lasting >5 days |
| Electrolytes | Grade 3 electrolyte abnormalities lasting >7 days |
| Rash and/or photosensitivity | ≥Grade 3 rash or photosensitivity lasting >7 days despite optimal treatment |
| Fatigue | Grade 3 electrolyte abnormalities lasting >7 days |
| Immune-related toxicities (except pneumonitis) | Grade 3 immune related toxicities lasting >7 days despite optimal treatment |
| Others | Any other ≥ Grade 2 toxicity that, in the opinion of a treating physician is considered to be a clinically unacceptable risk |

Grading: As defined by the National Cancer Institute [NCI] Common Terminology Criteria for Adverse Events, version 4.03).
Abbreviations: ALT = alanine aminotransferase; AST = aspartate aminotransferase; TLT = treatment-limiting toxicity.

Effective targeted treatments for neutropenia, like mavorixafor, are needed for the management of patients because, for example, of the significant side effects associated with G-CSF. Mavorixafor can be administered orally (PO) once daily (QD), which in addition to being a targeted treatment, makes it an excellent candidate in a chronic treatment setting that would be required for patients with SCN or CIN. In some embodiments, mavorixafor is administered orally (PO) once daily (QD). In some embodiments, mavorixafor is administered orally (PO) twice daily (BD).

Treatment of Neutropenia Such as SCN, CIN, and AIN with Mavorixafor and Treatment Duration Under basal conditions, most neutrophils reside in the bone marrow, and this pool of neutrophils can be mobilized into the blood physiologically in response to infection or stress, or upon CXCR4 antagonist administration, providing a mechanism to rapidly increase neutrophil delivery to sites of infection. Humans and mice treated with a selective CXCR4 antagonist rapidly mobilize neutrophils into the blood (Liles 2003; Suratt 2004; Broxmeyer et al. (2005) J. Exp. Med. 201:1307-1318). Transgenic mice carrying a myeloid-specific deletion of CXCR4 display marked neutrophilia, thus confirming the key role of CXCR4 signaling in the regulation of neutrophil homeostasis. CXCR4 maintains neutrophil homeostasis primarily by regulating neutrophil release from the bone marrow (Eash 2009).

It is anticipated that most patients seeking treatment for chronic neutropenia and severe CIN will currently be receiving treatment with G-CSF, because this is the present standard of care (Dale, Blood 1993). However, in certain embodiments, a subject may be treated with mavorixafor alone, or in combination with therapies other than G-CSF, including, but not limited to, pegylated G-CSF (peg-filgrastim) and other variants of G-CSF, GM-CSF (sargramostim), pegylated GM-CSF (peg-sargramostim) and other variants of GM-CSF. CIN patients have also been treated with corticosteroids, gamma globulin, methotrexate, cyclosporine, and other agents (Dale, Curr Opin Hematol. 2017 January; 24(1): 46-53). In some embodiments, the patient has been previously treated, or is currently being treated, with a corticosteroid, gamma globulin, methotrexate, or cyclosporine. In some embodiments, the patient has CIN.

While neutrophils have been reported to have a very short half-life of 8 to 16 hours under basal conditions (Lord 1991; Dresch 1975), new information has shown that under homeostatic conditions, the average circulatory neutrophil lifespan is 5.4 days (Pillay 2010). Today it is estimated that mature neutrophils have a typical circulating half-life of 6-8 h in the blood and then migrate through tissues for ~2-3 days. Their relatively short lifespan is devoted largely to surveillance for invading microorganisms. During infection, the neutrophil lifespan is extended, granulopoiesis increases, and large numbers of neutrophils are rapidly recruited to the site(s) of infection (*Neutrophil Methods and Protocols*, Third Edition, Mark T. Quinn, Humana Press, 2020). CXCL12/CXCR4 signaling plays a key role in controlling neutrophil homeostasis (Link 2005) and CXCR4 is a key regulator of neutrophil release from the bone marrow under basal and stress granulopoiesis conditions (Eash et al., Blood 2009). The generation of a mature neutrophil from the myeloblast stage takes approximately 14 days. Bainton et al., (1971) J. Exp. Med. 134:907-34.

Treating Neutropenia and Related Disorders

Effective targeted treatments for neutropenia, like mavorixafor, are needed for the management of patients. Mavorixafor can be administered orally (PO) and once-daily (QD), which in addition to being a targeted treatment, makes it an excellent candidate in a chronic treatment setting that would be required for patients with SCN or CIN.

The cognate ligand for the CXCR4 receptor is stromal cell-derived factor 1-alpha (SDF-1α), also known as C-X-C motif chemokine 12 (CXCL12), which is involved with numerous physiologic processes and plays a central role in hematopoietic cell homing to, and release from, the bone marrow (Lapidot 2002). In patients with WHIM syndrome, gain-of-function mutations in the CXCR4 gene prevent the normal release of mature neutrophils from the bone marrow into the blood (Kawai 2005).

CXCR4 is a G protein-coupled receptor and engagement by SDF-1α induces typical activation of G protein-dependent pathways of a chemokine receptor (Baggiolini 1998, Zlotnik 2000). These processes are regulated in a timely manner by the recruitment of β-arrestin to the receptor that precludes further G-protein activation (i.e., desensitization) and leads to receptor internalization.

Mavorixafor is a small molecule antagonist of CXCR4 having the potential to block the enhanced signaling activity of wild-type and mutant CXCR4 receptors, resulting in an increase in the number of circulating white blood cells.

In some embodiments, mavorixafor or a pharmaceutically acceptable salt thereof is dosed by oral administration of up to 400 mg daily. In some embodiments, the dose is selected to provide consistent clinically relevant elevations of both ANC and ALC, with low risk of significant adverse effects. Dosage of 400 mg per day BID for 3.5 days (healthy volunteers) (Stone 2007) and 200 mg BID for 8-10 days (healthy volunteers and HIV patients) were well-tolerated with no pattern of adverse events or clinically significant laboratory changes. These studies also demonstrated pharmacodynamics activity, with dose- and concentration-related changes in circulating white blood cells (WBCs); and a high volume of distribution (VL), suggesting high tissue penetrance.

The inventors conceived that CXCR4 antagonism by mavorixafor may provide significant treatment benefits in patients with neutropenia, particularly for patients with chronic neutropenia, including congenital neutropenia and severe congenital neutropenia, and severe chronic idiopathic neutropenia (CIN) as described in the present application.

Administration of mavorixafor inhibits SDF-1α (CXCL12) binding to CXCR4 and CXCR4+CEM-CCRF cells. Administration of mavorixafor also inhibits CXCR4 cell signaling and SDF-1α induced calcium flux. In this manner, X4P-001 inhibits SDF-1α stimulated CCRF-CEM chemotaxis.

Moreover, the inventors conceived that such a result might be achieved with comparatively little toxicity since CXCR4-targeted drugs are specifically targeted and do not induce cell cycle arrest in normal proliferating cell populations. Accordingly, the present invention provides significant advantages in treatment outcomes utilizing the effects and the low toxicity of the CXCR4 inhibitor mavorixafor (also known as X4P-001; AMD070; or AMD11070).

Thus, in one aspect, the present invention provides a method of treating neutropenia, comprising administering to a patient in need thereof an effective amount of mavorixafor or a pharmaceutically acceptable salt or composition thereof in combination with a standard of care treatment. In some embodiments, the standard of care treatment is G-CSF or GM-CSF.

In another aspect, the present invention provides a method for treating a patient with neutropenia at risk of infections, comprising administering to the patient an effective amount of mavorixafor or a pharmaceutically acceptable salt or composition thereof.

In another aspect, the present invention provides a method for reducing the dosage of G-CSF for treating severe chronic neutropenia (SCN) in a patient in need thereof, comprising administering to the patient an effective amount of mavorixafor or a pharmaceutically acceptable salt or composition thereof.

In some embodiments, the patient has an absolute neutrophil count (ANC) less than about 500 cells/µL.

In some embodiments, patients with neutropenia, such as patients with SCN or CIN, or a related disease, are treated with an effective amount of mavorixafor, or a pharmaceutically acceptable salt or composition thereof, either as a single agent (monotherapy), or in combination with other treatments for neutropenia (combination therapy). In some embodiments, the combination therapy comprises treatment with an effective amount of granulocyte colony-stimulating factor (G-CSF), granulocyte-macrophage colony-stimulating factor (GM-CSF), a variant of G-CSF or GM-CSF (e.g., a pegylated version), bone marrow transplantation, treatment with cord blood stem cells, or a combination thereof.

In some embodiments, G-CSF is co-administered to the patient at a starting dosage of about 6 mcg/kg as a twice daily subcutaneous injection (for a patient having congenital neutropenia); or about 5 mcg/kg as a single daily subcutaneous injection (for a patient having idiopathic or cyclic neutropenia). In some embodiments, the patient is already receiving G-CSF and continues chronic dosing at a dosage sufficient to maintain clinical benefits, such as daily administration in the amount of about 6 mcg/kg (for patients having congenital neutropenia); about 2.1 mcg/kg (for patients having cyclic neutropenia); or about 1.2 mcg/kg (for patients having idiopathic neutropenia).

For treatment of severe, chronic neutropenia, Neupogen® (filgrastim or G-CSF) is indicated at a starting dosage 6 mcg/kg as a twice daily subcutaneous injection (congenital neutropenia); or 5 mcg/kg as a single daily subcutaneous injection (idiopathic or cyclic neutropenia). It is further indicated that the starting dosage by followed by chronic daily administration in order to maintain clinical benefits. The indicated chronic daily administration is in the amount of 6 mcg/kg (congenital neutropenia); 2.1 mcg/kg (cyclic neutropenia); and 1.2 mcg/kg (idiopathic neutropenia). Neulasta® (pegfilgrastim or pegylated G-CSF) is not presently approved for treatment of severe, chronic neutropenia other than in patients receiving myelosuppressive chemotherapy or radiation. It is available in a 6 mg/0.6 mL single-dose prefilled syringe, which may be administered once per chemotherapy cycle, or in two doses of 6 mg each, one week apart, for subjects who have been exposed to radiation levels in excess of 2 gray (Gy). Neulasta® is also available for use with the "on-body injector" or OBI, which is co-packaged with a prefilled syringe, and which administers the Neulasta® dose over a period of approximately 45 minutes, beginning approximately 27 hours after the OBI is applied to the subject's skin.

In another aspect, the present invention provides a method for treating neutropenia, comprising administering to a patient in need thereof an effective amount of mavorixafor, or a pharmaceutically acceptable salt or composition thereof, in combination with an effective amount of G-CSF or GM-CSF, or a variant thereof, wherein the effective amount of G-CSF or GM-CSF, or a variant thereof is less than the approved dosage as a monotherapy for a similar patient being treated with the G-CSF or GM-CSF, or a variant thereof.

In some embodiments, a disclosed method features a decrease in the incidence of bone pain in the patient, or across a representative group of patients. In some embodiments, a disclosed method features a decrease in the incidence of flu-like symptoms in the patient, or across a representative group of patients. In some embodiments, a disclosed method features a decrease in the incidence of a myeloid malignancy, such as such as myelodysplasia (MDS) or acute myeloid leukemia (AML), in the patient, or across a representative group of patients. Bone pain is estimated to occur in anywhere from 24% and (reported on filgrastim and pegfilgrastim labels, respectively) to as high as 66% for filgrastim [Ferguson (2015), Practical Pain Management, vol. online at: practical painmanagement.com/treatments/pharmacological/non-opioids/antihistamine-g-csf-induced-bone-pain] and 59% (24% severe bone pain) for pegfilgrastim (Kirshner et al. (2012) J. Clin Oncol. 30:1974-79). G-CSF is also associated with flu-like symptoms. Further, a link between G-CSF and myeloid malignancies, such as myelodysplasia (MDS) or acute myeloid leukemia (AML) has been reported.

It is anticipated by the inventors that administration of mavorixafor will permit reduction or discontinuation of the G-CSF for at least some patients. In some cases, this reduces the risk of G-CSF associated malignancy and myelofibrosis, and reduces G-CSF associated bone pain while maintaining protection from infection.

In some embodiments, the neutropenia is SCN. In some embodiments, the neutropenia is CIN. In some embodiments, the neutropenia is AIN. In some embodiments, the neutropenia is caused by an autoimmune disorder such as systemic lupus erythematosus (SLE).

In another aspect, the present invention provides a method of treating chronic idiopathic neutropenia (CIN), severe chronic idiopathic neutropenia (SCN), or autoimmune neutropenia (AIN), comprising administering to a patient in need thereof mavorixafor, or a pharmaceutically acceptable salt or composition thereof.

In some embodiments, a provided method comprises administering the mavorixafor, or a pharmaceutically acceptable salt or composition thereof, to a patient in a fasted state.

In some embodiments, the mavorixafor is in the form of a free base. In some embodiments, the mavorixafor is in the form of a pharmaceutically acceptable salt.

In some embodiments, the patient has previously been treated with G-CSF.

In some embodiments, the mavorixafor, or a pharmaceutically acceptable salt or composition thereof, and the G-CSF, or another granulocyte-colony stimulating factor treatment such as those described herein, act synergistically. In some embodiments, the synergism comprises a more effective treatment of the disease than with either agent alone. In some embodiments, the synergism comprises a lower dose of one or both agents providing effective treatment for the disease than would be the case if either agent were used alone.

In some embodiments, the patient has not previously been treated with G-CSF prior to commencing treatment with mavorixafor, or a pharmaceutically acceptable salt or composition thereof.

In some embodiments, the patient is currently being treated with G-CSF. In some embodiments, the dose and/or frequency of administration of G-CSF (while maintaining effectiveness of the treatment regimen) is/are reduced after treatment with mavorixafor, or a pharmaceutically acceptable salt thereof, is commenced. In some embodiments, treatment with G-CSF is completely discontinued (while maintaining effective treatment of the patient's neutropenia) after commencing treatment with mavorixafor, or a pharmaceutically acceptable salt thereof.

In some embodiments, the patient has idiopathic neutropenia. In some embodiments, the patient has severe idiopathic neutropenia. In some embodiments, the patient has chronic neutropenia. In some embodiments, the patient has SCN, CIN, or AIN. In some embodiments, the patient has undergone genetic testing but no diagnosis of a genetic abnormality has been made. In some embodiments, the genetic testing was inconclusive. In some embodiments, the genetic testing revealed no known genetic abnormality, or a genetic abnormality not associated with neutropenia. In some embodiments, the patient has neutropenia not due to a genetic abnormality and due to one or more of an infectious, inflammatory, autoimmune, or malignant cause. In some embodiments, the malignant cause is a cancer.

In some embodiments, the patient has severe congenital neutropenia, suspected aplastic anemia, B-cell immunodeficiency, juvenile myelodysplastic syndrome (MDS), chronic myelomonocytic leukemia, a severe Epstein-Barr virus infection or Epstein-Barr-associated cancers, B-cell acute lymphoblastic leukemia, or unexplained bone marrow failure.

In some embodiments, the patient has undergone genetic testing and a genetic abnormality other than one associated with WHIM syndrome (e.g., a gain-of-function mutation in the CXCR4 gene) has been diagnosed. In some embodiments, the patient has a congenital neutropenia. In some embodiments, the patient has a genetic abnormality selected from GSD1b, G6PC3 deficiency, GATA2 deficiency, a genetically-defined condition without myeloid maturation arrest at the myelocyte/promyelocyte stage, or an undefined genetic abnormality.

In some embodiments, a provided method further comprises the step of obtaining a biological sample from the patient and measuring the amount of a disease-related biomarker. In some embodiments, the biological sample is a blood sample. In certain embodiments, the disease-related biomarker is selected from the group consisting of CXCR4, SDF-1α/CXCL12; and GRK3 (G protein coupled receptor kinase 3).

The dose level and regimen may be set by the treating clinician, and typically depends on factors such as the age, weight, sex, and general health of the patient. In some embodiments, mavorixafor, or a pharmaceutically acceptable salt thereof, is administered in an oral dose, such as PO QD, of from about 25 mg/day to about 1200 mg/day. In some embodiments, the daily dose is from about 50 mg/day to about 800 mg/day; from about 100 mg/day to about 800 mg/day; from about 150 mg/day to about 800 mg/day; from about 200 mg/day to about 800 mg/day; from about 250 mg/day to about 800 mg/day; from about 300 mg/day to about 800 mg/day; from about 350 mg/day to about 800 mg/day; or from about 400 mg/day to about 800 mg/day.

In some embodiments, the daily dose is from about 100 mg/day to about 600 mg/day; from about 200 mg/day to about 600 mg/day; from about 300 mg/day to about 500 mg/day; or from about 350 mg/day to about 450 mg/day. In a particular embodiment, mavorixafor or a pharmaceutically acceptable salt thereof is administered in a daily dose of about 400 mg/day PO QD. Although the daily dose is preferably administered once daily, the clinician may also choose to divide the dose into two or more parts taken at intervals during the day. For example, a daily dose may be divided into two parts, with one half of the daily dose administered in the morning, and the second half of the daily dose administered in the afternoon or evening. The interval between halves of the daily dose may be from 4 hours to about 16 hours; preferably from about 5 hours to about 15 hours; or more preferably from about 6 hours to about 14 hours; from about 7 hours to about 13 hours; or from about 8 hours to about 12 hours.

In some embodiments, cells taken from the patient exhibit increased expression of CXCR4.

In some embodiments, the method further comprises the step of obtaining a biological sample from the patient and measuring the amount of a disease-related biomarker.

In some embodiments, the biological sample is a blood sample.

In some embodiments, the disease-related biomarker is ANC, ALC, total White Blood Cell counts (WBC), or circulating CXCR4.

In some embodiments, the mavorixafor or a pharmaceutically acceptable salt or composition thereof is administered orally (PO) once per day (QD).

In some embodiments, the mavorixafor or a pharmaceutically acceptable salt or composition thereof is administered orally (PO) twice per day (BID).

In some embodiments, a disclosed method comprises administering a mavorixafor unit dosage form comprising a composition comprising:
 (a) mavorixafor, or a pharmaceutically acceptable salt thereof, as about 10-20% by weight of the composition;
 (b) microcrystalline cellulose as about 70-85% by weight of the composition;
 (c) croscarmellose sodium as about 5-10% by weight of the composition;
 (d) sodium stearyl fumarate as about 0.5-2% by weight of the composition; and
 (e) colloidal silicon dioxide as about 0.1-1.0% by weight of the composition.

In some embodiments, the unit dosage form is in capsule form.

In some embodiments, the dosage form comprises about 25 mg mavorixafor, or a pharmaceutically acceptable salt thereof. In other embodiments, the dosage form comprises about 50 mg; 100 mg; 200 mg; 300 mg; 400 mg; 500 mg; 600 mg; or 800 mg mavorixafor, or a pharmaceutically acceptable salt thereof.

In some embodiments, the present invention provides a method for treating neutropenia, such as SCN or CIN, in a patient in need thereof, comprising the step of administering to the patient a disclosed unit dosage form.

In some embodiments, the present invention provides a method for treating neutropenia, such as SCN or CIN, in a patient in need thereof, comprising administering to said patient mavorixafor, or a pharmaceutically acceptable salt or composition thereof, in an amount effective to increase absolute neutrophil count (ANC) and/or to increase absolute lymphocyte count (ALC) in the patient, for example in the patient's blood. In some embodiments, the ANC and/or ALC is increased in the patient by at least 10%, 15%, 20%, 25%, 30%, 35%, 40%, 45% or at least 50% of that of the pre-treatment baseline counts.

In some embodiments, the present invention provides a method for treating neutropenia, such as SCN or CIN, in a patient in need thereof, comprising administering to said patient mavorixafor or a pharmaceutically acceptable salt or composition thereof, in an amount effective to increase absolute neutrophil count (ANC) to a level greater than or equal to 500/μL and/or to increase absolute lymphocyte count (ALC) to a level greater than or equal to 1000/μL.

In some embodiments, said patient originally exhibits ANC less than 600/μL and/or ALC less than 1000/μL before treatment with mavorixafor, or a pharmaceutically acceptable salt or composition thereof.

In some embodiments, said patient originally exhibits ANC less than 500/μL and/or ALC less than 650/μL before treatment with mavorixafor or a pharmaceutically acceptable salt or composition thereof.

In some embodiments, a disclosed method results in increases in ANC levels to at least about 500/μL, at least about 600/μL, at least about 700/μL, at least about 800/μL, at least about 900/μL, at least about 1000/μL, at least about 1,100/μL, or at least about 1,200/μL, or to about that of a human with a normally-functioning immune system, on at least 85% of assessments.

In some embodiments, a disclosed method results in increases in ALC to at least about 1000/μL, about 1,200/μL, or about 1,500/μL, or to about that of a human with a normally-functioning immune system, on at least 85% of assessments.

In some embodiments, a disclosed method results in a lowered frequency of infections in the patient, such as at least 10%; at least 25%; or at least 50% less infections. In some embodiments, the method reduces the frequency of a respiratory tract infection.

In some embodiments, a disclosed method results in increased levels of total circulating WBC, neutrophils, and/or lymphocytes. In some embodiments, cell counts of WBC, neutrophils, and/or lymphocytes increase to approximately 1.4× baseline. In some embodiments, cell counts of WBC, neutrophils, and/or lymphocytes increase to approximately 1.6× baseline, 1.8× baseline, or 2.0× baseline. In some embodiments, cell counts of WBC, neutrophils, and/or lymphocytes increase to approximately 2.9× baseline. In some embodiments, cell counts of lymphocytes increase to approximately 2.9× baseline. In some embodiments, cell counts of neutrophils increase to approximately 2.7× baseline and lymphocytes to approximately 1.9× baseline.

In some embodiments, the present invention provides a method of treating neutropenia, such as SCN or CIN, in a patient in need thereof, wherein said method comprises administering to said patient an effective amount of mavorixafor or a pharmaceutically acceptable salt or composition thereof in conjunction with another treatment for neutropenia, such as SCN or CIN.

In some embodiments, the present invention provides a method of treating neutropenia, such as SCN or CIN, in a patient in need thereof, wherein said patient has been either receiving no treatment or receiving regular or preventative treatment with G-CSF, or a variant thereof. The method comprises administering to said patient an effective amount of mavorixafor. The timing of administration of mavorixafor may be prior to, together with, or subsequent to administration of G-CSF, or a variant thereof.

In certain embodiments, after commencement of administration of mavorixafor, the dosage of G-CSF administered to said patient may be reduced, while maintaining absolute neutrophil counts (ANC) equal to or higher than 500 cells/μL.

In certain embodiments, the dosage of G-CSF that is administered to the patient is reduced by at least about 25% relative to the patient's previous dose before beginning treatment with mavorixafor or a pharmaceutically acceptable salt or composition thereof. In certain embodiments, the dosage of G-CSF that is administered to the patient is reduced by at least about 50%, 75%, or 95% relative to the patient's previous dose before beginning treatment with mavorixafor or a pharmaceutically acceptable salt or composition thereof. In certain embodiments, the dosage of G-CSF or GM-CSF, or variant thereof, that is administered to the patient is reduced by about 10%, 15%, 20%, 25%, 30%, 35%, 40%, 50%, 55%, 60%, 65%, 70%, 75%, 80%, 85%, 90%, or 95%.

In certain embodiments, the frequency of dosage of G-CSF or GM-CSF or variant thereof is reduced, for example, reduced in frequency by at least 25%, 50%, 75%, or 90%.

In certain embodiments, administration of G-CSF or GM-CSF, or variant thereof, may be eliminated, or administered only in the event of a crisis, for example, if ANC levels drop below cells/μL. Decreased dosage of G-CSF or GM-CSF, or variant thereof, can be effected by lowering the doses administered at any one time and/or by increasing the interval between dosage administration, e.g., once every three days, rather than once every two days.

In some embodiments, the patient begins with a well-tolerated dose of oral, daily mavorixafor, for example, 400 mg per day, wherein the patient is presently receiving a full dose (1×) of G-CSF or peg-G-CSF. The patient is typically monitored for ANC. In some embodiments, if the patient's ANC is at or above 1000 cells/μL, patient's dose of G-CSF or peg-G-CSF is reduced by a factor of approximately 25%, (i.e., to 0.75× dose). In some embodiments, if ANC remains at or above 1000 cells/μL, then (a) the patient's dose of G-CSF or peg-G-CSF is further reduced; (b) the daily dosage of mavorixafor being administered is increased or decreased; or both (a) and (b). Typically, at such time, ANC will continue to be monitored, with a goal of ANC of at least cell/μL being maintained. As long as the patient's ANC remains above 500 cells/μL, the patient's dose of G-CSF or peg-G-CSF is optionally further reduced. In some embodiments, the method reduces bone pain or other adverse effects of G-CSF or peg-G-CSF.

If the patient's measured ANC is found to be between 500 and 1000 cells/μL, (a) the patient's dose of G-CSF or peg-G-CSF is further reduced; (b) the daily mavorixafor dosage is increased; or both (a) and (b). In some embodiments, the method provides maintenance of an ANC of at least 500 cell/μL. In some embodiments, as long as the patient's ANC remains above 500 cells/μL, the patient's dose of G-CSF or peg-G-CSF is optionally further reduced. In some embodiments, the method reduces bone pain or other adverse effects of G-CSF or peg-G-CSF.

Dosage and Formulations

Mavorixafor

CXCR4 inhibitors such as the compound mavorixafor (previously known as X4P-001, AMD070, or AMD11070) or a pharmaceutically acceptable salt thereof or pharmaceutical composition thereof, as described in greater detail below, are useful both as a monotherapy and as a combination therapy with one or more other therapeutic agents described herein. Accordingly, in one aspect, the present invention provides a method of treating neutropenia, such as those described herein, by administering to a patient in need thereof an effective amount of a CXCR4 inhibitor such as mavorixafor, or a pharmaceutically acceptable salt thereof or pharmaceutical composition thereof. In some embodiments, the method further includes co-administering simultaneously or sequentially an effective amount of one or more additional therapeutic agents, such as those described herein.

Mavorixafor (formerly known as X4P-001, AMD 070, or AMD11070) is a small molecule antagonist of CXCR4 having the potential to block the enhanced signaling activity of wild type and mutant CXCR4, resulting in an increase in the number of circulating white blood cells (Leukocytosis) of 2.9-fold (400-mg single-dose subject) above baseline with a peak between and 4 h following dosing (Stone, 2007) by inhibiting CXCR4-dependent interactions between bone marrow stromal cells and mature leukocytes of many lineages thus allowing release of these cells into the circulation (Liles Blood 2003).

Mavorixafor is a second-generation, small-molecule, non-competitive, allosteric antagonist of chemokine receptor type 4 (CXCR4) that acts by binding to extracellular domains of the receptor, resulting in specific and reversible inhibition of receptor signaling in response to its ligand C-X-C motif chemokine ligand 12 (CXCL12). Mavorixafor is currently in clinical development in patients with cancer (renal cell carcinoma), Waldenstrom Macroglobulinemia, and with warts, hypogammaglobulinemia, infections, and myelokathexis (WHIM) syndrome. The chemical formula is: $C_{21}H_{27}N_5$; and molecular weight is 349.48 amu. The chemical structure of mavorixafor is as follows according to Formula I:

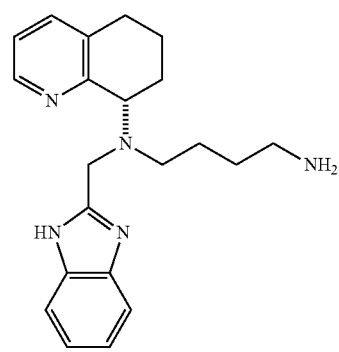

I

As of May 2019, approximately 193 healthy volunteers and patients had been treated with mavorixafor in clinical studies (n=70 healthy volunteers, n=16 HIV, n=99 oncology, n=8 WHIM syndrome). Overall, mavorixafor has been generally well tolerated, with no mavorixafor-related serious AEs (SAEs) causing a fatal outcome in any of the patients.

In certain embodiments, the mavorixafor, pharmaceutically acceptable salt thereof, or composition comprising mavorixafor or a pharmaceutically acceptable salt thereof is administered orally (PO) once daily (QD) or twice daily (BID), in an amount from about 25 mg to about 800 mg daily. In certain embodiments, the dosage composition may be provided twice a day in divided dosage, approximately 12 hours apart. In other embodiments, the dosage composition may be provided once daily. The terminal half-life of mavorixafor has been generally determined to be between about 12 to about 24 hours, or approximately 14.5 hrs. In certain embodiments, the dosage of mavorixafor useful in the invention is from about 25 mg to about 1200 mg daily. In other embodiments, the dosage of mavorixafor useful in the invention may range from about 25 mg to about 1000 mg daily, from about 50 mg to about 800 mg daily, from about 50 mg to about 600 mg daily, from about 50 mg to about 500 mg daily, from about 50 mg to about 400 mg daily, from about 100 mg to about 800 mg daily, from about 100 mg to about 600 mg daily, from about 100 mg to about 500 mg daily, from about 100 mg to about 400 mg daily; from about 200 mg to about 800 mg daily, from about 200 mg to about 600 mg daily, from about 300 mg to about 600 mg daily, from about 200 mg to about 500 mg daily from about 200 mg to about 400 mg daily.

In other embodiments, the dosage of mavorixafor or a pharmaceutically acceptable salt thereof is administered in a dosage range from about 100 mg to about 800 mg daily, from about 200 mg to about 600 mg daily, from about 300 mg to about 500 mg daily, or from about 350 mg to about 450 mg daily; or in a daily dosage of about 100 mg/day; 125 mg/day; 150 mg/day; 175 mg/day; 200 mg/day; 225 mg/day; 250 mg/day; 275 mg/day; 300 mg/day; 325 mg/day; 350 mg/day; 400 mg/day; 425 mg/day; 450 mg/day; 475 mg/day; 500 mg/day; 525 mg/day; 550 mg/day; 575 mg/day; 600 mg/day; 625 mg/day; 650 mg/day; 675 mg/day; 700 mg/day; 725 mg/day; 750 mg/day; 775 mg/day or 800 mg/day. In unusual cases, the dosage of mavorixafor or a pharmaceutically acceptable salt thereof may be administered in an amount in excess of 800 mg/day, while taking care to minimize or avoid any adverse effects of such administration.

In some embodiments, a provided method comprises administering to the patient a pharmaceutically acceptable composition comprising mavorixafor wherein the composition is formulated for oral administration. In certain embodiments, the composition is formulated for oral administration in the form of a tablet, a caplet or a capsule. In some embodiments, the composition comprising mavorixafor is formulated for oral administration in the form of a capsule.

In certain embodiments, a provided method comprises administering to the patient one or more dosage forms comprising 25 mg to 1200 mg mavorixafor active ingredient; and one or more pharmaceutically acceptable excipients. In certain embodiments, the capsule is comprised of hard gelatin. In some embodiments the dosage form comprises 25 mg to 800 mg mavorixafor active ingredient, 50 mg to 600 mg mavorixafor active ingredient, 100 mg to 500 mg mavorixafor active ingredient, 100 mg to 400 mg mavorixafor active ingredient, 100 mg to 300 mg mavorixafor active ingredient, or 100 mg to 200 mg mavorixafor active ingredient.

In certain embodiments, a disclosed method comprises administering a composition comprising mavorixafor, or a pharmaceutically acceptable salt thereof, one or more diluents, a disintegrant, a lubricant, a flow aid, and a wetting agent. In some embodiments, a disclosed method comprises administering a composition comprising 25 mg to 1200 mg mavorixafor, or a pharmaceutically acceptable salt thereof, microcrystalline cellulose, dibasic calcium phosphate dihydrate, croscarmellose sodium, sodium stearyl fumarate, colloidal silicon dioxide, and sodium lauryl sulfate. In some embodiments, a disclosed method comprises administering a unit dosage form wherein said unit dosage form comprises a composition comprising 25 mg to 200 mg mavorixafor, or a pharmaceutically acceptable salt thereof, microcrystalline cellulose, dibasic calcium phosphate dihydrate, croscarmellose sodium, sodium stearyl fumarate, colloidal silicon dioxide, and sodium lauryl sulfate. In certain embodiments, a disclosed method comprises administering a unit dosage form comprising a composition comprising mavorixafor, or a pharmaceutically acceptable salt thereof, present in an amount of about 25 mg, about 40 mg, about 50 mg, about 80 mg, about 100 mg, about 150 mg, about 200 mg, about 250 mg, about 300 mg, about 350, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, or about 1200 mg. In some embodiments, a provided composition (or unit dosage form) is administered to the patient once per day, twice per day, three times per day, or four times per day. In some embodiments, a provided composition (or unit dosage form) is administered to the patient once per day or twice per day.

In some embodiments, a disclosed method comprises administering a unit dosage form comprising a composition comprising:
  (a) mavorixafor, or a pharmaceutically acceptable salt thereof, as about 10-30% by weight of the composition;
  (b) microcrystalline cellulose as about 60-80% by weight of the composition;
  (c) croscarmellose sodium as about 5-10% by weight of the composition;
  (d) sodium stearyl fumarate as about 0.5-2% by weight of the composition; and
  (e) colloidal silicon dioxide as about 0.1-1.0% by weight of the composition.

In some embodiments, a disclosed method comprises administering a unit dosage form comprising a composition comprising:
  (a) mavorixafor, or a pharmaceutically acceptable salt thereof, as about 15% by weight of the composition;
  (b) microcrystalline cellulose as about 78% by weight of the composition;
  (c) croscarmellose sodium as about 6% by weight of the composition;
  (d) sodium stearyl fumarate as about 1% by weight of the composition; and
  (e) colloidal silicon dioxide as about 0.2% by weight of the composition.

In some embodiments, a disclosed method comprises administering a unit dosage form comprising a composition comprising:
  (a) mavorixafor, or a pharmaceutically acceptable salt thereof, as about 10-20% by weight of the composition;
  (b) microcrystalline cellulose as about 25-40% by weight of the composition;
  (c) dibasic calcium phosphate dihydrate as about 35-55% by weight of the composition;
  (d) croscarmellose sodium as about 4-15% by weight of the composition;

(e) sodium stearyl fumarate as about 0.3-2% by weight of the composition;
(f) colloidal silicon dioxide as about 0.1-1.5% by weight of the composition; and
(g) sodium lauryl sulfate as about 0.1-1.5% by weight of the composition.

In some embodiments, a disclosed method comprises administering a unit dosage form comprising a composition comprising:
(a) mavorixafor, or a pharmaceutically acceptable salt thereof, as about 13% by weight of the composition;
(b) microcrystalline cellulose as about 32% by weight of the composition;
(c) dibasic calcium phosphate dihydrate as about 44% by weight of the composition;
(d) croscarmellose sodium as about 8% by weight of the composition;
(e) sodium stearyl fumarate as about 1.4% by weight of the composition;
(f) colloidal silicon dioxide as about 0.4% by weight of the composition; and
(g) sodium lauryl sulfate as about 0.7% by weight of the composition.

In some embodiments, a disclosed method comprises administering a unit dosage form comprising a composition comprising:
(a) mavorixafor, or a pharmaceutically acceptable salt thereof, as about 35-75% by weight of the composition;
(b) microcrystalline cellulose as about 5-28% by weight of the composition;
(c) dibasic calcium phosphate dihydrate as about 7-30% by weight of the composition;
(d) croscarmellose sodium as about 2-10% by weight of the composition;
(e) sodium stearyl fumarate as about 0.3-2.5% by weight of the composition; (f) colloidal silicon dioxide as about 0.05-1.2% by weight of the composition; and
(g) sodium lauryl sulfate as about 0.2-1.2% by weight of the composition.

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for co-administration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

The examples below explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

The contents of each document cited in the specification are herein incorporated by reference in their entireties.

EXEMPLIFICATION

Example 1: Non-Clinical Evaluation of X4P-001 Effects on CXCR4: In Vitro Pharmacology The in-vitro pharmacology of X4P-001 (formally designated AMD11070) was extensively studied and the results reported [Mosi 2012]. Presented below is the relevant information from the Mosi 2012 literature publication. The SDF-1α isoform was used for the experiments described below.

X4P-001 Inhibition of SDF-1α Binding to CXCR4

Figure 4:
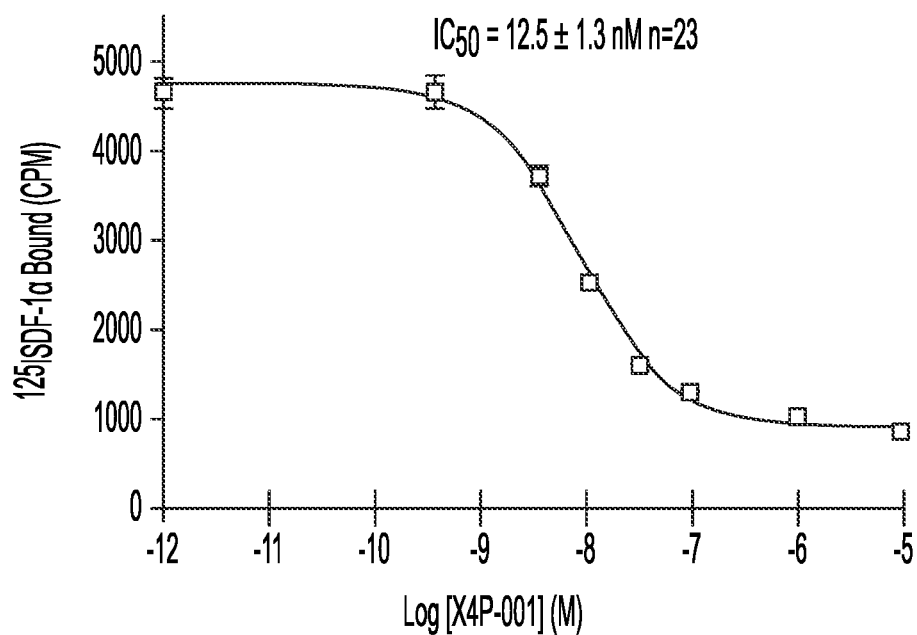
FIG. 4 shows that mavorixafor inhibits binding of [$^{125}$I]-SDF-1α to CCRF-CEM cells (T-lymphoblastoid cell line which naturally express CXCR4 [Crump 1997]) in a heterologous competition binding assay. The data was fitted to a single site binding model and gave an $IC_{50}$ of 12.5±1.3 nM.

X4P-001 was shown to inhibit binding of [125I]-SDF-1α to CCRF-CEM cells (T-lymphoblastoid cell line which naturally express CXCR4 [Crump 1997]) in a heterologous competition binding assay. The results of the assay are shown in FIG. 4. The data was fitted to a single site binding model and gave an IC50 of 12.5±1.3 nM.

X4P-001 Inhibition of CXCR4 Cell Signaling

Figure 5:
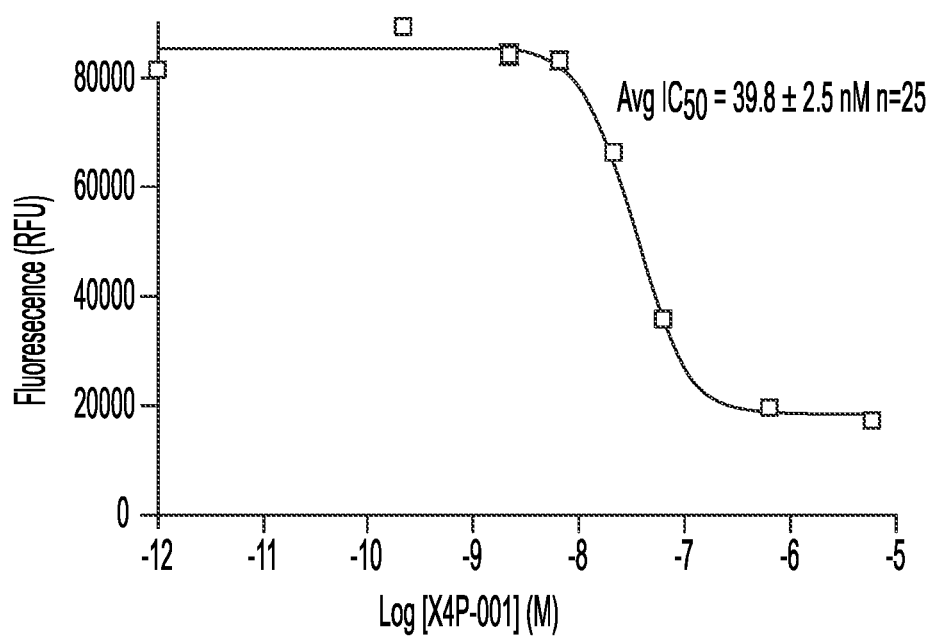
FIGS. 5 and 6 show that mavorixafor inhibits CXCR4 activation with ICso values of 39.8±2.5 nM and 19.0±4.1 nM in the Eu-GTP binding and [$^{35}$S]-GTPγS assays, respectively.
Figure 6:
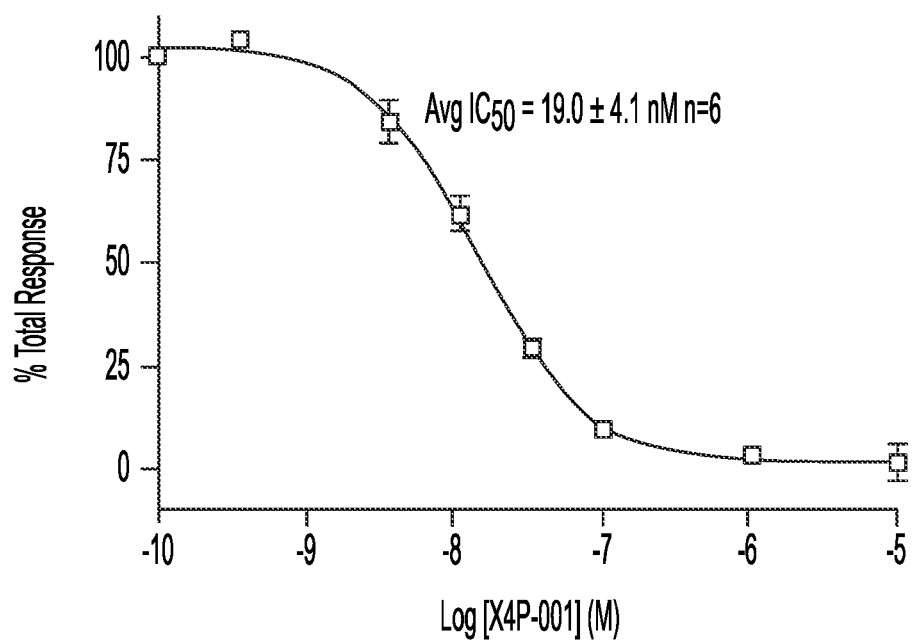

CXCR4 is a G-protein coupled receptor [Baggiolini 1998, Zlotnik 2000]. As such the activation of the receptor can be measured using a nonhydrolysable analogue of GTP such as fluorescently labeled Europium-GTP (Eu-GTP) or radiolabeled [35S]-GTPγS. The results shown in FIG. 5 and FIG. 6 showed that X4P-001 inhibited CXCR4 activation with IC50 values of 39.8 f 2.5 nM and 19.0±4.1 nM in the Eu-GTP binding and [35S]-GTPγS assays, respectively.

Figure 7:
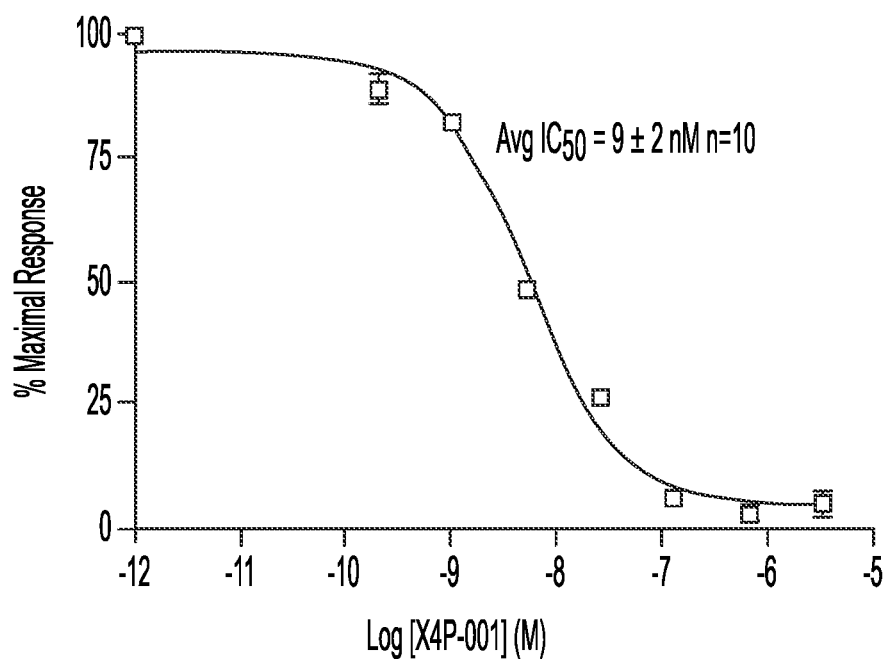
FIG. 7 shows that, upon activation of a G-protein coupled receptor, intracellular signaling pathways are triggered resulting in the release of calcium from intracellular stores. This calcium flux can be assayed using a calcium-chelating molecule, Fluo-4, which fluoresces upon binding calcium. Mavorixafor was able to inhibit SDF-1α (2.5 nM SDF-1α) mediated calcium flux in CCRF-CEM cells with an $IC_{50}$ of 9.0±2.0 nM.

Upon activation of a G-protein coupled receptor, intracellular signaling pathways are triggered resulting in the release of calcium from intracellular stores. This calcium flux can be assayed using a calcium-chelating molecule, Fluo-4, which fluoresces upon binding calcium. X4P-001 was able to inhibit SDF-1α (2.5 nM SDF-1α) mediated calcium flux in CCRF-CEM cells with an IC50 of 9.0±2.0 nM. The result is shown in FIG. 7.

Figure 8:
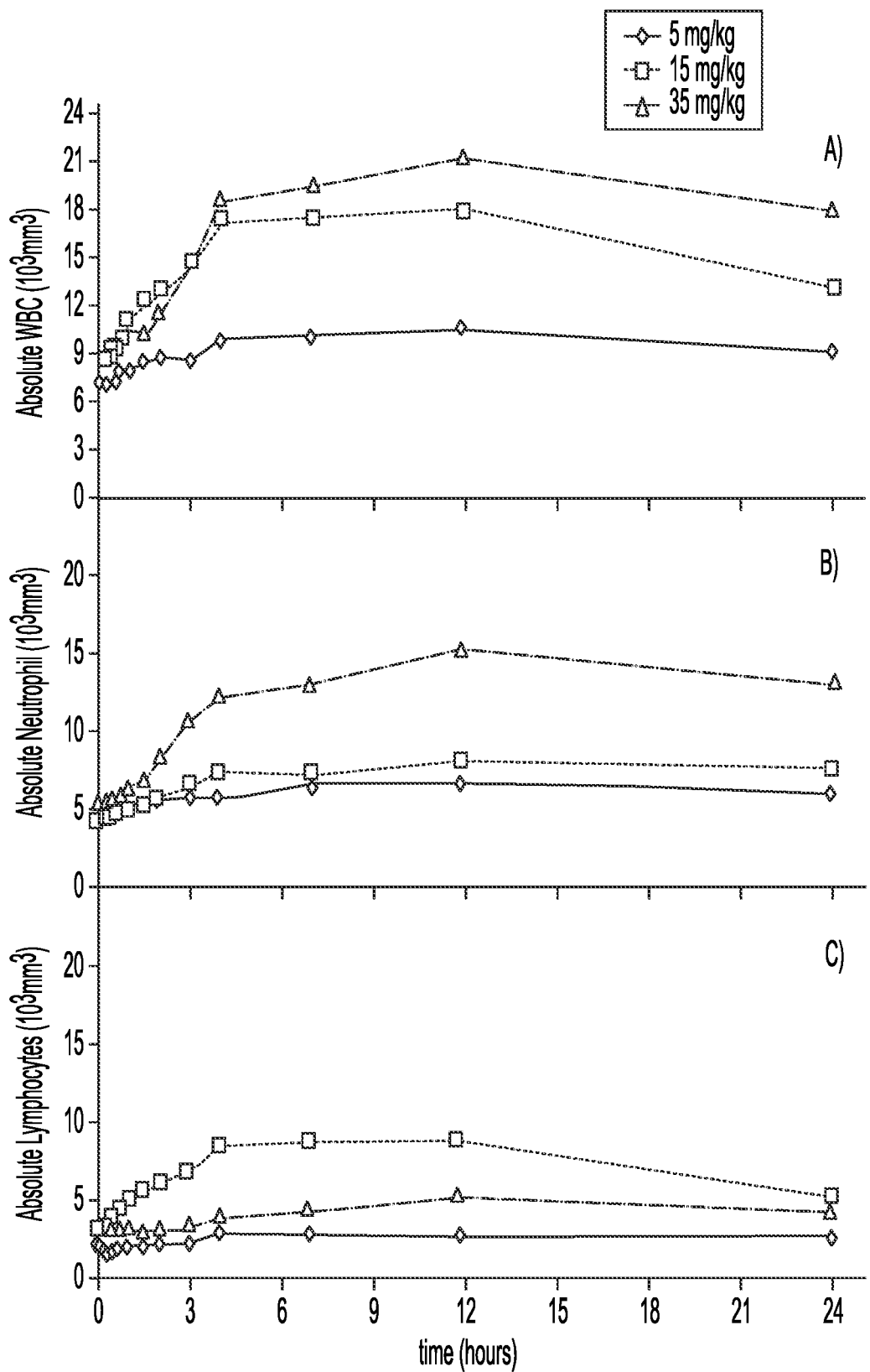
FIG. 8 shows the effect of mavorixafor on WBC and absolute neutrophil and lymphocyte counts in male beagle dogs. Maximal increases in WBC occurred 4-12 hours post-dose. Peak elevations ranged from 1.8-2.9-fold above baseline values at the 15 and 35 mg/kg dose levels, with somewhat lower (1.5-fold) elevations observed at the 5 mg/kg dose level. Although limited by the small sample size, these results suggest that maximal increases may have been achieved at the higher dose levels. WBC, neutrophil, and lymphocyte counts remained elevated at the 15 and 35 mg/kg dose levels at 24 hours, with evidence of return to baseline. No other hematological effects were observed.

A key property of all chemokines is that they induce a chemotactic response to a chemokine concentration gradient. X4P-001 was able to inhibit SDF-1α mediated chemotaxis of CCRF-CEM cells with an IC50 of 19.0±4.0 nM as shown in FIG. 8.

A summary of the above in vitro results is presented in Table 2 below:

TABLE 2

In Vitro Concentrations of X4P-001(IC50) Associated with Different Biological Responses

| Response | $IC_{50}$ (nm) |
|---|---|
| Ligand Binding | 12.5 ± 1.3 |
| Eu-GTP | 39.8 ± 2.5 |
| [$^{35}$S]-GTP | 19.0 ± 4.1 |
| Calcium Flux | 9.0 ± 2.0 |
| Chemotaxis | 19.0 ± 4.0 |
| Average $IC_{50}$ | 21.5 |

Mavorixafor Selectivity for CXCR4

In order to demonstrate the specificity of X4P-001 for CXCR4 it was tested in calcium signaling assays against a panel of chemokine receptors, and in ligand binding assays for BLT1, the receptor for leukotriene B4 (LTB4), and CXCR7. LTB4 is a potent chemoattractant and its receptor is a G-protein coupled receptor. The results in Table 3 show that the ICso of X4P-001 against CCR1, CCR2b, CCR4, CCR5, CCR7, CXCR3, and LTB4 was >50 mM in all cases. X4P-001 did not inhibit SDF-1α binding to CXCR7 at a concentration of 10 mM, the maximum concentration tested in this assay. Together, these data indicate that X4P-001 is a selective inhibitor of CXCR4.

TABLE 3

Calcium Flux Response for Cell Lines Treated with Mavorixafor for IC50 Determination

| Receptor | Cell line | Ligand | $IC_{50}$ Mavorixafor (μM) |
| --- | --- | --- | --- |
| CCR1 | HEK293F-CCR1 | MIP-1α/CCL3 | >50 |
| CCR2b | HEK293F-CCR2b | MCP-1/CCL2 | >50 |
| CXCR3 | HEK293F-CXCR3-Gαq15 | IP-10/CXCL10 | >50 |
| CXCR7 | Cf2Th.CXCR7 | SDF-1α/CXCL12 | >10 |
| CCR4 | HEK293F-CCR4-Gαq15 | TARC/CCL17 | >50 |
| CCR5 | HEK293F-CCR5 | RANTES/CCL5 | >50 |
| CCR7 | CCRF-CEM | MIP-3β/CCL19 | >50 |
| $BLT_1$ | CHO-S-$LTB_4$ | $LTB_4$ | >50 |

Discussion and Conclusions from In Vitro Studies

Using the CCRF-CEM cell line, which naturally expresses CXCR4 [Crump 1997] it was shown that X4P-001 inhibits SDF-1α ligand binding to CXCR4 with an IC50 of 12.5±1.3 nM. X4P-001 also inhibited CXCR4 activation and signaling as shown by inhibition of SDF-1α mediated G-protein activation of the CXCR4 receptor in two assays using either the fluorescent Eu-GTP or the radiolabeled [35S]-GTPγS binding assays with $IC_{50}$ values of 39.8±2.5 nM and 19.0±4.1 nM, respectively, and inhibition of SDF-1α mediated calcium flux with an IC50 of 9.0±2.0 nM. X4P-001 also inhibited SDF-1α-mediated chemotaxis, a CXCR4-mediated physiological response, with an IC50 of 19.0±4.0 nM. In addition, X4P-001 had little or no inhibitory effect on either MIP1α, MCP-1, TARC, RANTES, MIP-3p, or IP10 mediated calcium flux, ligands for CCR1, CCR2b, CCR4, CCR5, CCR7 and CXCR3, respectively, or SDF-1α binding to CXCR7, or LTB4 binding to BLT1, an alternative G-protein coupled receptor that mediates chemotaxis. These data indicate that X4P-001 is a selective inhibitor of CXCR4 over the other chemokine receptors evaluated.

Additionally, it was shown that X4P-001 is an allosteric inhibitor of CXCR4 by comparing the dose/response of SDF-1α in the calcium flux assay in the presence of increasing amounts of X4P-001 [Mosi 2012]. Based on inhibition being mediated by non-competitive binding, the extent of inhibition is therefore dependent solely on the concentration of X4P-001 and is independent of the concentration of SDF-1α ligand.

In-Vivo Pharmacology

The primary in vivo pharmacologic effect of X4P-001 is mobilization of white blood cells (WBC) from bone marrow. Three studies are summarized below which demonstrate the mobilization of WBC from the bone marrow of beagle dogs and $C_3W$/He J mice.

Hematologic Effects in the Male Beagle Dog

Three fasted male Beagle dogs received a single dose of X4P-001 in aqueous solution by oral gavage at dose levels of 5, 15, and 35 mg/kg (1 dog per dose level) in a volume of mL/kg. Blood samples (approximately 3 mL each) were obtained at multiple timepoints from each animal by direct venipuncture of the jugular vein and collected using Vacutainer® tubes containing K3EDTA as the anticoagulant. Blood samples were obtained at pre-dose, and 0.25, 0.5, 0.75, 1, 1.5, 2, 3, 4, 7, 12, and 24 hours post-dose. Blood samples were stored at ambient room temperature prior to automated differential analysis.

Body weights were determined prior to dosing on the day of test article administration. Animals were observed at least once daily and at times of blood sampling.

Hematology parameters included the following:

White Blood Cell Count (WBC)

Differential white blood cell count (absolute and relative)

Neutrophil

Lymphocytes

Monocytes

Eosinophils

Basophils

Large Unstained Cells (LUC)

Hematocrit (HCT)

Hemoglobin (HGB)

Mean Corpuscular Hemoglobin (MCH)

Mean Corpuscular Hemoglobin Concentration (MCHC)

Mean Corpuscular Volume (MCV)

Platelet Count (PLT)

Red Blood Cell Count (RBC)

Results

The effect of X4P-001 on WBC and absolute neutrophil and lymphocyte counts is shown in FIG. 8. Maximal increases in WBC occurred 4-12 hours post-dose. Peak elevations ranged from 1.8-2.9-fold above baseline values at the 15 and 35 mg/kg dose levels, with somewhat lower (1.5-fold) elevations observed at the 5 mg/kg dose level. Although limited by the small sample size, these results suggest that maximal increases may have been achieved at the higher dose levels. WBC, neutrophil, and lymphocyte counts remained elevated at the 15 and 35 mg/kg dose levels at 24 hours, with evidence of return to baseline. No other hematological effects were observed.

A 28-Day Oral (Capsule) Study in the Beaale Dog with a 14-Day Recovery Period

A 28-Day GLP oral (capsule) toxicology study was conducted with X4P-001 in the male and female beagle dog, and hematology effects were observed, with X4P-001 administered twice-daily (at least 7 hours apart) by oral capsule for 28 days. A subset of treated animals was evaluated after a 14-day recovery period. Table 4 presents the protocol design and Table 5 the evaluations schedule.

TABLE 4

Protocol Design for 28-Day Toxicity Study in the Dog

| Group | Dose Level (mg/kg/day)[a] | Animals Terminal Necropsy | Animals 14-day Recovery |
| --- | --- | --- | --- |
| 1 | 0 (empty capsule) | 3 M, 3 F | 2 M, 2F |
| 2 | 10 | 3 M, 3 F | — |
| 3 | 30 | 3 M, 3 F | — |

TABLE 5

Protocol Evaluations and Schedules

| Evaluations | Schedule |
|---|---|
| Study Duration | Days −10 through Day 42 |
| Treatment | Days 1 through 28, twice daily |
| Clinical Observation | Twice Daily |
| Food Consumption | Daily |
| Body Weight | Weekly |
| Vital Signs[a] | Predose acclimation period; final dosing week; final recovery week |
| Ophthalmology | Predose and during Week 4 |
| Electrocardiogram Evaluation | Predose and during Week 4, at ~1 hour post-first daily dose |
| Clinical Pathology[b] | Predose d−10, d−2; Post-dose, Day 29 (all groups), Day 42 (recovery only) |
| Necropsy[c] | Day 29, terminal; Day 42, recovery |

[a]Vital signs comprise heart rate, blood pressure, and body temperature
[b]Clinical pathology comprised hematology, coagulation, serum, and urinalysis (done only once predose).
[c]Necropsy studies comprise organ weight, macroscopic, and microscopic observations, including 500-cell bone marrow differential count.

As shown in Table 6 below, increases in absolute counts for neutrophils, lymphocytes, and monocytes were observed at termination (Day 28); these were of greater magnitude and more likely statistically significant in females. These changes were considered consistent with the pharmacological effects of X4P-001. After the 14-day recovery period (only 100 mg/kg dose group evaluated) all hematology results returned to within normal levels.

TABLE 6

Hematology Findings at Termination in 28-Day Oral Toxicity Study in the Dog

| Observation | 10 mg/kg/d (3 M, 3 F) | 30 mg/kg/d (3 M, 3 F) | 100 mg/kg/d (3 M, 3 F) |
|---|---|---|---|
| Hematology | | | |
| Neutrophils (abs) | M incr 1.2x; F incr 1.9x† | M incr 1.2x; F incr 2.3x† | M incr 1.8x; F incr 2.8x† |
| Lymphocytes (abs) | M incr 1.3x; F incr 1.4x | M incr 1.6x; F incr 1.6x† | M incr 2.3x†; F incr 1.4x† |
| Monocytes (abs) | M incr 1.2x; F incr 1.6x† | M incr 1.3x; F incr 1.9x† | M incr 1.9x†; F incr 2.4x† |
| Reticulocytes | No changes | No changes | F decr 0.24† |
| Coagulation | No changes | No changes | No changes | abs, absolute;
†p < 0.05 compared with control animals of the same sex

Hematologic Effects of X4P-001 in Mice

A further study was conducted to determine whether X4P-001 mobilizes progenitor/stem cells in mice. All experiments were performed in C3W/He J mice. X4P-001 and AMD3100/plerixafor were administered via single subcutaneous injection at the doses described below. The mobilization capacity of X4P-001 was assessed by the numbers of granulocyte-macrophage (CFU-GM), erythroid (BFU-E) and multipotential (CFU-GEMM) progenitor cells per mL of blood. The progenitors were stimulated to form colonies in vitro with the combination of 1 U/mL rhu EPO, 50 ng/mL rmu SLF, 5% vol/vol pokeweed mitogen mouse spleen cell conditioned medium (PWMSCM), and 0.1 mM hemin. Plates were scored 7 days after incubation at 37° C., 5% $C_{O2}$, lowered (5% CO2) and in a humidified chamber.

Results

X4P-001 mobilized progenitors in C3H/HeJ mice following a single subcutaneous injection. In the first experiment (data shown in Table 7), mice received a dose of 5 mg/kg- and the number of progenitors in the circulating blood was measured at various time points (0.25, 0.5, 1, 2, 6 and 24 hours). The peak of nucleated cell mobilization occurred at approximately 1-2 hours post-injection. Peak increases of CFU-GM, BFU-E and CFU-GEMM were 4.21 (30 min.), 2.49-2.54 (30-60 min.), and 2.58-2.67 (30-60 min.)-fold, respectively over control (saline injection).

TABLE 7

X4P-001 Time Course of Progenitor Mobilization

| | | | Mavorixafor Time Course (dose = 5 mg/kg) | | | | | |
|---|---|---|---|---|---|---|---|---|
| | | Control | @ - 15" | @ - 30" | @ - 60" | @ - 2' | @ - 6' | @ - 24' |
| Nucleated | Mean | 4.35 | 5.10 | 6.14 | 6.92 | 8.29 | 5.66 | 4.31 |
| Cellularity | STD | 0.14 | 1.09 | 1.20 | 0.57 | 0.55 | 0.28 | 0.82 |
| (×10⁶/mL) | STE | 0.08 | 0.63 | 0.69 | 0.33 | 0.32 | 0.16 | 0.47 |
| PBL-LD | Fold Chg | 1.00 | 1.17 | 1.41 | 1.59 | 1.90 | 1.30 | 0.99 |
| | P | 1.000 | 0.307 | 0.062 | 0.002 | 0.000 | 0.002 | 0.930 |
| GM | Mean | 302.3 | 785.1 | 1273.8 | 866.0 | 897.5 | 387.5 | 386.3 |
| | STD | 20.5 | 180.3 | 85.4 | 197.8 | 165.6 | 54.6 | 110.5 |
| | STE | 11.8 | 104.1 | 49.3 | 114.2 | 95.6 | 31.5 | 63.8 |
| | Fold Chg | 1.00 | 2.60 | 4.21 | 2.86 | 2.97 | 1.28 | 1.28 |
| | P | 1.000 | 0.010 | 0.000 | 0.008 | 0.003 | 0.065 | 0.265 |
| BFU | Mean | 92.5 | 148.8 | 230.4 | 235.1 | 165.3 | 99.9 | 84.6 |
| | STD | 30.9 | 27.1 | 70.2 | 68.2 | 47.5 | 17.8 | 44.4 |
| | STE | 17.8 | 15.6 | 40.5 | 39.4 | 27.4 | 10.3 | 25.7 |
| | Fold Chg | 1.00 | 1.61 | 2.49 | 2.54 | 1.79 | 1.08 | 0.92 |
| | P | 1.000 | 0.076 | 0.036 | 0.030 | 0.090 | 0.735 | 0.814 |

TABLE 7-continued

X4P-001 Time Course of Progenitor Mobilization

|  |  |  | Mavorixafor Time Course (dose = 5 mg/kg) | | | | | |
|---|---|---|---|---|---|---|---|---|
|  |  | Control | @ - 15" | @ - 30" | @ - 60" | @ - 2' | @ - 6' | @ - 24' |
| GEMM | Mean | 38.6 | 65.6 | 99.6 | 103.1 | 68.9 | 37.6 | 37.7 |
|  | STD | 10.6 | 17.6 | 24.2 | 20.3 | 23.7 | 16.0 | 20.6 |
|  | STE | 6.1 | 10.2 | 14.0 | 11.7 | 13.7 | 9.3 | 11.9 |
|  | Fold Chg | 1.00 | 1.70 | 2.58 | 2.67 | 1.78 | 0.97 | 0.98 |
|  | P | 1.000 | 0.085 | 0.016 | 0.008 | 0.114 | 0.934 | 0.946 |

Animals per group = 3,
control group = 1,
total animals = 21

An X4P-001 dose-response was performed by measurement of the number of circulating progenitors in the blood at 1 hour post-injection at various doses (1.5, 2.5, 5, 10 and 20 mg/kg). As shown in Table 8, there appears to be an upper limit to the number of progenitors that can be mobilized with X4P-001, exemplified by the fold increases of CFU-GM. The numbers of CFU-GM in the circulating blood dose-dependently increased with peak fold increase of 6.0-7.7 over control at 5-20 mg/kg. Peak fold increases respectively of 2.3 and 3.8 for BFU-E and CFU-GEMM were noted at 10 mg/kg. At doses below 5 mg/kg X4P-001, the fold-increases in the numbers of BFU-E and CFU-GEMM were not statistically significant.

TABLE 8

Dose Response in C3H/HeJ Mice

|  |  |  | Mavorixafor (mg/kg) | | | | |
|---|---|---|---|---|---|---|---|
|  |  | Control | 20 | 10 | 5 | 2.5 | 1.5 |
| Nucleated | Mean | 6.48 | 9.62 | 9.94 | 7.65 | 8.29 | 6.94 |
| Cellularity | STD | 0.69 | 1.26 | 4.02 | 2.74 | 2.07 | 0.50 |
| ($\times 10^6$/mL) | STE | 0.40 | 0.73 | 2.32 | 1.58 | 1.20 | 0.29 |
| PBL-LD | Fold Chg | 1.00 | 1.48 | 1.53 | 1.18 | 1.28 | 1.07 |
|  | P | 1.000 | 0.019 | 0.216 | 0.514 | 0.225 | 0.406 |
| GM | Mean | 188.0 | 1314.2 | 1444.2 | 1119.8 | 626.5 | 428.0 |
|  | STD | 51.8 | 262.0 | 939.8 | 1011.9 | 220.4 | 118.7 |
|  | STE | 29.9 | 151.2 | 542.6 | 584.2 | 127.3 | 68.5 |
|  | Fold Chg | 1.0 | 7.0 | 7.7 | 6.0 | 3.3 | 2.3 |
|  | P | 1.000 | 0.002 | 0.082 | 0.186 | 0.028 | 0.033 |
| BFU | Mean | 114.4 | 261.4 | 268.1 | 181.6 | 144.8 | 143.8 |
|  | STD | 5.6 | 35.8 | 61.4 | 58.6 | 79.3 | 47.1 |
|  | STE | 3.2 | 20.7 | 35.5 | 33.8 | 45.8 | 27.2 |
|  | Fold Chg | 1.0 | 2.3 | 2.3 | 1.6 | 1.3 | 1.3 |
|  | P | 1.000 | 0.002 | 0.012 | 0.119 | 0.544 | 0.343 |
| GEMM | Mean | 58.4 | 145.0 | 224.4 | 141.0 | 78.3 | 53.3 |
|  | STD | 45.5 | 50.5 | 60.7 | 34.4 | 8.1 | 8.9 |
|  | STE | 26.3 | 29.2 | 35.0 | 19.8 | 4.7 | 5.1 |
|  | Fold Chg | 1.0 | 2.5 | 3.8 | 2.4 | 1.3 | 0.9 |
|  | P | 1.000 | 0.092 | 0.019 | 0.066 | 0.498 | 0.857 |

Animals per group = 3,
control group 1,
total animals = 18

A final experiment was performed to compare the progenitor cell mobilization capacity of X4P-001 and AMD3100/plerixafor. Both drugs were administered subcutaneously at a dose of 5 mg/kg, and the number of progenitors in the circulating blood were measured for AMD3100 at a single 1 hour time point (the peak of mobilization with AMD3100, data not shown) versus X4P-001 at 0.25, 0.5, 1 and 2 hours post-injection. As shown in Table 9 comparing the fold-increase in CFU-GM, BFU-E, and CFU-GEMM, AMD3100 caused respective maximum increases of 9.11, 3.12, and 4.35, whereas respective peaks of mobilization with X4P-001 were 3.56, 2.84 and 3.21.

TABLE 9

Mavorixafor Time Course Compared to AMD3100/Plerixafor (Dose 5mg/kg)

|  |  | Control | AMD3100 @ - 60" | Mavorixafor @ - 15" | Mavorixafor @ - 30" | Mavorixafor @ - 60" | Mavorixafor @ - 2' |
|---|---|---|---|---|---|---|---|
| Nucleated Cellularity ($\times 10^6$/mL) | Mean | 6.23 | 10.08 | 8.04 | 8.28 | 7.34 | 9.71 |
|  | STD | 2.16 | 2.13 | 1.30 | 0.94 | 0.69 | 1.29 |
|  | STE | 1.25 | 1.23 | 0.75 | 0.54 | 0.40 | 0.74 |
| PBL-LD | Fold Chg | 1.00 | 1.62 | 1.29 | 1.33 | 1.18 | 1.56 |
|  | P | 1.000 | 0.092 | 0.281 | 0.205 | 0.444 | 0.074 |
| GM | Mean | 214.1 | 1950.3 | 588.3 | 705.9 | 761.4 | 619.6 |
|  | STD | 118.2 | 566.4 | 168.1 | 151.5 | 239.2 | 158.7 |
|  | STE | 68.2 | 327.0 | 97.1 | 87.5 | 138.1 | 91.6 |
|  | Fold Chg | 1.00 | 9.11 | 2.75 | 3.30 | 3.56 | 2.89 |
|  | P | 1.000 | 0.007 | 0.034 | 0.011 | 0.024 | 0.024 |
| BFU | Mean | 66.5 | 207.7 | 188.9 | 151.9 | 144.3 | 108.5 |
|  | STD | 39.6 | 35.4 | 55.0 | 23.8 | 47.5 | 43.0 |
|  | STE | 22.9 | 20.4 | 31.7 | 13.8 | 27.4 | 24.8 |
|  | Fold Chg | 1.00 | 3.12 | 2.84 | 2.29 | 2.17 | 1.63 |
|  | P | 1.000 | 0.010 | 0.035 | 0.033 | 0.095 | 0.281 |
| GEMM | Mean | 31.8 | 138.5 | 93.8 | 79.0 | 102.2 | 62.4 |
|  | STD | 2.6 | 18.1 | 21.1 | 34.5 | 50.5 | 34.9 |
|  | STE | 1.5 | 10.5 | 12.2 | 19.9 | 29.1 | 20.1 |
|  | Fold Chg | 1.00 | 4.35 | 2.95 | 2.48 | 3.21 | 1.96 |
|  | P | 1.000 | 0.001 | 0.007 | 0.078 | 0.074 | 0.205 |

Animals per group = 3,
control group = 1,
total animals = 18

Conclusions from In Vivo Studies

Single oral doses of X4P-001 at 5, 15, and 35 mg/kg in beagle dogs resulted in increased levels of total circulating WBC, neutrophils, and lymphocytes. The increases were consistently apparent at 4 hours and typically peaked at 12 hours, occasionally earlier. At 5 mg/kg, all three cell counts increased to 1.47× baseline. At 15 mg/kg, neutrophils increased to 1.8× and lymphocytes to 2.9λ; and at 35 mg/kg, neutrophils to 2.7× and lymphocytes to 1.9×.

In multiple-dose toxicity studies in dogs, hematological effects after 28 days were qualitatively and quantitatively consistent with the findings in the single dose study in beagle dogs.

In C3H/HeJ mice, X4P-001 dose-dependently increased the number of circulating progenitors up to a dose of 5-10 mg/kg s.c.

Example 2: Clinical Protocol: Patients to be Treated

Patients with Severe CIN or Selected Congenital Neutropenias and Treated with Prophylactic G-CSF Patients who may be treated in the study described below include patients with either a severe form of CIN or selected congenital neutropenia disorders.

To be eligible for treatment with mavorixafor in the present study, patients with severe CIN must have a history of ANC<500 cells/µL, lasting for more than 3 months at any time since diagnosis; and must have been diagnosed with severe CIN more than 12 months ago that is not attributable to medications, infectious, genetic, inflammatory, autoimmune, or malignant causes. In this particular trial, the patients must be currently treated with a prophylactic steady-state G-CSF regimen for >15 days before receiving the first dose of mavorixafor, must have normal cytogenetics on the most recent bone marrow biopsy/aspirate, if performed; and must have no associated thrombocytopenia nor anemia before G-CSF therapy initiation.

To be eligible for the specific clinical trial, patients with selected congenital neutropenia conditions, including GSD1b (GSD1b; SLC37A4), G6PC3 deficiency (G6PC3), or GATA2 deficiency (GATA2) may currently be receiving steady-state G-CSF dosing, or may not have been on G-CSF for >15 days. The patient must have documentation of his or her mutational status.

The primary objectives of the following experiments are to determine the safety and tolerability of mavorixafor in patients with severe CIN and selected congenital neutropenia disorders defined as follows:

Severe CIN will be defined in this protocol as patients presenting an ANC of <500 cells/µL, lasting more than 3 months and diagnosed more than 12 months ago, and not attributable to drugs or a specific genetic, infectious, inflammatory, autoimmune, or malignant cause.

Congenital neutropenia conditions that may be treated in accordance with the present study include the following:
a. GSD1b due to mutations in SLC37A4,
b. G6PC3 deficiency due to mutations in G6PC3, and
c. GATA2 deficiency due to mutations in GATA2.

Eligible patients with GSD1b, G6PC3 deficiency, or GATA2 deficiency must be >12 years of age and have a genotype-confirmed mutation that is consistent with 1 of the 3 specified congenital neutropenias: GSD1b, G6PC3 deficiency, or GATA2 deficiency. Patients will be advised of the requirement of genetic screening in the discussion of the trial design and objectives. After signing the informed consent form (ICF), patients will undergo a blood test (or swab) to complete genetic screening for known severe congenital neutropenia, other chronic neutropenia disorders, and primary immunodeficiencies with neutropenia using targeted next-generation sequencing (NGS).

All eligible patients will be treated with mavorixafor at 400 mg by mouth (PO) (QD) in the morning for 14 days.

Patients with severe CIN or one of the selected congenital neutropenias and treated with prophylactic G-CSF at study initiation will not be allowed to have their G-CSF dose or regimen modified during the course of the study and must not have modified their G-CSF dose or regimen within 15 days (inclusive) before the start of study treatment. These patients will receive mavorixafor, 400 mg PO QD in addition to their standard G-CSF regimen for 14 days.

Baseline assessments at Day −1 for eligible patients will occur during a 6-hour hospitalization before the initiation of study drug and will consist of blood sampling to monitor ANC and ALC levels at the following times: 0, 30, 60, and 90 minutes (f 5 minutes each), and 2, 3, 4, and 6 hours (f 15 minutes each). These baseline ANC and ALC values will be averaged and will be thereafter referred to as baseline ANC and ALC. In addition, patients will have an ECG performed at time 0 and 4 hours later.

The administration of the first dose of 400 mg of mavorixafor will occur on Day 1. An ECG will be performed 4 hours post-dose. Blood sampling (PD) to monitor ANC and ALC levels and PK sampling will be performed on Day 1 at the following times: 0 (pre-dose and up to 15 minutes prior), 30, 60, and 90 minutes (5 minutes each), and 2, 3, 4, and 6 hours (15 minutes each) post-dose.

On Day 8, blood sampling (PK/PD) will be performed at the following times: 0 (pre-dose and up to 15 minutes prior), 30, 60, and 90 minutes (f 5 minutes each), and 2, 3, 4, and 6 hours (±15 minutes each) post-dose. Hematology complete blood count and differential will additionally be performed for safety evaluation.

On Day 14 (end of treatment, or EOT), patients will receive their final dose of mavorixafor 400 mg and final blood sampling (PK/PD) at the following times: 0 (pre-dose and up to 15 minutes prior), 30, 60, and 90 minutes (f 5 minutes each), and 2, 3, 4, and 6 hours (f 15 minutes each) post-dose.

At the EOT, patients will continue their baseline G-CSF regimen at 100% of the original weekly dose.

Patients with Selected Congenital Neutropenia/Not Treated with Prophylactic G-CSF Patients with one of the selected congenital neutropenias who have not been treated with prophylactic G-CSF within 30 days of the start of the study, will receive mavorixafor alone, 400 mg PO QD, for 14 days.

Baseline assessments at Day −1 for eligible patients will occur during a 6-hour hospitalization before the initiation of study drug and will consist of blood sampling to monitor ANC levels at the following times: 0, 30, 60, and 90 minutes (f 5 minutes each) and 2, 3, 4, and 6 hours (f 15 minutes each). These baseline ANC and ALC values will be averaged and will be thereafter referred to as baseline ANC and ALC. In addition, patients will have an ECG performed at time 0 and 4 hours later.

The administration of the first dose of 400 mg of mavorixafor will occur on Day 1. An ECG will be performed 4-hours post-dose. Blood sampling (PD) to monitor ANC levels and PK sampling will be performed on Day 1 at the following times: 0 (pre-dose and up to 15 minutes prior), 30, 60, and 90 minutes (f 5 minutes each), and 2, 3, 4, and 6 hours (f 15 minutes each) post-dose.

On Day 8, blood sampling (PK/PD) will be performed at the following times: 0 (pre-dose and up to 15 minutes prior), 30, 60, and 90 minutes (f 5 minutes each), and 2, 3, 4, and hours (f 15 minutes each) post-dose. Hematology complete blood count and differential will additionally be performed for safety evaluation.

On Day 14 (EOT), patients will receive their final dose of mavorixafor 400 mg and final blood sampling (PK/PD) at the following times: 0 (pre-dose and up to 15 minutes prior), 30, 60, and 90 minutes (f 5 minutes each), and 2, 3, 4, and 6 hours (f 15 minutes each) post-dose.

In all patients, in the event of an infection, patients may receive any standard-of-care antibiotic and/or procedure (i.e., drainage).

Patients will be monitored for safety and compliance throughout the study.

If on day 8 the neutrophil count is >30,000 cells/µL at any time point, the patient will discontinue mavorixafor. This will be considered a significant adverse effect (SAE) and the event would be followed until the outcome is known.

If on day 8 the neutrophil count is between 20,000 cells/µL and <30,000 cells/µL, the investigator has the option of monitoring the neutrophil count on days 10 and 12: if the neutrophil count is >30,000 cells/µL, the patient will discontinue mavorixafor. This will be considered an SAE and the event would be followed until the outcome is known.

All patients will attend an End of Study (EOS) visit at 30 days (5 days) posttreatment.

Figure 3:
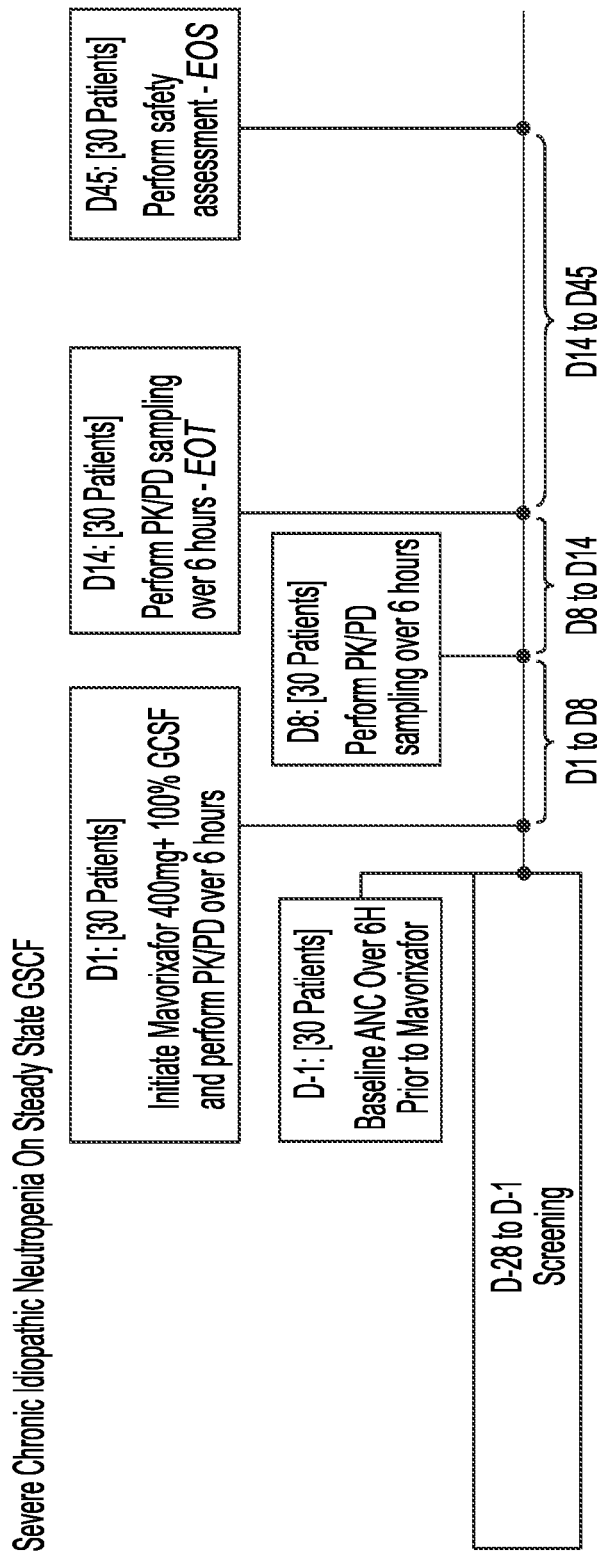
FIG. 3 illustrates study schema for patients with severe chronic idiopathic neutropenia on steady state G-CSF; and selected congenital neutropenia patient populations (with or without G-CSF). Abbreviations: ALC=absolute lymphocyte count; ANC=absolute neutrophil count; $AUC_{ALC}$=area under the curve for ALC; $AUC_{ANC}$=area under the curve for ANC; CIN=chronic idiopathic neutropenia; D=Day; EOS=End of Study; EOT=End of Treatment; G6PC3=glucose-6-phosphatase catalytic subunit 3; GATA2=GATA-binding protein 2; GCSF=granulocyte-colony stimulating factor; H=hours; PD=pharmacodynamic; PK=pharmacokinetic. Primary Endpoint: Safety. Secondary Endpoint: ANC and $AUC_{ANC}$ over 6 hours on Day 14 relative to baseline in patients with severe CIN in combination with steady state GCSF. Exploratory Endpoints: (1) ANC and $AUC_{ANC}$ over 6 hours relative to baseline in patients (with or without GCSF) with glycogen storage disease 1b, G6PC3 deficiency, or GATA2 deficiency; (2) ANC and $AUC_{ALC}$ over 6 hours relative to baseline in all patients; (3) Bone pain in patients treated with GCSF.
Figure 3:
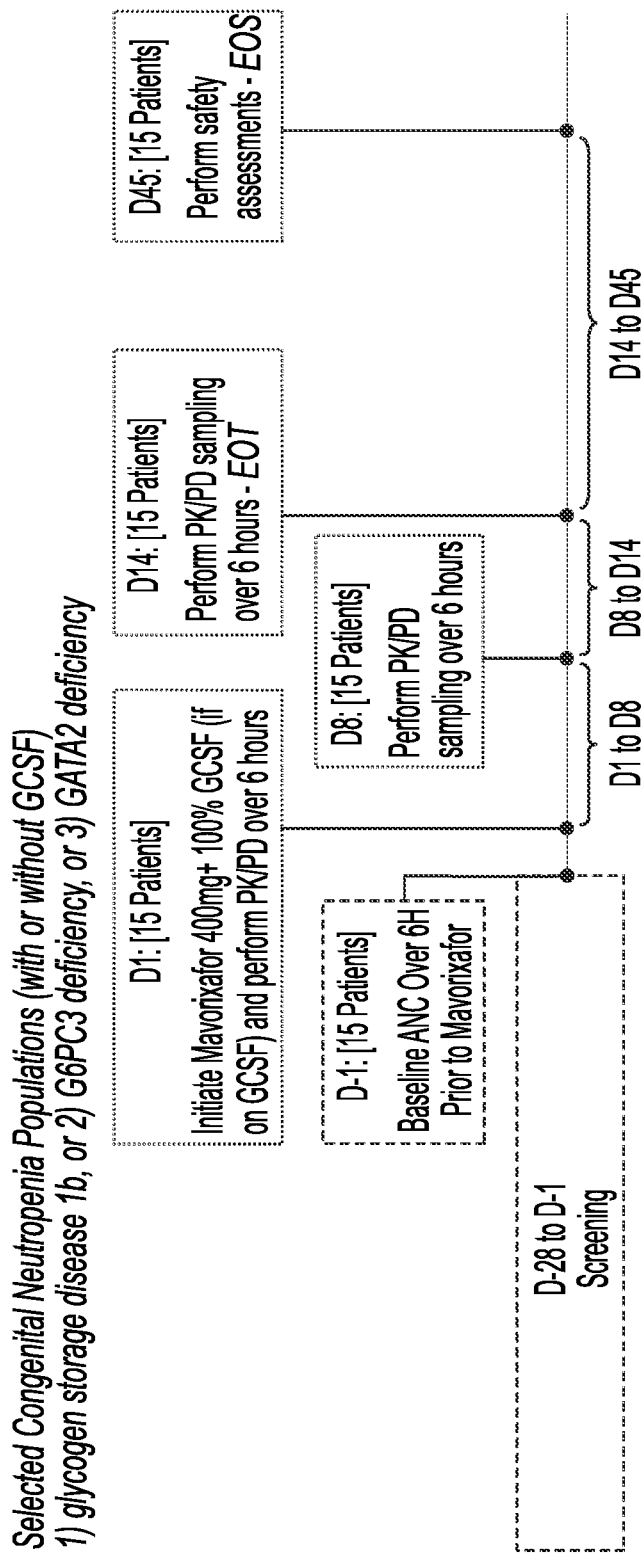

A study schema is presented in FIG. 3. All assessments are to be conducted as described.

Assessment of Efficacy

Absolute neutrophil count and ALC will be measured for the calculation of times above thresholds and AUCs. Patients are scheduled for blood sample collection at the following time points:

Time 0 (pre-dose, up to 15 minutes prior), 30, 60, and 90 minutes (f 5 minutes) and 2, 3, 4, and 6 hours (f 15 minutes each) post-dose.

Absolute neutrophil count and ALC will be determined by standard methods. Whole blood samples will be sent to a central laboratory selected by the Sponsor.

All patients will attend an End of Study (EOS) visit at 30 days (±5 days) posttreatment.

In order to assess the effects of mavorixafor, a detailed statistical analysis will be conducted. Data will be summarized and presented by disease group (CIN, congenital neutropenia). Tabulations will be produced for appropriate disposition, demographic, baseline characteristics, drug exposure, safety and tolerability, and efficacy parameters including ANC, ALC, $AUC_{ANC}$, and $AUC_{ALC}$. Summary statistics will be presented to analyze PK parameters and concentrations. Categorical variables will be summarized by frequency distributions (number and percentages of patients), and continuous variables will be summarized by descriptive statistics (mean, standard deviation, median, minimum, and maximum). No formal statistical testing will be performed.

Reduction and/or Elimination of G-CSF

Presently, standard therapy for severe neutropenia, particularly in subjects with idiopathic neutropenia, i.e., of unknown cause, is treatment with granulocyte-colony stimulating factors ("G-CSFs") such as filgrastim, lenograstim or pegfilgrastim. However, treatment with G-CSF has several substantial drawbacks, including a high incidence of significant bone pain. Bone pain is estimated to occur in anywhere from 24% and [reported on filgrastim and pegfilgrastim labels, respectively] to as high as 66% for filgrastim [Ferguson (2015), Practical Pain Management, vol. 15 online at: practical painmanagement.com/treatments/pharmacological/non-opioids/antihistamine-g-csf-induced-bone-pain] and 59% (24% severe bone pain) for pegfilgrastim (Kirshner et al. (2012) J. Clin Oncol. 30:1974-79). G-CSF is also associated with flu-like symptoms. Further, a link between G-CSF and myeloid malignancies, such as myelodysplasia (MDS) or acute myeloid leukemia (AML) has been reported.

In some embodiments of the present invention, mavorixafor is used for treatment of patients with CIN at risk for infections. The patient may be treated with or without G-CSF.

It is anticipated by the inventors that administration of mavorixafor will permit reduction or discontinuation of the G-CSF for at least some patients. In some cases, this reduces the risk of G-CSF associated malignancy and myelofibrosis, and reduces G-CSF associated bone pain while maintaining protection from infection.

Patients will begin with a well-tolerated dose of oral, daily mavorixafor, for example, at 400 mg per day, to a patient who is presently receiving a full dose (1×) of G-CSF or peg-G-CSF. The patient will be monitored for ANC. If the patient's ANC is at or above 1000 cells/μL, then the clinician will consider reducing the patient's dose of G-CSF or peg-G-CSF by a factor of approximately 25%, (i.e., to 0.75× dose). If ANC remains at or above 1000 cells/μL, the clinician may consider (a) further reducing the patient's dose of G-CSF or peg-G-CSF; (b) revising (i.e., increasing or decreasing) the daily dosage of mavorixafor being administered; or both (a) and (b). ANC will continue to be monitored, with a goal of ANC of at least 500 cell/μL being maintained. As long as the patient's ANC remains above 500 cells/μL, the clinician may consider further reducing the patient's dose of G-CSF or peg-G-CSF with the goal of reducing bone pain or other adverse effects of G-CSF or peg-G-CSF, and will continue to monitor the ANC.

If the patient's measured ANC is found to be between 500 and 1000 cells/μL, the clinician may consider (a) further reducing the patient's dose of G-CSF or peg-G-CSF; (b) increasing the daily mavorixafor dosage; or both (a) and (b). ANC will continue to be monitored, with a goal of ANC of at least 500 cell/μL being maintained. As long as the patient's ANC remains above 500 cells/μL, the clinician may consider further reducing the patient's dose of G-CSF or peg-G-CSF with the goal of reducing bone pain or other adverse effects of G-CSF or peg-G-CSF, and will continue to monitor the ANC.

If the patient's measured ANC is found to be at or below 500 cells/μL, the clinician may consider (a) increasing the patient's dose of G-CSF or peg-G-CSF; (b) increasing the daily mavorixafor dosage; or both (a) and (b).

Long term studies will evaluate the ability to de-escalate G-CSF doses while maintaining ANC levels above 500 cells/μL. As long as the patient's ANC remains above 500 cells/μL, the clinician may consider further reducing the patient's dose of G-CSF or peg-G-CSF, and continue to monitor the ANC.

Other measures of clinical effectiveness or benefit may also be employed in order to determine the efficacy of a treatment regimen using mavorixafor or other CXCR4 inhibitor.

Peripheral WBC counts (≥2 independent samples, obtained in the absence of signs or symptoms of acute infection, and when not having received G- or GM-CSF in the past 7 days) showing absolute neutrophil count <900/μL and/or absolute lymphocyte count <1,500/μL;

Sustained increases in circulating neutrophils (e.g., ANC>600/μL; ANC>800/μL; ANC>1000/μL; or ANC>1,200/μL on at least 85% of assessments).

Sustained increases in circulating lymphocytes (e.g., ALC>1000/μL; ALC>1,200/μL; or ALC>1,500/μL on at least 85% of assessments).

Achieve pre-defined levels of protective antibody in response to at least 2 approved vaccines previously administered without achieving that level.

50% reduction in days of work or school missed due to infection

Sustained increases in circulating neutrophils.

Not all endpoints are applicable to all patients with neutropenia. However, all patients exhibit at least one clinical and one laboratory metric.

Patients may preferably initiated on treatment orally with mavorixafor 25 mg once daily, 25 mg twice daily, or 50 mg once daily. Provision is made for dose reduction (which can be via increased interval; e.g., to every other day or twice weekly) in the event of toxicity or dose increase (e.g., to >50 mg once daily or higher daily dosage, such as 100 mg/day or 150 mg/day) in the event of an inadequate response.

An exemplary initial dosage is via mavorixafor 100 mg capsules, administered orally in the morning in a fasted state, with no food or drink (except water) after midnight and continuing until 2 hr post-dose. In twice daily dosage regimens, capsules are preferably administered orally twelve hours apart.

Example 3: Clinical Treatment Regimens

Dosing Regimen for Patients with Chronic Neutropenia or Congenital Neutropenia:

If the patient experiences adverse effects at any time, in particular a treatment-limiting toxicity, as defined by the National Cancer Institute Common Terminology Criteria for Adverse Events, version 4.03), provision is made for dose reduction (i.e., lower dosage and/or increased interval between administrations drug), or administration is halted. Additionally, the treating physician may use his or her professional judgment and discretion in determining the starting dose, and how best to titrate to the appropriate dose of mavorixafor for any individual patient.

Exemplary compositions of mavorixafor 25 mg, 100 mg, and 200 mg capsules that may be used in methods disclosed herein are shown in Table 10A, 10B, and 10C below.

TABLE 10A

Quantitative Composition of Exemplary Mavorixafor 25 mg Capsule

| Component | Reference to Standard | Function | Quantity (mg/capsule) | % w/w |
|---|---|---|---|---|
| Mavorixafor | In House | Active Ingredient | 25.0 | 14.7 |
| Microcrystalline Cellulose | NF | Diluent | 132.7 | 78.1 |
| Croscarmellose Sodium | NF | Disintegrant | 10.2 | 6.0 |
| Sodium Stearyl Fumarate | NF | Lubricant | 1.7 | 1.0 |
| Colloidal Silicon Dioxide | USP | Flow Aid | 0.4 | 0.2 |
| Sum Total | | | 170 | 100.0 |
| Hard Gelatin Capsules, Size 1 | USP | Packaging | NA | NA |

TABLE 10B

Composition of X4P-001 100 mg Capsules

| Component | Reference to Standard | Function | Quantity (mg/capsule) 100 mg | w/w |
|---|---|---|---|---|
| X4P-001 composition | In House | Active substance | 100.0 | 37.6% |
| Dibasic Calcium Phosphate Dihydrate | USP/NF | Diluent | 84.3 | 31.7% |
| Microcrystalline Cellulose | NF/EP | Diluent | 60.9 | 22.9% |
| Croscarmellose Sodium | NF/EP | Disintegrant | 16.0 | 6.0% |
| Sodium Stearyl Fumarate | NF | Lubricant | 2.7 | 1.0% |
| Sodium Lauryl Sulfate | NF/EP | Wetting agent | 1.3 | 0.5% |
| Colloidal Silicon Dioxide | NF/EP | Flow Aid | 0.8 | 0.3% |
| Sum | | | 266.0 | 100% |
| Hard gelatin capsules, Size 1 white/white. Qualitative composition: Gelatin and Titanium dioxide. | USP | Encapsulation | N/A | N/A |

TABLE 10C

Composition of X4P-001 200 mg Capsules

| Ingredients | 200 mg Percent Per Capsule (%) | Theoretical Amount Per Capsule (mg) |
|---|---|---|
| X4P-001 composition | 61.5 | 200.0 |
| Microcrystalline Cellulose, NF/EP (Avicel PH 101) or equivalent | 12.9 | 41.93 |
| Dibasic Calcium Phosphate Dihydrate, USP/NF | 17.8 | 57.85 |
| Croscarmellose Sodium, NF/EP (Ac-Di-Sol) | 6.0 | 19.50 |
| Sodium Lauryl Sulfate, NF/Ph. Eur. | 0.5 | 1.625 |
| Colloidal Silicone Dioxide, NF/Ph. Eur. (Cab-O-Sil M-5 P) | 0.3 | 0.9750 |
| Sodium Stearyl Fumarate, NF (Pruv) | 1.0 | 3.250 |
| Total Capsule Fill | 100 | 325.0 |

Example 4: Assessments of Treatment Effect

Circulating White Blood Cells

Whole blood samples are analyzed for CBC and absolute leukocyte differential counts by standard laboratory methods, including WBC counts, including absolute numbers of lymphocytes, neutrophils, and CD34+ cells. The number and percentage of patients achieving ANC>1,500/µL; ALC>900/µL. The absolute increase in blood neutrophil counts from pretreatment baseline for each subject, including at the maximum observed in the hours post-dosing; and the maximum observed pre-dose on stable drug administration regimen. These results are compared with data from healthy adults administered X4P-001.

Peripheral Blood Mononuclear Cells (PBMC) subpopulations by flow cytometry are shown below in Table 11.

TABLE 11

Candidate Subsets of Circulating Lymphocytes and Monocytes

| | | |
|---|---|---|
| CD4+ T cells | CD3− CD56+ (NK cells) | CD34+ (stem cells) |
| CD4+ CD45RA+ (naïve T cells) | CD19+ (B cells) | CD49f+ (stem cells) |
| CD4+ CD45RA− (memory T cells) | CD19+ CD27− IgM+ (transitional B cells) | CD90+ (stem cells) |
| CD8+ T cells | CD14+ (monocytes) | |
| CD8+ CD45RA+ (naïve T cells) | CD14+ CD16− (classical monocytes) | |
| CD8+ CD45RA− (memory T cells) | CD14+ CD16+ (inflammatory monocytes) | |

Pharmacokinetic Assessments

If desired, pharmacokinetic assessment of blood samples for plasma levels of X4P-001 may be conducted. Blood samples are collected as scheduled. Samples are analyzed for X4P-001 concentration using reversed-phase high performance liquid chromatography (RP-HPLC) with MS/MS detection. The validated range of this bioanalytic method is 30 to 3,000 ng/mL in plasma.

Pharmacokinetics (PK) and Pharmacodynamics (PD). In order to evaluate the pharmacokinetic properties of therapy with X4P-001, levels of X4P-001, PK samples may be obtained on all patients in Part A as follows:

Day 1: pre-dose; post-dose at 30, 60, 90 min (each±10%) and 2, 3, 4 hr (each±15 min)

Day 8 visit: pre-dose; post-dose at 30, 60, 90 min (each±10%) and 2, 3, 4, 6 hr (each±15 min)

Day 14 visit: pre-dose; post-dose at 30, 60, 90 min (each±10%) and 2, 3, 4, 6 hr (each±15 min)

Visits are scheduled for early in the day and patients are instructed to arrive at the clinic fasting and having not taken their morning dose of X4P-001.

PK are analyzed by patient and dosage regimen over the preceding week using descriptive statistics for AUC, Cmax, and Cmin.

PD samples are collected on Day 1, Day 8 and Day 14 visit concurrent with scheduled PK samples (see above) for:
Total white blood cell (WBC) counts, ANC and ALC.
Assessments may include samples analyzed by flow cytometry for subpopulations of PBMCs.

Of course, the treating physician may apply his or her professional judgment and discretion and any established standards of care, what parameters of assessment (e.g., the desired levels of ANC and ALC) should be used in determining the treatment regimen for any individual patient.

REFERENCES

Baggiolini; 1998. Chemokines and leukocyte traffic. Nature. 392: 565-568.

Bainton et al. (1971) The development of neutrophilic polymorphonuclear leukocytes in human bone marrow. J Exp Med. 134:907-34.

Balabanian, et al. 2012. Proper desensitization of CXCR4 is required for lymphocyte development and peripheral compartmentalization in mice. Blood. 119: 5722-5730.

Banka et al. (2011) Variability of bone marrow morphology in G6PC3 mutations: is there a genotype-phenotype correlation or age-dependent relationship? Am J Hematol. 86:235-7.

Banka and Newman (2013) A clinical and molecular review of ubiquitous glucose-6-phosphatase deficiency caused by G6PC3 mutations. Orphanet J Rare Dis. 8:84.

Banka (2015) G6PC3 deficiency: synonym: ubiquitous glucose-6-phosphatase deficiency. GeneReviews [internet] 2015; Adam et al., editors. Seattle WA: University of Washington, Seattle; 1993-2019.

Broxmeyer et al. (2005) Rapid mobilization of murine and human hematopoietic stem and progenitor cells with AMD3100, a CXCR4 antagonist. J Exp Med 201:1307-18.

Boztug et al. (2009) A syndrome with congenital neutropenia and mutations in G6PC3. N Engl J Med.; 360:32-43.

Cao, et al. (2008) Effect of Low-Dose Ritonavir on the Pharmacokinetics of the CXCR4 Antagonist AMD070 in Healthy Volunteers. Antimicrob Agents Chemother. 52:1630-1634.

Chou and Mansfield (2003) Glucose-6-phosphate transporter: the key to glycogen storage disease type 1b. In: Broer and Wagner, editors. Membrane Transporter Diseases. New York: Springer; 191-205.

Chou et al. (2010) Neutropenia in type 1b glycogen storage disease. Curr Opin Hematol. 17:36-42.

Crispino and Horwitz (2017) GATA factor mutations in hematologic disease. Blood 129:2103-10.

Crump, et al. (1997) Solution structure and basis for functional activity of stromal cell derived factor-1; dissociation of CXCR4 activation from binding and inhibition of HIV-1. EMBO J. 16:6996-7007

Dale et al. (1993) A randomized controlled phase III trial of recombinant human granulocyte colony-stimulating factor (filgrastim) for treatment of severe chronic neutropenia. Blood 81:2496-502.

Dale, et al. (2006) The Severe Chronic Neutropenia International Registry: 10-Year Follow-up Report. Support Cancer Ther. 3:220-31.

Dale and Bolyard (2017) An update on the diagnosis and treatment of chronic idiopathic neutropenia. Curr Opin Hematol. 24:46-53.

Dale et al. (2019) Neutropenia in glycogen storage disease !b: outcomes for patients treated with granulocyte colony-stimulating factor. Curr Opin Hematol. 26:16-21.

Doranz (1997). Chemokine receptors as fusion cofactors for human immunodeficiency virus type (HIV-1). Immunol Res. 16:15-28.

Dresch et al. (1975) Kinetic studies of 51Cr and DF32P labelled granulocytes. Br J Haematol. 29:67-80.

Eash et al. (2009) CXCR4 is a key regulator of neutrophil release from the bone marrow under basal and stress granulopoiesis conditions. Blood. 113:4711-19.

FDA Drug development and drug interactions: table of substrates, inhibitors and inducers. Updated 14 Nov. 2017. Available at fda.gov/drugs/drug-interactions-labeling/drug-development-and-drug-interactions-table-substrates-inhibitors-and-inducers. Accessed 22 Jun. 2019.

Galsky, et al. (2014). A Phase I Trial of LY2510924, a CXCR4 Peptide Antagonist, in Patients with Advanced Cancer. Clin Cancer Res. doi:10.1158/1078-0432.CCR-13-2686.

Goldman et al. (2016) Hyperglycemia associated with targeted oncologic treatment: mechanisms and management. Oncologist. 21:1326-36.

Greenberg et al. (1980) The chronic idiopathic neutropenia syndrome: correlation of clinical features with in vitro parameters of granulocytopoiesis. Blood. 55:915-921.

Hayee, et al. (2011) G6PC3 mutations are associated with a major defect of glycosylation: a novel mechanism for neutrophil dysfunction. Glycobiology, 21:914-24.

Hendrix, et al. 2004. Safety, Pharmacokinetics, and Antiviral Activity of AMD3100, a Selective CXCR4 Receptor Inhibitor, in HIV-1 Infection. J Acquir Immune Defic Syndr. 37:1253-1262.

Hickstein (2018) HSCT for GATA2 deficiency across the pond. Blood. 131:1272-74.

Hsu et al. (2015) GATA2 deficiency. Curr Opin Allergy Clin Immunol. 15:104-9.

Kawai, et al.; WHIM syndrome myelokathexis reproduced in the NOD/SCID mouse xenotransplant model engrafted with healthy human stem cells transduced with C terminus-truncated CXCR4. Blood. 2007; 109:78-84. Epub 2006 Aug. 31.

Kim et al. (2006) G-CSF down-regulation of CXCR3 expression identified as a mechanism for mobilization of myeloid cells. Blood. 108:812-20.

Kim et al. (2008) Neutrophil stress and apoptosis underlie myeloid dysfunction in glycogen storage disease type 1b. Blood. 111:5704-11.

Kyle and Linman. (1968) Chronic idiopathic neutropenia. A newly recognized entity? N Engl J Med. 279:1015-19.

Lagane, et al. (2008) CXCR4 dimerization and beta-arrestin-mediated signaling account for the enhanced chemotaxis to CXCL12 in WHIM syndrome. Blood. 112:34-44.

Lapidot and Petit (2002) Current understanding of stem cell mobilization: the roles of chemokines, proteolytic enzymes, adhesion molecules, cytokines, and stromal cells. Exp Hematol. 30:973-981.

Levesque et al. (2003) Disruption of the CXCR4/CXCR12 chemotactic interaction during hematopoietic stem cell mobilization induced by G-CSF or cyclophosphamide. J Clin Invest. 111:187-96.

Liles et al. (2003) Mobilization of hematopoietic progenitor cells in healthy volunteers by AMD3100, a CXCR4 antagonist. Blood. 102:2728-30.

Link (2005) Neutrophil homeostasis: a new role for stromal cell-derived factor-1. Immunol Res. 32:169-78.

Lord et al. (1991) Myeloid cell kinetics in mice treated with recombinant interleukin-3, granulocyte colony-stimulating factor (GSF), or granulocyte-macrophage CSF in vivo. Blood. 77:2154-9.

Ma et al. (1999) The chemokine receptor CXCR4 is required for retention of B lineage and granulocytic precursors in the bone marrow microenvironment. Immunity. 10:463-471.

Maciejewski-Duval et al. (2016) Altered chemotactic response to CXCL12 in patients carrying GATA2 mutations. J Leukoc Bio. 99:1065-76.

Martin et al. (2014) Births in the United States, 2013. National Center for Health Statistics Data Brief. No. 175: December 2014.

McCormick et al. (2009) Impaired recruitment of Grk6 and beta-Arrestin 2 causes delayed internalization and desensitization of a WHIM syndrome-associated CXCR4 mutant receptor. PLoS One. 4:e8102.

a) McDermott et al. (2011) The CXCR4 antagonist plerixafor corrects panleukopenia in patients with WHIM syndrome. Blood. 118:4957-62.

b) McDermott et al (2014) A phase 1 clinical trial of long-term, low-dose treatment of WHIM syndrome with the CXCR4 antagonist plerixafor. Blood. 123:2308-16.

c) McDermott et al. (2010) Severe congenital neutropenia resulting from G6PC3 deficiency with increased neutrophil CXCR4 expression and myelokathexis. Blood 116: 2793-802.

Mosi, et al. (2012) The molecular pharmacology of AMD11070: An orally bioavailable CXCR4 HIV entry inhibitor. Biochem Pharmacology. 83:472-479.

Moyle, et al. (2009) Proof of Activity with AMD11070, an Orally Bioavailable Inhibitor of CXCR4-Tropic HIV Type 1. Clin Infect Dis. 48:798-805.

Nyunt, et al. (2008) Pharmacokinetic Effect of AMD070, an Oral CXCR4 Antagonist, on CYP3A4 and CYP2D6 Substrates Midazolam and Dextromethorphan in Healthy Volunteers. J Acquir Immune Defic Syndr. 47:559-565.

Parker. (2001) Glucose-6-phosphate translocase as a target for the design of antidiabetic agents. Drugs Fut. 26:687.

Pillay et al. (2010) In vivo labeling with 2H2O reveals a human neutrophil lifespan of 5.4 days. Blood. 116:625-7.

Roe et al. (2002) Inflammatory bowel disease in glycogen storage disease type 1b. J Pediatr 109:55-9.

Semerad et al. (2002) G-CSF is an essential regulator of neutrophil trafficking from the bone marrow to the blood. Immunity. 17:413-23.

Sicre de Fontbrune et al. (2015) Severe chronic primary neutropenia in adults: report on a series of 108 patients. Blood. 126:1643-50.

Stone, et al. (2007) Multiple-Dose Escalation Study of the Safety, Pharmacokinetics, and Biologic Activity of Oral AMD070, a Selective CXCR4 Receptor Inhibitor, in Human Subjects. Antimicrob Agents Chemother. 51:2351-2358.

Suratt et al. (2004) Role of the CXCR4/SDF-1 chemokine axis in circulating neutrophil homeostasis. Blood. 104: 565-71.

Ueno et al. (1986) Impaired monocyte function in glycogen storage disease type 1d. Eur J Pediatr. 145:312-14.

Veiga-da-Cunha et al. (2019) Failure to eliminate a phosphorylated glucose analog leads to neutropenia in patients with G6PT and G6PC #3 deficiencies. Proc Natl Acad Sci USA. 116:1241-50.

Vinh et al. (2010) Autosomal dominant and sporadic monocytopenia with susceptibility to mycobacteria, fungi, papillomaviruses, and myelodysplasia. Blood. 115:1519-29.

Visser et al. (2000) Neutropenia, neutrophil dysfunction, and inflammatory bowel disease in glycogen storage disease type 1b: results of the European Study on Glycogen Storage Disease type I. J Pediatr. 137:187-91.

Visser et al. (2006) Granulocyte colony-stimulating factor in glycogen storage disease type 1b. Results of the European study on glycogen storage disease type 1. Eur J Pediatr. 161 (Suppl 1):S83-7.

Ward and Dale (2009) Genetic and molecular diagnosis of severe congenital neutropenia. Curr Opin Hematol. 16:9-13.

Wong (2008) Comparison of the potential multiple binding modes of bicyclam, monocylam, and noncyclam small molecule CXC chemokine receptor 4 inhibitors. Mol Pharmacol. 74:1485-1495.

Zlotnik and Yoshie (2000) Chemokines: a new classification system and their role in immunity. Immunity. 12:121-127.

INTERNET REFERENCES

George Diaz, Virginia Gulino. Whim syndrome. Orphanet Encyclopedia. June 2004; orpha.net/data/patho/GB/uk-Whim.pdf NORD (National Organization for Rare Diseases) 2015: rarediseases.org/rarediseases/whim-syndrome Office of Rare Diseases: rarediseases.info.nih.gov/gard/9297/whimsyndrome/resources/1 Orphanet, WHIM Syndrome:

orpha.net/consor/www/cgibin/OC_Exp.php?lng=EN&Expert=51636 Last Update October 2014.

US Census Bureau: census.gov/quickfacts/table/PST045214/00 Last Revised June 2015.

We claim:

1. A method for treating chronic neutropenia, cyclic neutropenia, or congenital neutropenia in a patient in need thereof, wherein the patient does not have a gain-of-function mutation in the CXCR4 gene, comprising administering to the patient an amount of mavorixafor:

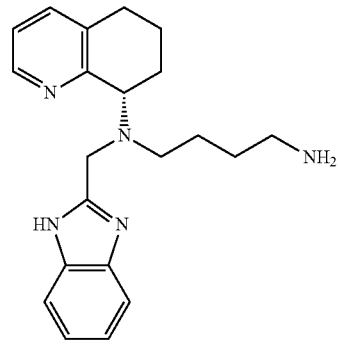 [SMILES: NCCCCN(Cc1nc2ccccc2[nH]1)[C@H]1CCCc2cccnc21]

or a pharmaceutically acceptable salt or composition thereof effective to increase absolute neutrophil count (ANC) to a level greater than or equal to 500 cells/µL and absolute lymphocyte count (ALC) to a level greater than 1000 cells/µL in the patient;

wherein the patient has an absolute neutrophil count (ANC) less than 500 cells/µL at a baseline prior to administering mavorixafor or a pharmaceutically acceptable salt or composition thereof;

the amount of mavorixafor or a pharmaceutically acceptable salt or composition thereof administered is about 200 mg/day, about 300 mg/day, or about 400 mg/day;

the patient has not been diagnosed with WHIM syndrome or with myelokathexis; and wherein the method results in an increase of ANC to at least 2.0 x the baseline.

2. The method of claim 1, wherein the patient has chronic idiopathic neutropenia (CIN), severe chronic neutropenia (SCN), or autoimmune neutropenia (AIN).

3. The method of claim 1, wherein the patient has chronic idiopathic neutropenia (CIN).

4. The method of claim 1, wherein mavorixafor is administered at a dose of 300 mg/day.

5. The method of claim 1, wherein mavorixafor is administered at a dose of 400 mg/day.

6. The method of claim 1, wherein the method is effective to increase absolute neutrophil count (ANC) to a level of at least 800 cells/μL on at least 85% of assessments.

7. The method of claim 1, wherein the method is effective to increase absolute lymphocyte count (ALC) to a level of at least 1,500 cells/μL on at least 85% of assessments.

8. The method of claim 1, wherein mavorixafor or a pharmaceutically acceptable salt thereof is administered at a dose of 200 mg/day.

* * * * *